(12) United States Patent
Glithero et al.

(10) Patent No.: US 11,738,171 B2
(45) Date of Patent: Aug. 29, 2023

(54) CATHETER INSERTION TRAY WITH INTEGRATED INSTRUCTIONS

(71) Applicant: C. R. Bard, Inc., Franklin Lakes, NJ (US)

(72) Inventors: Jason I. Glithero, Mcdonough, GA (US); Scott Robirds, Alpharetta, GA (US); Adam Silver, Atlanta, GA (US); Peter Curry, Decatur, GA (US); Salvatore Privitera, Mason, OH (US); Robin J. Hanson, Alpharetta, GA (US); David Icenogle, Atlanta, GA (US); Fung Bor Chen, Covington, GA (US); Grace Powers, Smyrna, GA (US); Stacey Hodges, Carrollton, VA (US); Russell Riescher, Loganville, GA (US); Johnathan Johnson, Mt. Pleasant, SC (US); Sarah Skelton, Atlanta, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 341 days.

(21) Appl. No.: 16/943,902

(22) Filed: Jul. 30, 2020

(65) Prior Publication Data
US 2020/0353204 A1    Nov. 12, 2020

Related U.S. Application Data

(62) Division of application No. 15/029,613, filed as application No. PCT/US2014/060963 on Oct. 16, 2014, now Pat. No. 10,758,705.

(Continued)

(51) Int. Cl.
*A61M 25/00* (2006.01)
*A61B 50/33* (2016.01)
(Continued)

(52) U.S. Cl.
CPC .......... *A61M 25/002* (2013.01); *A61B 42/00* (2016.02); *A61B 46/00* (2016.02); *A61B 50/00* (2016.02);
(Continued)

(58) Field of Classification Search
CPC .............. A61M 25/00; A61M 25/0017; A61M 25/002; A61M 25/0113; A61B 19/02;
(Continued)

(56) References Cited

U.S. PATENT DOCUMENTS

| 935,419 A | 9/1909 | Smith |
|---|---|---|
| 2,346,636 A | 4/1944 | Porter |

(Continued)

FOREIGN PATENT DOCUMENTS

| CN | 1511014 A | 7/2004 |
|---|---|---|
| CN | 201823147 U | 5/2011 |

(Continued)

OTHER PUBLICATIONS

"Arrow International, Inc. Introduces Maximal Barrier Precautions Tray", Press release. Jan. 11, 2006.
(Continued)

*Primary Examiner* — Javier A Pagan
(74) *Attorney, Agent, or Firm* — Rutan & Tucker LLP

(57) ABSTRACT

An improved medical procedure or catheterization tray included in an improved medical procedure or catheterization package. The improved medical procedure or catheterization tray is intuitively arranged and includes instructions printed thereon to improve the medical procedure or catheterization implementation and results. In one example, a catheterization package and catheterization tray has a layout and/or arrangement of components that may help reduce CAUTI rates by facilitating ease of use and aiding in proper aseptic technique during insertion. The medical procedure or (Continued)

catheterization package and/or medical procedure or catheterization tray may include various implements, compartments, and components necessary and/or helpful to the medical procedure or catheterization, including, for example, improved swabs and an improved compartment for holding the swabs.

24 Claims, 43 Drawing Sheets

Related U.S. Application Data

(60) Provisional application No. 62/015,206, filed on Jun. 20, 2014, provisional application No. 61/891,496, filed on Oct. 16, 2013.

(51) Int. Cl.

| | | |
|---|---|---|
| G09B 19/00 | (2006.01) | |
| A61B 90/94 | (2016.01) | |
| A61B 46/00 | (2016.01) | |
| A61B 50/30 | (2016.01) | |
| A61B 42/00 | (2016.01) | |
| A61B 50/00 | (2016.01) | |
| A61B 50/20 | (2016.01) | |
| B65D 25/20 | (2006.01) | |
| A61F 13/38 | (2006.01) | |
| A61M 5/00 | (2006.01) | |

(52) U.S. Cl.
CPC ............ *A61B 50/20* (2016.02); *A61B 50/30* (2016.02); *A61B 50/33* (2016.02); *A61B 90/94* (2016.02); *A61M 25/0017* (2013.01); *B65D 25/205* (2013.01); *G09B 19/00* (2013.01); *A61B 2050/006* (2016.02); *A61B 2050/0056* (2016.02); *A61B 2050/3008* (2016.02); *A61B 2050/3015* (2016.02); *A61B 2050/314* (2016.02); *A61F 13/38* (2013.01); *A61M 5/002* (2013.01)

(58) Field of Classification Search
CPC ..... A61B 19/0271; A61B 50/30; A61B 50/33; A61B 42/00; A61B 2050/3008; A61B 2050/3015; A61B 2050/314; B65D 25/205; A61F 13/38
USPC ................ 206/216, 223, 364–366, 570, 571
See application file for complete search history.

(56) References Cited

U.S. PATENT DOCUMENTS

| | | | |
|---|---|---|---|
| 2,659,485 | A | 11/1953 | Duley et al. |
| 2,874,707 | A | 2/1959 | Koppel |
| 2,947,415 | A | 8/1960 | Garth |
| 3,107,786 | A | 10/1963 | Adelman |
| 3,137,387 | A | 6/1964 | Overment |
| 3,138,253 | A | 6/1964 | Harautuneian |
| 3,144,932 | A | 8/1964 | Zerbo, Jr. |
| 3,166,189 | A | 1/1965 | Disston |
| 3,324,855 | A | 6/1967 | Heimlich |
| 3,329,261 | A | 7/1967 | Serany, Jr. et al. |
| 3,345,988 | A | 10/1967 | Vitello |
| 3,379,339 | A | 4/1968 | Asenbauer |
| 3,485,352 | A | 12/1969 | Pilger |
| D218,077 | S | 7/1970 | Gabriel |
| 3,542,019 | A | 11/1970 | Gittins |
| 3,580,475 | A | 5/1971 | Mobley |
| D222,312 | S | 10/1971 | Kurtz et al. |
| 3,642,123 | A | 2/1972 | Knox |
| 3,650,393 | A | 3/1972 | Reiss et al. |
| 3,726,281 | A | 4/1973 | Norton et al. |
| 3,762,399 | A | 10/1973 | Riedell |
| 3,770,119 | A | 11/1973 | Hultberg et al. |
| 3,802,555 | A | 4/1974 | Grasty et al. |
| 3,851,649 | A | 12/1974 | Villar |
| D234,404 | S | 2/1975 | Merril |
| 3,901,235 | A | 8/1975 | Patel et al. |
| D237,315 | S | 10/1975 | Nowakowski |
| D237,317 | S | 10/1975 | Nowakowski |
| 3,965,900 | A | 6/1976 | Boedecker |
| 3,967,728 | A | 7/1976 | Gordon et al. |
| 3,976,195 | A | 8/1976 | Cohen |
| 3,978,983 | A | 9/1976 | Brezette |
| 3,981,398 | A | 9/1976 | Boshoff |
| D242,654 | S | 12/1976 | Rawls |
| 3,998,221 | A | 12/1976 | Collins |
| D243,798 | S | 3/1977 | Swartz |
| 4,011,944 | A | 3/1977 | Cooley et al. |
| 4,053,280 | A | 10/1977 | Salisbury |
| 4,085,845 | A | 4/1978 | Perfect |
| D248,871 | S | 8/1978 | Forsman et al. |
| D249,362 | S | 9/1978 | Forsman et al. |
| 4,140,127 | A | 2/1979 | Cianci et al. |
| 4,149,635 | A | 4/1979 | Stevens |
| 4,153,160 | A | 5/1979 | Leigh |
| 4,160,505 | A | 7/1979 | Rauschenberger |
| 4,170,300 | A | 10/1979 | Pick |
| 4,226,328 | A | 10/1980 | Beddow |
| 4,256,225 | A | 3/1981 | Jackson |
| 4,262,800 | A | 4/1981 | Nethercutt |
| 4,266,669 | A | 5/1981 | Watson |
| D262,995 | S | 2/1982 | Gaba et al. |
| 4,332,322 | A | 6/1982 | Jaeschke et al. |
| 4,334,537 | A | 6/1982 | Peterson |
| 4,366,901 | A | 1/1983 | Short |
| D268,130 | S | 3/1983 | Easton |
| 4,458,705 | A | 7/1984 | Cawood |
| D275,886 | S | 10/1984 | Sheward et al. |
| D276,462 | S | 11/1984 | Villarreal |
| D277,508 | S | 2/1985 | Clair |
| 4,501,363 | A | 2/1985 | Isbey, Jr. |
| 4,522,302 | A | 6/1985 | Paikoff |
| 4,523,679 | A | 6/1985 | Paikoff et al. |
| 4,530,349 | A | 7/1985 | Metzger |
| D280,663 | S | 9/1985 | Albon et al. |
| D280,933 | S | 10/1985 | McLaughlin |
| D283,051 | S | 3/1986 | Fichera |
| 4,595,102 | A | 6/1986 | Cianci et al. |
| D287,760 | S | 1/1987 | Discko, Jr. |
| 4,767,008 | A | 8/1988 | Warnecke et al. |
| 4,795,441 | A | 1/1989 | Bhatt |
| 4,811,847 | A | 3/1989 | Reif et al. |
| 4,828,113 | A | 5/1989 | Friedland et al. |
| 4,844,259 | A | 7/1989 | Glowczewskie, Jr. et al. |
| 4,858,821 | A | 8/1989 | Bickelhaupt |
| 4,925,448 | A | 5/1990 | Bazaral |
| 4,928,830 | A | 5/1990 | Brewer |
| 4,944,427 | A | 7/1990 | Yamada et al. |
| D310,896 | S | 9/1990 | Winjum |
| 4,989,733 | A | 2/1991 | Patry |
| 5,007,535 | A | 4/1991 | Meseke et al. |
| 5,024,326 | A | 6/1991 | Sandel et al. |
| 5,031,768 | A | 7/1991 | Fischer |
| 5,098,391 | A | 3/1992 | Pantages et al. |
| 5,163,557 | A | 11/1992 | Sokolowski |
| 5,170,804 | A | 12/1992 | Glassman |
| 5,174,306 | A | 12/1992 | Marshall |
| D334,973 | S | 4/1993 | Valentine et al. |
| D337,830 | S | 7/1993 | Coyne et al. |
| 5,242,398 | A | 9/1993 | Knoll et al. |
| D343,687 | S | 1/1994 | Houghton et al. |
| 5,306,239 | A | 4/1994 | Gurmarnik et al. |
| 5,318,543 | A | 6/1994 | Ross et al. |
| 5,322,163 | A | 6/1994 | Foos |
| 5,339,955 | A | 8/1994 | Horan et al. |
| D351,661 | S | 10/1994 | Fischer |
| D353,078 | S | 12/1994 | Davis et al. |
| 5,384,103 | A | 1/1995 | Miller |
| 5,392,918 | A | 2/1995 | Harrison |
| 5,394,983 | A | 3/1995 | Latulippe et al. |

(56) References Cited

U.S. PATENT DOCUMENTS

| | | |
|---|---|---|
| 5,449,071 A | 9/1995 | Levy |
| 5,525,314 A | 6/1996 | Hurson |
| 5,586,163 A | 12/1996 | Goldstein |
| 5,590,778 A | 1/1997 | Dutchik |
| D380,272 S | 6/1997 | Partika et al. |
| D387,177 S | 12/1997 | Davis |
| D387,559 S | 12/1997 | Williamson |
| 5,704,914 A | 1/1998 | Stocking et al. |
| 5,752,234 A | 5/1998 | Withers |
| 5,779,053 A | 7/1998 | Partika et al. |
| 5,810,738 A | 9/1998 | Thomas, II |
| 5,931,303 A | 8/1999 | Salvadori |
| 5,941,241 A | 8/1999 | Weinstein et al. |
| 5,947,284 A | 9/1999 | Foster |
| 5,947,890 A | 9/1999 | Spencer et al. |
| 5,975,295 A | 11/1999 | Diamond |
| 6,004,136 A | 12/1999 | Ehrenpreis |
| 6,012,586 A | 1/2000 | Misra |
| 6,068,121 A | 5/2000 | McGlinch |
| 6,090,075 A | 7/2000 | House |
| 6,121,165 A | 9/2000 | Mackey et al. |
| 6,142,152 A | 11/2000 | Gawarecki |
| 6,158,437 A | 12/2000 | Vagley |
| D437,941 S | 2/2001 | Frattini |
| D442,697 S | 5/2001 | Hajianpour |
| D445,198 S | 7/2001 | Frattini |
| D450,130 S | 11/2001 | Goldstein |
| D450,391 S | 11/2001 | Hunt et al. |
| 6,382,212 B1 | 5/2002 | Borchard |
| 6,405,863 B1 | 6/2002 | Dhindsa |
| 6,412,639 B1 | 7/2002 | Hickey |
| 6,454,097 B1 | 9/2002 | Blanco |
| 6,502,699 B1 | 1/2003 | Watson |
| D471,640 S | 3/2003 | McMichael et al. |
| D471,641 S | 3/2003 | McMichael et al. |
| 6,579,271 B1 | 6/2003 | Aruffo et al. |
| D480,816 S | 10/2003 | McMichael et al. |
| 6,640,976 B1 | 11/2003 | Franks-Farah et al. |
| 6,681,933 B1 | 1/2004 | Demsien et al. |
| 6,716,200 B2 | 4/2004 | Bracken et al. |
| 6,769,546 B2 | 8/2004 | Busch |
| D495,491 S | 9/2004 | Ramirez et al. |
| D495,807 S | 9/2004 | Agbodoe et al. |
| 6,793,078 B2 | 9/2004 | Roshdy |
| 6,840,379 B2 | 1/2005 | Franks-Farah et al. |
| 6,896,141 B2 | 5/2005 | McMichael et al. |
| 6,907,992 B2 | 6/2005 | McMichael et al. |
| 6,910,581 B2 | 6/2005 | McMichael et al. |
| 6,915,901 B2 | 7/2005 | Feinberg et al. |
| 6,926,708 B1 | 8/2005 | Franks-Farah et al. |
| 6,948,742 B2 | 9/2005 | Buck |
| 6,959,808 B2 | 11/2005 | Discko, Jr. |
| 6,991,096 B2 | 1/2006 | Gottlieb et al. |
| 7,048,120 B2 | 5/2006 | Pond |
| 7,066,328 B2 | 6/2006 | Pulsifer |
| D530,920 S | 10/2006 | Snell |
| 7,131,965 B1 | 11/2006 | Thornbury et al. |
| D547,064 S | 7/2007 | Snell |
| D549,454 S | 8/2007 | Ahman |
| 7,264,869 B2 | 9/2007 | Tobita et al. |
| 7,278,987 B2 | 10/2007 | Solazzo |
| D557,047 S | 12/2007 | Dretzka |
| D561,473 S | 2/2008 | Phillips et al. |
| D563,673 S | 3/2008 | Dretzka |
| 7,401,703 B2 | 7/2008 | McMichael et al. |
| 7,410,053 B2 | 8/2008 | Bowen et al. |
| 7,434,687 B2 | 10/2008 | Itou et al. |
| D579,662 S | 11/2008 | Dretzka |
| 7,491,176 B2 | 2/2009 | Mann |
| 7,494,487 B2 | 2/2009 | Timm |
| D590,596 S | 4/2009 | Dretzka |
| D596,311 S | 7/2009 | Antons |
| 7,624,869 B2 | 12/2009 | Primer |
| 7,634,893 B2 | 12/2009 | Gottlieb et al. |
| D609,819 S | 2/2010 | Tomes et al. |
| 7,662,146 B2 | 2/2010 | House |
| D612,153 S | 3/2010 | Liao |
| 7,671,014 B2 | 3/2010 | Beals et al. |
| D613,418 S | 4/2010 | Ryan et al. |
| D618,821 S | 6/2010 | Larsen |
| 7,743,918 B2 | 6/2010 | Itou et al. |
| 7,785,312 B2 | 8/2010 | Thorne, Jr. et al. |
| D623,765 S | 9/2010 | Tomes et al. |
| D631,558 S | 1/2011 | Harmston et al. |
| D636,894 S | 4/2011 | Tomes et al. |
| D638,137 S | 5/2011 | Gross et al. |
| 7,993,326 B2 | 8/2011 | Massengale et al. |
| D646,796 S | 10/2011 | Walter |
| D650,912 S | 12/2011 | Tomes et al. |
| 8,128,595 B2 | 3/2012 | Walker et al. |
| 8,177,064 B2 | 5/2012 | McCormick et al. |
| D662,218 S | 6/2012 | Pittman |
| 8,240,468 B2 | 8/2012 | Wilkinson et al. |
| 8,273,312 B2 | 9/2012 | Porat et al. |
| 8,282,829 B2 | 10/2012 | Yu et al. |
| 8,448,786 B2 | 5/2013 | Tomes et al. |
| D688,461 S | 8/2013 | Ambrefe, Jr. et al. |
| 8,584,849 B2 * | 11/2013 | McCaffrey ........... A61M 25/002 206/364 |
| 8,597,505 B2 | 12/2013 | Fulkerson et al. |
| 8,628,549 B2 | 1/2014 | To et al. |
| 8,631,935 B2 | 1/2014 | Tomes et al. |
| 8,656,929 B2 | 2/2014 | Miller et al. |
| 8,662,306 B2 * | 3/2014 | Agrawal ............. A61M 25/002 206/370 |
| 8,678,190 B2 | 3/2014 | Tomes et al. |
| 8,708,999 B2 | 4/2014 | Hong et al. |
| D704,856 S | 5/2014 | Tomes et al. |
| D707,848 S | 6/2014 | Shigeno et al. |
| 8,746,452 B2 | 6/2014 | Tomes et al. |
| D708,347 S | 7/2014 | Lober |
| D708,759 S | 7/2014 | Heyman et al. |
| 8,875,940 B2 | 11/2014 | Danchisin et al. |
| D720,470 S | 12/2014 | Lober |
| D720,471 S | 12/2014 | Angel et al. |
| 9,084,593 B2 | 7/2015 | Yakel et al. |
| D738,491 S | 9/2015 | Foley et al. |
| 9,162,781 B2 | 10/2015 | Lien |
| 9,186,217 B2 | 11/2015 | Goyal |
| D751,726 S | 3/2016 | Nishioka et al. |
| 9,283,352 B2 | 3/2016 | Tomes et al. |
| 9,486,604 B2 | 11/2016 | Murray et al. |
| 9,522,001 B2 | 12/2016 | Bui et al. |
| 9,522,753 B2 | 12/2016 | Tomes et al. |
| 9,693,756 B2 | 7/2017 | Tomes et al. |
| 9,744,333 B2 * | 8/2017 | Terzibashian ............ B65D 1/34 |
| 9,745,088 B2 | 8/2017 | Tomes et al. |
| 9,795,761 B2 | 10/2017 | Lockwood et al. |
| 9,808,400 B2 | 11/2017 | Tomes et al. |
| 9,808,596 B2 | 11/2017 | Tomes et al. |
| 9,872,969 B2 | 1/2018 | Conway et al. |
| 10,022,464 B2 | 7/2018 | Sarphati et al. |
| 10,039,897 B2 | 8/2018 | Norris et al. |
| 10,106,295 B2 | 10/2018 | Lockwood |
| 10,251,812 B2 | 4/2019 | Tomes et al. |
| 10,512,752 B2 | 12/2019 | Tomes et al. |
| 10,639,120 B2 | 5/2020 | Turturro et al. |
| 2002/0185406 A1 | 12/2002 | Massengale et al. |
| 2003/0038475 A1 | 2/2003 | Stancil |
| 2003/0060761 A1 | 3/2003 | Evans et al. |
| 2003/0075474 A1 | 4/2003 | Moyer et al. |
| 2003/0159966 A1 | 8/2003 | McMichael et al. |
| 2003/0159967 A1 | 8/2003 | McMichael et al. |
| 2003/0159968 A1 | 8/2003 | McMichael et al. |
| 2003/0159969 A1 | 8/2003 | McMichael et al. |
| 2003/0211627 A1 | 11/2003 | Koesterman et al. |
| 2004/0004019 A1 | 1/2004 | Busch |
| 2004/0055919 A1 | 3/2004 | Rowe et al. |
| 2004/0060260 A1 | 4/2004 | Gottlieb et al. |
| 2004/0111072 A1 | 6/2004 | McKissick |
| 2004/0161732 A1 | 8/2004 | Stump et al. |
| 2004/0180822 A1 | 9/2004 | Grafton |
| 2004/0195145 A1 | 10/2004 | Roshdy |
| 2004/0200754 A1 | 10/2004 | Hagemeier |

(56) References Cited

U.S. PATENT DOCUMENTS

| | | |
|---|---|---|
| 2004/0238391 A1 | 12/2004 | Pond |
| 2005/0022822 A1 | 2/2005 | Santilli et al. |
| 2005/0098470 A1 | 5/2005 | Davis et al. |
| 2005/0101905 A1 | 5/2005 | Merry |
| 2005/0236940 A1 | 10/2005 | Rockoff |
| 2005/0256453 A1 | 11/2005 | Nagamatsu |
| 2005/0285385 A1 | 12/2005 | Bova et al. |
| 2006/0009742 A1 | 1/2006 | Solazzo |
| 2006/0086634 A1 | 4/2006 | Steppe |
| 2006/0104857 A1 | 5/2006 | Pigott et al. |
| 2006/0186010 A1 | 8/2006 | Warnack et al. |
| 2006/0205996 A1 | 9/2006 | Presthus et al. |
| 2006/0224086 A1 | 10/2006 | Harty |
| 2006/0264822 A1 | 11/2006 | Nagamatsu |
| 2006/0271019 A1 | 11/2006 | Stoller et al. |
| 2006/0282045 A1 | 12/2006 | Wilkinson et al. |
| 2007/0026472 A1 | 2/2007 | Prokash et al. |
| 2007/0049806 A1 | 3/2007 | Adams et al. |
| 2007/0060908 A1 | 3/2007 | Webster et al. |
| 2007/0084742 A1 | 4/2007 | Miller et al. |
| 2007/0088330 A1 | 4/2007 | House |
| 2007/0095699 A1 | 5/2007 | Frieze et al. |
| 2007/0142786 A1 | 6/2007 | Lampropoulos et al. |
| 2007/0156099 A1 | 7/2007 | Fowler |
| 2007/0161971 A1 | 7/2007 | House |
| 2007/0197998 A1 | 8/2007 | Itou et al. |
| 2007/0225687 A1 | 9/2007 | House |
| 2007/0273258 A1 | 11/2007 | Ernst |
| 2007/0299431 A1 | 12/2007 | Jakubowski et al. |
| 2008/0045861 A1 | 2/2008 | Miller et al. |
| 2008/0058725 A1 | 3/2008 | Scribner et al. |
| 2008/0116106 A1 | 5/2008 | Lampropoulos et al. |
| 2008/0121553 A1 | 5/2008 | Gobel |
| 2008/0125722 A1 | 5/2008 | Hess et al. |
| 2008/0172042 A1 | 7/2008 | House |
| 2008/0221515 A1 | 9/2008 | Nagamatsu |
| 2008/0249482 A1 | 10/2008 | Erez |
| 2008/0272023 A1 | 11/2008 | McCormick et al. |
| 2008/0283426 A1 | 11/2008 | Primer et al. |
| 2008/0283433 A1 | 11/2008 | Primer |
| 2009/0026146 A1 | 1/2009 | Carlisle et al. |
| 2009/0076461 A1 | 3/2009 | Susi et al. |
| 2009/0184026 A1 | 7/2009 | Massengale et al. |
| 2009/0194453 A1 | 8/2009 | Thorne, Jr. et al. |
| 2009/0208368 A1 | 8/2009 | Waldrep et al. |
| 2009/0234346 A1 | 9/2009 | McBride, Jr. et al. |
| 2009/0236259 A1 | 9/2009 | Hicks |
| 2010/0274205 A1 | 10/2010 | Morelli et al. |
| 2010/0307941 A1* | 12/2010 | Tomes .................. A61B 50/33 |
| | | 206/370 |
| 2010/0307942 A1 | 12/2010 | Tomes et al. |
| 2010/0311026 A1 | 12/2010 | Tomes et al. |
| 2011/0107494 A1 | 5/2011 | Haines |
| 2011/0120906 A1 | 5/2011 | Umholtz et al. |
| 2011/0155599 A1 | 6/2011 | Yakel et al. |
| 2011/0203957 A1 | 8/2011 | Zoland et al. |
| 2011/0232234 A1* | 9/2011 | Lockwood ............. A61B 50/30 |
| | | 53/443 |
| 2011/0233079 A1* | 9/2011 | Macinnes ............. A61M 5/002 |
| | | 283/106 |
| 2011/0284410 A1* | 11/2011 | Lockwood ......... B65D 21/0202 |
| | | 206/364 |
| 2011/0290260 A1 | 12/2011 | Tomes et al. |
| 2011/0290262 A1 | 12/2011 | Tomes et al. |
| 2011/0297147 A1 | 12/2011 | Lick et al. |
| 2012/0145589 A1 | 6/2012 | MacInnes et al. |
| 2012/0150123 A1 | 6/2012 | Lawrence et al. |
| 2012/0222686 A1 | 9/2012 | Lockwood et al. |
| 2012/0271161 A1 | 10/2012 | Buckberry |
| 2012/0298114 A1 | 11/2012 | Landsman et al. |
| 2013/0037440 A1 | 2/2013 | Danchisin et al. |
| 2013/0042576 A1 | 2/2013 | Sweeney |
| 2013/0245496 A1 | 9/2013 | Wells et al. |
| 2013/0269713 A1 | 10/2013 | Bui et al. |
| 2013/0277248 A1 | 10/2013 | Tomes et al. |
| 2013/0277262 A1 | 10/2013 | Nemard |
| 2014/0021087 A1 | 1/2014 | Adler et al. |
| 2014/0039349 A1 | 2/2014 | Moghe et al. |
| 2014/0100551 A1 | 4/2014 | Holmstrom |
| 2014/0142465 A1 | 5/2014 | Tomes et al. |
| 2014/0231287 A1 | 8/2014 | Tomes et al. |
| 2014/0231288 A1 | 8/2014 | Tomes et al. |
| 2014/0262851 A1 | 9/2014 | Adler et al. |
| 2014/0263595 A1 | 9/2014 | Pantelleria |
| 2015/0048103 A1 | 2/2015 | Danchisin et al. |
| 2015/0083627 A1 | 3/2015 | Gorman |
| 2015/0151017 A1 | 6/2015 | Tipton et al. |
| 2015/0258304 A1 | 9/2015 | Tomes et al. |
| 2015/0283354 A1 | 10/2015 | Olson et al. |
| 2015/0335855 A1 | 11/2015 | Tomes et al. |
| 2016/0166800 A1 | 6/2016 | Tomes et al. |
| 2016/0193444 A1 | 7/2016 | Tomes et al. |
| 2016/0228676 A1 | 8/2016 | Glithero et al. |
| 2016/0243332 A1 | 8/2016 | Portela et al. |
| 2017/0056122 A1* | 3/2017 | Ramsey .................. A61B 90/94 |
| 2017/0056125 A1 | 3/2017 | Garza et al. |
| 2017/0086746 A1 | 3/2017 | Ofek et al. |
| 2017/0106165 A1 | 4/2017 | Holmes |
| 2017/0202699 A1 | 7/2017 | Zani et al. |
| 2017/0216557 A1 | 8/2017 | Kearns et al. |
| 2017/0216558 A1 | 8/2017 | Hughett et al. |
| 2017/0231804 A1 | 8/2017 | Miller et al. |
| 2017/0232226 A1 | 8/2017 | Loui et al. |
| 2017/0296282 A1 | 10/2017 | Turturro et al. |
| 2017/0296283 A1 | 10/2017 | Turturro et al. |
| 2017/0296284 A1* | 10/2017 | Turturro .................. B65D 65/02 |
| 2017/0319183 A1 | 11/2017 | Tomes et al. |
| 2017/0349305 A1 | 12/2017 | Tomes et al. |
| 2017/0368302 A1 | 12/2017 | Brooks et al. |
| 2018/0001052 A1 | 1/2018 | Lockwood et al. |
| 2018/0056030 A1 | 3/2018 | Tomes et al. |
| 2018/0057196 A1 | 3/2018 | Tomes et al. |
| 2018/0206933 A1* | 7/2018 | Healey .................. A61B 50/22 |
| 2018/0221564 A1 | 8/2018 | Patel et al. |
| 2019/0151195 A1 | 5/2019 | Tomes et al. |
| 2020/0360103 A1 | 11/2020 | Knapp et al. |
| 2021/0100978 A1 | 4/2021 | Gohde |
| 2021/0196922 A1 | 7/2021 | Hughett, Sr. |

FOREIGN PATENT DOCUMENTS

| | | |
|---|---|---|
| DE | 102007003223 B4 | 12/2009 |
| EP | 1301782 A1 | 4/2003 |
| EP | 1595561 A2 | 11/2005 |
| EP | 1731189 A1 | 12/2006 |
| FR | 2780274 A1 | 12/1999 |
| FR | 2873929 A1 | 2/2006 |
| GB | 2365342 A | 2/2002 |
| JP | S50-149175 A | 11/1975 |
| JP | 2002-136597 A | 5/2002 |
| JP | 2005-506110 A | 3/2005 |
| JP | 2007-229520 A | 9/2007 |
| JP | 2007-319535 A | 12/2007 |
| JP | 2010-200809 A | 9/2010 |
| JP | 2011-520578 A | 7/2011 |
| WO | 9106255 A1 | 5/1991 |
| WO | 9607364 A1 | 3/1996 |
| WO | 02/004942 A1 | 1/2002 |
| WO | 02064078 A1 | 8/2002 |
| WO | 2002083021 A1 | 10/2002 |
| WO | 2004005157 A1 | 1/2004 |
| WO | 2005027767 A1 | 3/2005 |
| WO | 2006114466 A1 | 11/2006 |
| WO | 2007/045943 A1 | 4/2007 |
| WO | 08033873 A2 | 3/2008 |
| WO | 2008139852 A1 | 11/2008 |
| WO | 2015057999 | 4/2015 |
| WO | 2017147067 A1 | 8/2017 |
| WO | 2018044772 A1 | 3/2018 |
| WO | 2018057835 A1 | 3/2018 |
| WO | 2018183752 A1 | 10/2018 |
| WO | 2018190865 A1 | 10/2018 |

(56) References Cited

FOREIGN PATENT DOCUMENTS

| WO | 2019/209867 A1 | 10/2019 |
|---|---|---|
| WO | 2019246307 A1 | 12/2019 |
| WO | 2021/081434 A1 | 4/2021 |

OTHER PUBLICATIONS

"Uniting the best of Healthcare" http://ghx.com/about/, last accessed 2019.
Addison, R. et al., "Catheter Care," Royal College of Nursing, London (2008).
American Journal of Infection Control. vol. 46 (2018) SI6-67.
Arrow, "Arrow Trauma Products" brochure, 2000.
AU 2014337176 filed Mar. 15, 2016 Examination Report dated Aug. 1, 2018.
Bardex I.C. Complete Care StateLock Device 350 ml Urine Meter Foley Tray with Bacteriostatic Collection System, Directions for Use; Dated 2006.
Bardex I.C. Infection Control 350 ml Urine Meter Foley Tray, Directions for Use; Dated 2006.
Bardex I.C. Infection Control Foley Tray, Directions for Use; Dated 2006.
C. R. Bard Urological Drainage, https://www.crbard.com/medical/Professionals/Product-Concentrations/Urological-Drainage, last accessed 2019.
C.R. Bard, Inc; "A few important words about Catheter Care"; Dated 2001.
California Department of Public Health, "Catheter-Associated Urinary Tract Infection (CAUTI) Prevention" (2015).
CN 201480057141.5 filed Apr. 18, 2016 Office Action dated Dec. 4, 2018.
Dept. of Health and Human Services, "Action Plan to Prevent Healthcare-Associated Infections." (2009).
Dobkin et al., "Myth and Measurement—The Case of Medical Bankruptcies," 378 New Eng. J. Med., 1076-78 (2018).
Ellen Elpern, et al., "Prevention of Catheter-Associated Urinary Tract Infections in Adults," 36 Critical Care Nurse, 9(2016).
EP 14853869.7 filed Mar. 31, 2016 Extended European Search Report dated Aug. 4, 2017.
EP 14853869.7 filed Mar. 31, 2016 Office Action dated Mar. 13, 2019.
Foxman, B. "Epidemiology of Urinary Tract Infections: Incidence, Morbidity, and Economic Costs." The American Journal of Medicine, 113 Suppl 1A (2002).
Gould et al., "Catheter-associated Urinary Tract Infection (CAUTI) Toolkit," Centers for Disease Control and Prevention Devision of Healthcare Quality Promotion. (2009).
Gould et al., "Guideline for Prevention of Catheter Associated Urinary Tract Infections," Centers for Disease Control Healthcare Infection Control Practices Advisory Committee, (2009).
Greene, L. et al. "Guide to the Elimination of Catheter-Associated Urinary Tractinfections (CAUTIs): Developing and Applying Facility-Based Prevention Interventions in Acute and Long-Term Care Settings," Association for Professionals in Infection Control and Epidemiology, (2008).
Jacobsen, S.M. et al., "Complicated Catheter-Associated Urinary Tract Infections Due to *Escherichia coli* and *Proteus mirabilis*", 21 Clinical Microbiology Reviews 1, 26-59 (Jan. 2008).
Jennifer A Meddings, "Implementing Strategies to Reduce Hospital-Acquired Catheter-Associated Urinary Tract Infection," Wound, Ostomy and Continence Nurses Society, www.catheterout.org, (Jun. 2010).
JP 2016-523921 filed Apr. 15, 2016 Office Action dated Jul. 11, 2018.
Linda Kohn et al., eds., "To Err is Human: Building a Safer Health System," Institute of Medicine (US), (2000).
Lo, E. et al., "Strategies to Prevent Catheter-Associated Urinary Tract Infections in Acute Care Hospitals," Infection Control and Hospital Epidemiology. 29, S41-S50 (2008).
Madeo M. et al., "Reducing the risks associated with urinary catheters." Nursing Standard, vol. 23, No. 29, 47-55 (2009).
Male Catheter Insertion Video, Uploaded to YouTube on Feb. 7, 2008, Parts 1 and 2. https://www.youtube.com/watch?v=ISBAya_5cIM (Last accessed Feb. 26, 2020).
Norman, Donald A., The Design of Everyday Things, 2002 ed. (Excerpt).
Ortega, R. et al. "Female Urethral Catheterization", N Engl J Med 2008; 358: e15. Apr. 3, 2008.
PCT/US14/60963 filed Oct. 16, 2014 International Search Report and Written Opinion dated Jan. 14, 2015.
PCT/US2017/027628 filed Apr. 14, 2017 International Search Report and Written Opinion dated Jul. 17, 2017.
PCT/US2018/025260 filed Mar. 29, 2018 International Search Report and Written Opinion dated Jun. 7, 2018.
Request for Inter partes Review of U.S. Pat. No. 8,631,935, filed Dec. 30, 2014.
Saint et al., "Catheter-Associated Urinary Tract Infection and the Medicare Rule Changes," Annals of Internal Medicine, Jun. 16, 2009.
Steultjens, M.P.M. et al., "Range of joint motion and disability in patients with osteoarthritis of the knee or hip," Rheumatology, Bristish Society for Rheumatology. (2000).
The Joint Commision on National Patient Safety, "2012 National Patient Safety Goals: Hospital accreditation Program." (2012).
Thomson et. al. "Male Urethral Catheterization", N Engl J Med 2006; 354: e22. May 25, 2006.
Urological Drainage website, http://m.bardmedical.com/products/urological-drainage/, last accessed 2019.
U.S. Appl. No. 15/029,613, filed Apr. 14, 2016 Final Office Action dated Apr. 10, 2019.
U.S. Appl. No. 15/029,613, filed Apr. 14, 2016 Non-Final Office Action dated Nov. 29, 2018.
U.S. Appl. No. 15/487,297, filed Apr. 13, 2017 Advisory Action dated Apr. 28, 2020.
U.S. Appl. No. 15/487,297, filed Apr. 13, 2017 Final Office Action dated Feb. 21, 2020.
U.S. Appl. No. 15/487,297, filed Apr. 13, 2017 Non-Final Office Action dated Apr. 5, 2019.
U.S. Appl. No. 15/487,297, filed Apr. 13, 2017 Restriction Requirement dated Jun. 11, 2020.
U.S. Appl. No. 15/487,297, filed Apr. 13, 2017 Restriction Requirement dated Nov. 29, 2018.
U.S. Appl. No. 16/639,059, filed Feb. 13, 2020 Non-Final Office Action dated Feb. 8, 2022.
U.S. Appl. No. 16/639,059, filed Feb. 13, 2020 Restriction Requirement dated Oct. 13, 2021.
PCT/US2019/038051 filed Jun. 19, 2019 International Prelliminary Report on Patentability dated Dec. 22, 2020.
PCT/US2019/038051 filed Jun. 19, 2019 International Search Report and Written Opinion dated Aug. 29, 2019.
Raheem, "Application of Plastics and Paper as Food Packaging Materials" An Overview, 2017, Emirates Journal of Food and Agriculture,vol. 25, pp. 177-188 (Year: 2017).
U.S. Appl. No. 16/497,770, filed Sep. 25, 2019 Non-Final Office Action dated Jun. 1, 2022.
U.S. Appl. No. 16/639,059, filed Feb. 13, 2020 Notice of Allowance dated Jul. 1, 2022.
U.S. Appl. No. 17/058,067, filed Nov. 23, 2020 Non-Final Office Action dated Jul. 7, 2022.
PCT/US20/35371 filed May 29, 2020 International Search Report and Written Opinion dated Sep. 14, 2020.
U.S. Appl. No. 15/487,297, filed Apr. 13, 2017 Notice of Allowance dated Oct. 2, 2020.

\* cited by examiner

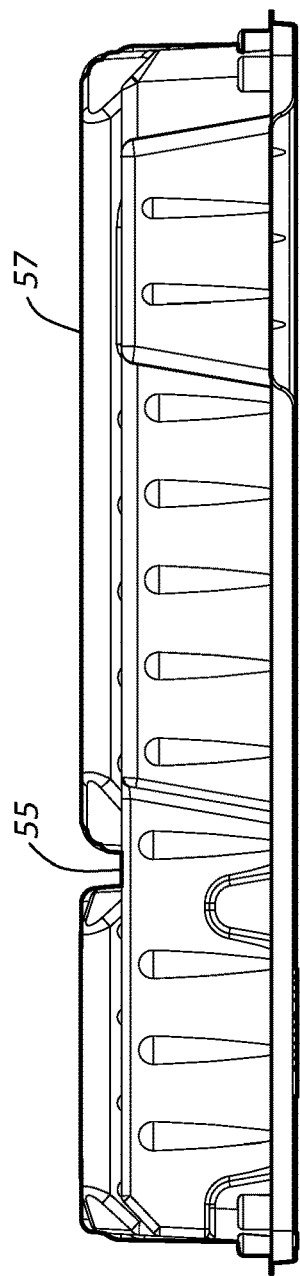
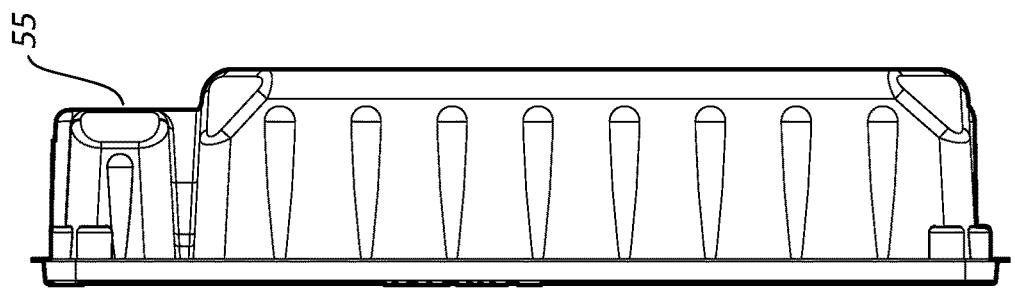

Directions for Use and Patient Education Information

Proper Techniques for Urinary Catheter Insertion

- Perform hand hygiene immediately before and after insertion
- Insert urinary catheters using aseptic technique and sterile equipment
- Use the smallest Foley catheter possible, consistent with good drainage
- Document the indications for catheter insertion, date and time of catheter insertion, individual who inserted catheter, and date and time of catheter removal in patient record

Proper Techniques for Urinary Catheter Maintenance

- Secure the Foley Catheter, use the STATLOCK® Foley Stabilization Device if provided
- Maintain a closed drainage system by utilizing pre-connected, sealed catheter-tubing junctions
- Maintain unobstructed urine flow and keep the catheter and collection tube free from kinking
- Keep the collection bag below the level of the bladder or hips at all times
- Empty the collection bag regularly (e.g., prior to transport) using a separate, clean collection container for each patient
- Routine hygiene (e.g., cleansing of the meatal surface during daily bathing or showering) is appropriate
- Leave Foley catheter in place only as long as needed

MEDICAL

*FIG. 14A*

EZ-LOK® SAMPLING PORT

Sterile contents of inner wrap are sterile unless package has been opened or damaged.

Caution: (U.S.A.) law restricts this device to sale by or on the order of a physician.

Single Use Only.
Do not resterilize.
For urological use only.

Warning: Catheter, do not use ointments or lubricants having a petrolatum base. They will damage the catheter and may cause balloon to burst.

Warning: this product may be a potential biohazard. Handle and dispose of in accordance with accepted medical practices and applicable local, state and federal laws and regulations.

Visually inspect the product for any imperfections or surface deterioration prior to use. If package is opened or if any imperfection or surface deterioration is observed, do not use.

Please consult product label and insert for any indications, contraindications, hazards, warnings, cautions and directions for use.

Bard, EZ-Lok and StatLock are trademarks and/or registered trademarks of C. R. Bard, Inc.

©2013 C. R. Bard, Inc. All Rights Reserved.
Manufactured in USA.
PK7635865   10/2013

Bard® EZ-Lok® Sampling Port (indicated by the blue stem in the port) accepts Luer lock (Fig. 1a) or slip tip syringes (Fig. 1b).

1. Occlude drainage tubing a minimum of 3 inches below the sampling port by kinking the tubing until urine is visible under the access site.

2. Swab surface of Bard® EZ-Lok® Sampling Port with antiseptic wipe. (Fig. 2)

3. Using aseptic technique, position the syringe in the center of the sampling port. Press the syringe firmly and twist gently to access the sampling port. (Fig. 3)

4. Slowly aspirate urine sample into syringe and remove syringe from sample port.

5. Unkink tubing if necessary and transfer urine specimen into specimen cup or follow hospital protocol. Discard syringe according to hospital protocol.

6. Follow established hospital protocol for specimen labeling and transport to lab.

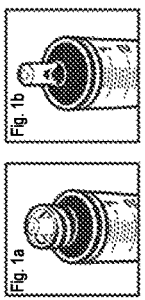
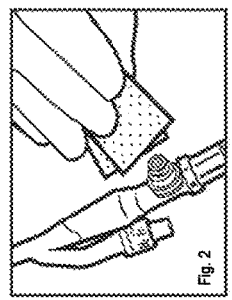
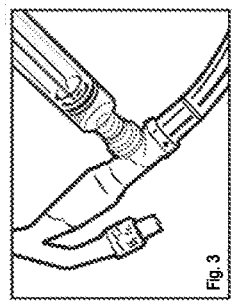

*FIG. 14D*

PATIENT/FAMILY EDUCATION

Your Foley Catheter

A urinary catheter is a thin tube placed in the bladder to drain urine. The urine drains through a tube into the collection bag. If you have a urinary catheter, it is possible for germs to travel along the catheter and cause an infection in your bladder or your kidney; in that case it is called a catheter-associated urinary tract infection (or CA-UTI).

*How can I take every precaution to prevent catheter-associated urinary tract infections?*

- Ask your healthcare provider each day if you still need your catheter
- Make sure your catheter tubing is secured to your leg or abdomen if possible
- Make sure all hospital staff wash or sanitize their hands before & after touching your catheter
- Do not tug, pull or twist the catheter tubing
- Always keep your urine drain bag below the level of your bladder or hips and off the floor
- Avoid disconnecting the catheter from the drain tube

*FIG. 15A*

EDUCACIÓN DEL PACIENTE/FAMILIAR

Su sonda Foley

Una sonda o catéter urinario consiste en un tubo delgado que se coloca en la vejiga para drenar la orina. La orina se drena por medio de un tubo y se recoge en una bolsa. Si lleva una sonda urinaria, los gérmenes pueden desplazarse por el catéter y causar una infección en la vejiga o el riñón; en tal caso, se produciría una infección del tracto urinario asociada a catéter urinario (o ITU-CU).

*¿Cómo puede prevenir las infecciones del tracto urinario asociadas a catéter urinario?*

Pregunte todos los días a su médico si debe seguir llevando la sonda.

Asegúrese de que el tubo de la sonda esté fijado a la pierna o al abdomen si es posible.

Asegúrese de que todo el personal del hospital se limpie o esterilice las manos antes y después de tocar la sonda.

No doble, tire ni estire del tubo d la sonda.

Mantenga siempre la bolsa de drenaje urinario por debajo del nivel de la vejiga o la cadera y por encima del suelo.

Evite desconectar la sonda del tubo de drenaje.

*FIG. 15B*

CATHETER INSERTION TRAY WITH INTEGRATED INSTRUCTIONS

PRIORITY

This application is a division of U.S. patent application Ser. No. 15/029,613, which is a U.S. national stage application under 35 U. S.C. § 371 of International Application No. PCT/US2014/060963, filed Oct. 16, 2014, now U.S. Pat. No. 10,758,705, which claims the benefit of U.S. Provisional Application No. 61/891,496, filed Oct. 16, 2013, and of U.S. Provisional Application No. 62/015,206, filed Jun. 20, 2014, each of which is incorporated by reference in its entirety into this application.

BACKGROUND

Urinary drainage systems are conventionally used in hospitals and health care facilities when it is necessary to facilitate, control, monitor urination of patients, and when it is necessary to collect urine from a patient. These urinary drainage systems permit the patient to remain in bed, without having to use a bedpan or be moved to use a bathroom. Urinary drainage systems may include a catheter (e.g., a Foley catheter), a collection container/bag (e.g., a bag made of a polymeric material or PVC film), a urine meter, tubing connecting the Foley catheter to the collection container/bag or urine meter, and/or other equipment. In operation, the patient is first catheterized, and the catheter is connected to the drainage container/bag and/or urine meter through a length of tubing (e.g., drainage tubing). The urine drains through the catheter, the tubing, and then finally into the collection container/bag and/or urine meter. The urine may be moved from the catheter into the collection bag solely due to gravitational forces. On average, a patient produces about 80-90 mL of urine in 1 hour.

Accurate monitoring of urine helps the clinician detect irregularities in urine flow rate or volume that can signal to the clinician that the patient is suffering certain problems. However, urine output cannot be accurately measured if the drainage system attached to the Foley catheter is not reliable, or if the Foley catheter and drainage system are not properly used. Further, hospitals are using increasingly lower-profile beds in order to reduce the number of injuries sustained from falls. With the adoption of lower profile beds, the amount of height available to allow the tubing to drain is decreased. Drainage tubing used in hospitals and associated venting systems have also undergone changes/revisions. Changes in venting combined with increasingly lower profile hospital beds have created suboptimal drainage performance. For example, urine has been observed pooling in the tubing. This prevents accurate urine output and flow rate measurements, which are critical for many patients.

Currently, the second-most common form of Hospital Acquired Infection (HAI) is catheter-associated urinary tract infection (CAUTI). Hospitals are interested in ways to cut their CAUTI rates by conforming to a strict aseptic technique as a standard of care. However, there are many factors that influence a hospital's ability to meet the standard of care. These factors include: health care practitioner/nurse experience and training, patient factors (e.g., general health, weight, and anatomy), environmental factors, and tray layout as well as contents and instructions/indicators. A catheterization package and/or catheterization tray with components optimized to the procedure and an intuitive layout can increase compliance to aseptic technique, potentially reducing CAUTI rates.

There is a need in the healthcare field for a more reliable, safe, and easy method for inserting a catheter, such as a urinary catheter, for example an indwelling or intermittent catheter, into a patient. More particularly, there is a need to provide a catheterization package and/or a catheterization tray (e.g., a Foley catheter tray) that improves and standardizes the process for inserting a urinary catheter, such as an indwelling Foley catheter, into a patient.

The present disclosure provides a catheterization package, catheter tray, and drainage system configured to better meet patients' needs, improve reliability and ease of use, reduce incidents of CAUTI, improve safety, and address other issues described above and elsewhere herein.

SUMMARY

Embodiments of, and enhancements for, packages, systems, trays, assemblies, devices, methods, etc. used for medical treatment generally and catheterization, in particular, are described herein.

The objectives described herein can be met by providing an improved medical procedure package and/or tray (e.g., an improved catheterization package and/or an improved catheterization tray). The improved medical procedure package may include the improved medical procedure tray therein, and the medical procedure tray may be intuitively arranged and may include instructions or procedural indicators to improve the medical procedure implementation and results. The medical procedure package and/or medical procedure tray may include various implements and components necessary and/or helpful to the medical procedure. For example, an improved catheterization package may include an improved catheterization tray, povidone iodine swabs or swabsticks that allow for greater coverage and saturation, hand sanitizer with improved efficacy and that enables single-handed usage, tubing that breaks up the surface tension of the fluid in order to improve drainage, and/or other components described herein.

According to various embodiments, the present disclosure provides a catheterization package and catheterization tray having a layout and/or arrangement of components that may help reduce CAUTI rates by facilitating ease of use and aiding in proper aseptic technique during insertion. The present disclosure also provides methods of catheterization and use of a catheterization package and/or catheterization tray that may facilitate easier and more sterile catheterization to help reduce CAUTI rates. Further, the present disclosure provides a system that may improve drainage performance, which in turn: (1) helps to eliminate fluid in the drain tubing, and (2) increases the accuracy of urine measurements (e.g., measurements of output and flow).

In one embodiment, a catheterization package comprises a catheterization tray including a first compartment holding a drainage system; a second compartment holding a syringe; a third compartment holding a swab in an inclined position such that an absorbent head of the swab is biased downwardly into a well of the third compartment and an elongate member of the swab angles upwardly for easier gripping and removal; and catheterization instructions or procedural indicators imprinted directly on the catheterization tray. The catheterization package may also include a sterile wrap (e.g., a CSR wrap) wrapped around the catheterization tray. The absorbent head of the swab may be formed of absorbent foam, and the elongate member of the swab may have a generally rectangular cross section with rounded edges. The catheterization package may also include a peri-care kit packaged with the catheterization tray at a location outside the sterile wrap. The catheterization package may also include a belly band outside the sterile wrap, the belly band including an instruction or procedural indicator regarding how to orient the catheterization tray prior to opening the sterile wrap. Additionally, the catheterization package may include a packaging label outside the sterile wrap, wherein the packaging label includes at least three sides folded into a different plane from the top portion of the label that are visible when viewing the catheterization package from one or more sides of the catheterization package, and/or wherein the packaging label includes information features (e.g., information squares) that each emphasize a key feature of the catheterization package in a way that is easy to read quickly. The catheterization package may include an outer sealed container or bag (e.g., a plastic, transparent bag) around the other components to maintain sterility during shipping and storage.

In one embodiment, a medical procedure package comprises three or more compartments holding implements useful for performance of the medical procedure and instructions/procedural indicators imprinted or included directly on the medical procedure tray directing a user how to carry out steps of the medical procedure, wherein the three or more compartments of the medical procedure tray, the instructions/procedural indicators, and implements are arranged in an arrangement such that the medical procedure proceeds intuitively from step to step based on the arrangement. The arrangement may include stacking various components or implements (e.g., 2 to 20 implements/components or 4 to 10 implements/components) on top of each other in the order that they are to be used (e.g., with components or implements to be used before other components or implements being positioned on top of the other components or implements to be used later).

In one embodiment, a method of treating a patient comprises providing a medical procedure tray including three or more compartments including implements useful for performance of the medical procedure and instructions/procedural indicators imprinted directly on the medical procedure tray directing a user how to carry out steps of the medical procedure. The method may also include performing the medical procedure on a patient while following the instructions/procedural indicators imprinted on the medical procedure tray. Three or more compartments of the medical procedure tray, the instructions/procedural indicators, and/or implements are arranged such that the medical procedure proceeds intuitively from step to step based on how they are arranged on/in the medical procedure tray.

In one embodiment, a method of catheterizing a patient comprises providing a catheterization package having a catheterization tray including a first compartment holding a drainage system including a catheter; a second compartment holding a swab in an inclined position such that and absorbent head of the swab is biased downwardly into a well of the second compartment and an elongate member of the swab angles upwardly; pouring a sterilizing solution into the well such that the absorbent head is in contact with the sterilizing solution, using the swab to cleanse the patient in a region to be catheterized, and inserting a portion of a catheter into a urethra of the patient. A sealed container or bag may be disposed around the catheterization tray, and the method may include unsealing the sealed container or bag. A sterile wrap may be wrapped around the catheterization tray, and the method may include unwrapping the sterile wrap prior to pouring a sterilizing solution into the well. The catheterization package may also include a peri-care kit located outside of the sterile wrap, and the method may include using the peri-care kit to cleanse a portion of the patient's perineum prior to unwrapping the sterile wrap. A belly band may be positioned outside the sterile wrap, the belly band may include an instruction/procedural indicator or instructions/procedural indicators regarding how to properly orient the catheterization tray prior to opening the sterile wrap, and the method may include orienting the tray according to the instruction(s)/procedural indicator(s) prior to unwrapping the sterile wrap.

In one embodiment, a method of manufacturing a catheterization package comprises providing a catheterization tray including a first compartment, a second compartment, a third compartment having an inclined portion of the bottom of the compartment with channels for holding a swab, and catheterization instructions/procedural indicators imprinted directly on the catheterization tray; wherein the first compartment, the second compartment, and the third compartment are each at least partially separated from each other by walls/barriers. The method may also include positioning a drainage system in the first compartment, a syringe in the second compartment, and a swab in the third compartment such that an absorbent head of the swab is biased downwardly into a well of the third compartment and an elongate member of the swab angles upwardly for easier gripping and removal. The method may further include wrapping the catheterization tray in a sterile wrap and positioning a belly band around a portion of the sterile wrap, the belly band including an instruction/procedural indicator or instructions/procedural indicators regarding how to properly orient the catheterization tray prior to opening the sterile wrap. In addition, the method may include adding a peri-care kit to the catheterization tray outside the belly band and sterile wrap, the peri-care kit including a baggy with a zipper holding cleansing towelettes, hand sanitizer, and instructions/procedural indicators for cleansing the patient. The method may include adding a document of detailed catheterization instructions and/or procedural indicators to the catheterization package. Also, the method may include placing a packaging label on top of the catheterization package, the packaging label including at least three side portions folded from the top portion, and/or placing a packaging label on top of the catheterization package, the packaging label including an information feature or information features that each emphasize one or more key features of the catheterization package in a way that is easy to read quickly. The information feature or information features may be an information square or multiple information squares. The method may also include sealing (e.g., by heat sealing) a transparent plastic bag around the catheterization package.

In one embodiment, a catheterization system includes a container for securing components for a catheterization procedure. The container has an outer shell defining a general shape of the container and a plurality of compartments within the outer shell. Each of the plurality of compartments is separated from one or more adjacent compartments of the plurality of compartments by one or more separator/divider walls. The plurality of compartments include a first compartment sized and configured to contain a catheter assembly and one or more secondary compartments separated from the first compartment by the one or more separator/divider walls. At least one of the one or more secondary compartments includes at least one partial separator/divider wall (e.g., a separator/divider wall that includes a reduced height portion) of the one or more separator/divider walls.

In one embodiment, a catheterization system for performing a catheterization procedure is provided. The catheterization system includes a catheterization tray that has an outer shell defining a general shape of the container and a plurality of compartments within the outer shell. Each of the plurality of compartments is separated from one or more adjacent compartments of the plurality of compartments by one or more separator/divider walls. The plurality of compartments may include a first compartment containing a catheter assembly and one or more secondary compartments separated from the first compartment by the one or more separator/divider walls. At least one of the one or more secondary compartments may include at least one partial separator/divider wall (e.g., a separator/divider wall that includes a reduced height portion) of the one or more separator/divider walls. Additionally, the catheterization system includes one or more swabs located in a second compartment of the one or more secondary compartments.

BRIEF DESCRIPTION OF THE DRAWINGS

The disclosed packages, trays, devices, systems and methods can be better understood with reference to the following drawings. Portions of the material in this patent document are subject to copyright protection under the copyright laws of the United States and of other countries. The owner of the copyright rights has no objection to the facsimile reproduction by anyone of the patent document or the patent disclosure, as it appears in the United States patent and Trademark Office publicly available file or records, but otherwise reserves all copyright rights whatsoever.

FIG. 3 shows a right side elevation view of the exemplary medical procedure tray of FIG. 1.

FIG. 4 shows a back (or distal) side elevation view of the exemplary medical procedure tray of FIG. 1.

FIG. 14A shows a page of an exemplary document of detailed catheterization instructions/procedural indicators or directions for use (DFU) document that may be included in a catheterization package.

FIG. 14D shows another page of the exemplary document of detailed catheterization instructions/procedural indicators or directions for use (DFU) document of FIG. 14A.

FIG. 15A shows a front side of an exemplary patient education information sheet/pamphlet that may be included in a catheterization package.

FIG. 15B shows a back side of the exemplary patient education information sheet/pamphlet of FIG. 15A.

Figure 31A:
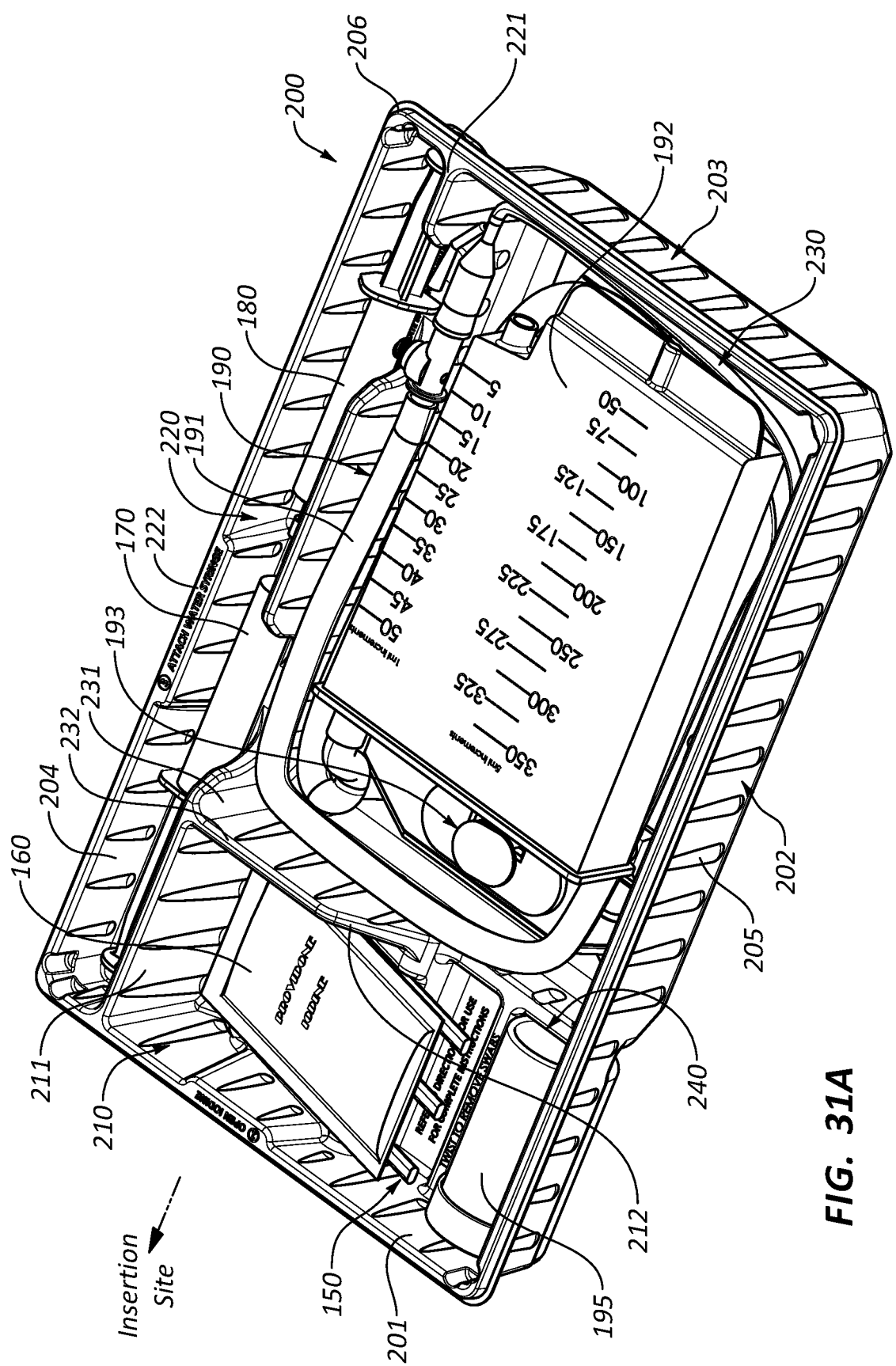
FIG. 31A is an isometric view of an exemplary catheterization tray with contents thereof.
Figure 32:
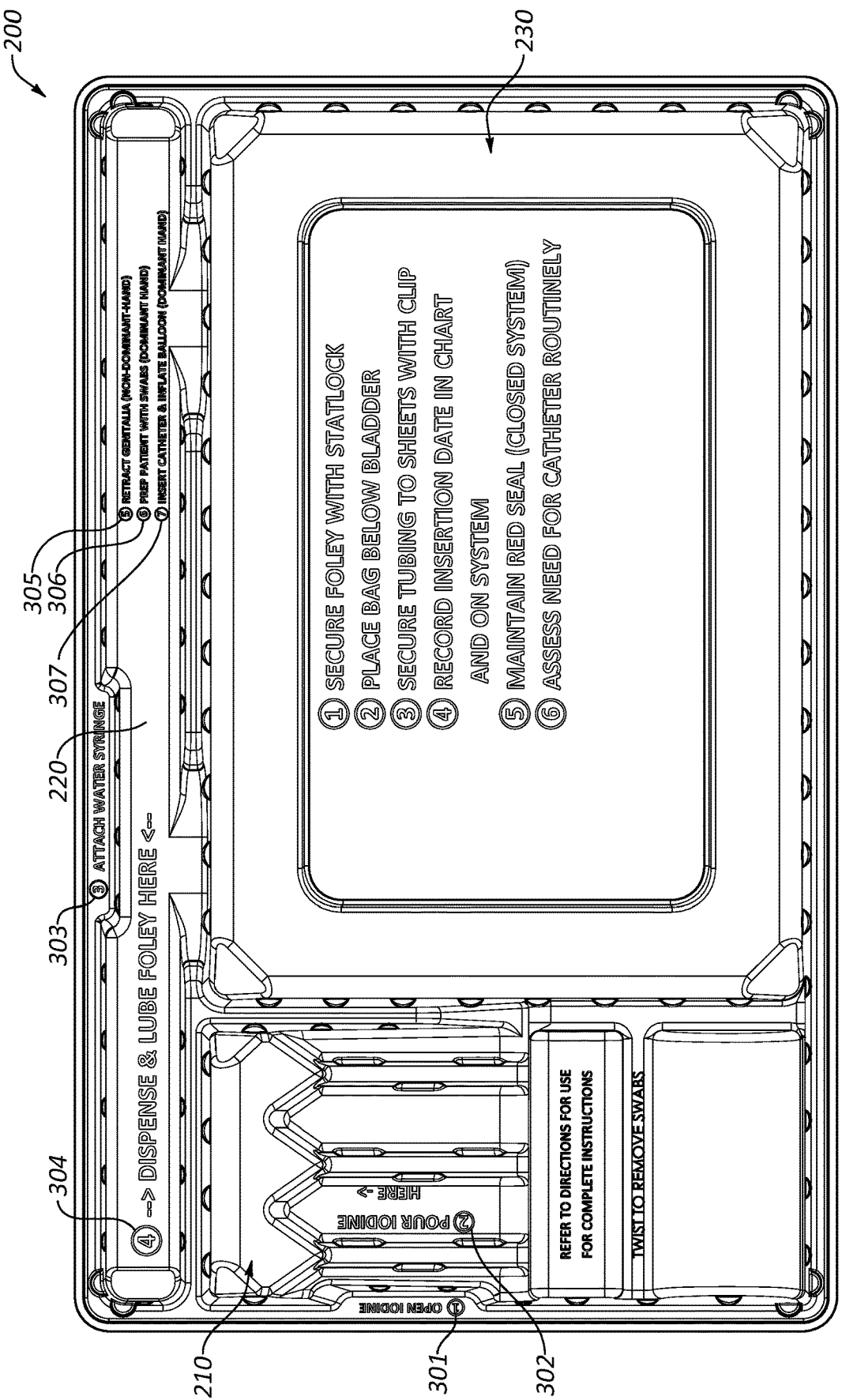
Figure 33:
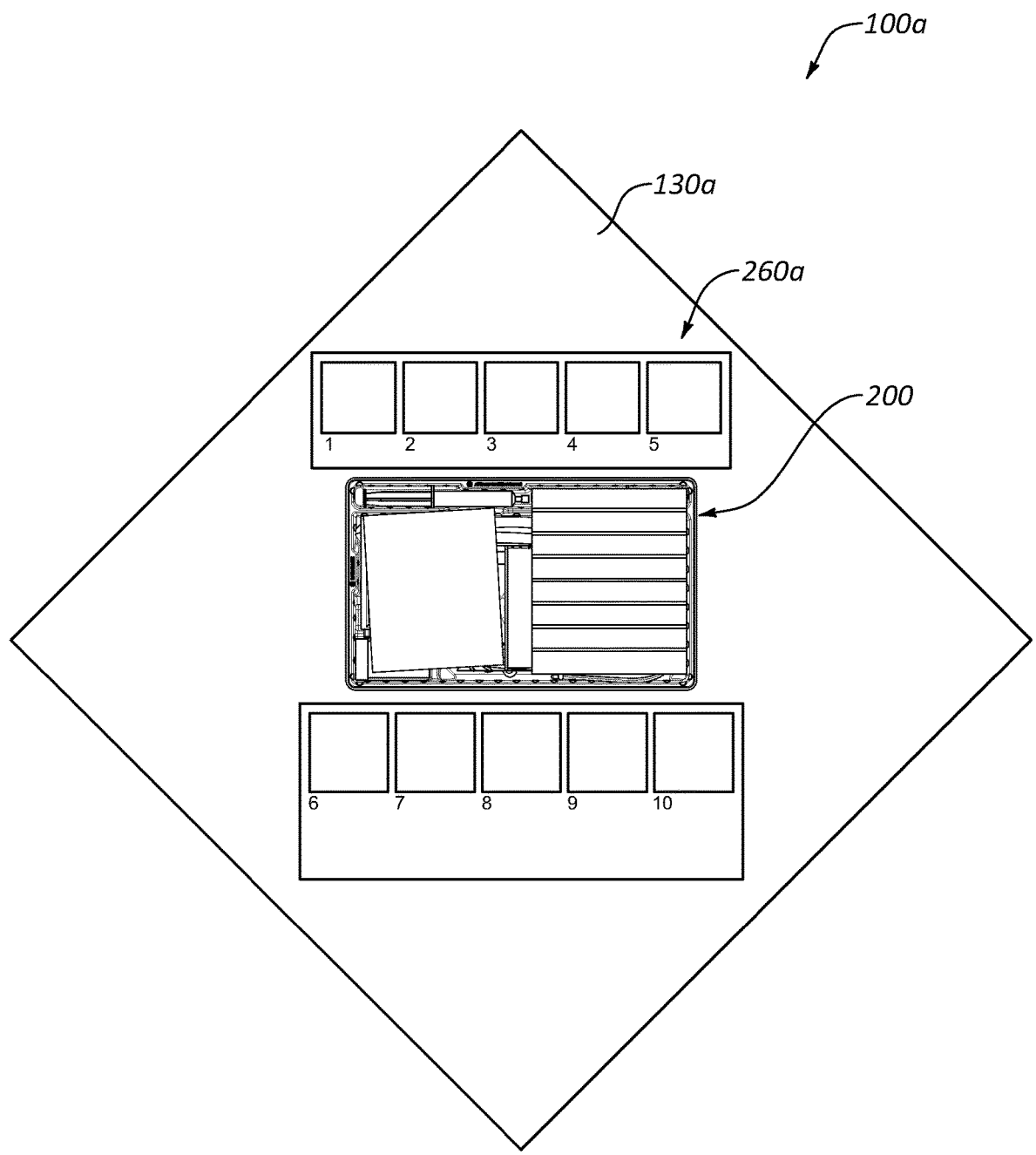
Figure 34:
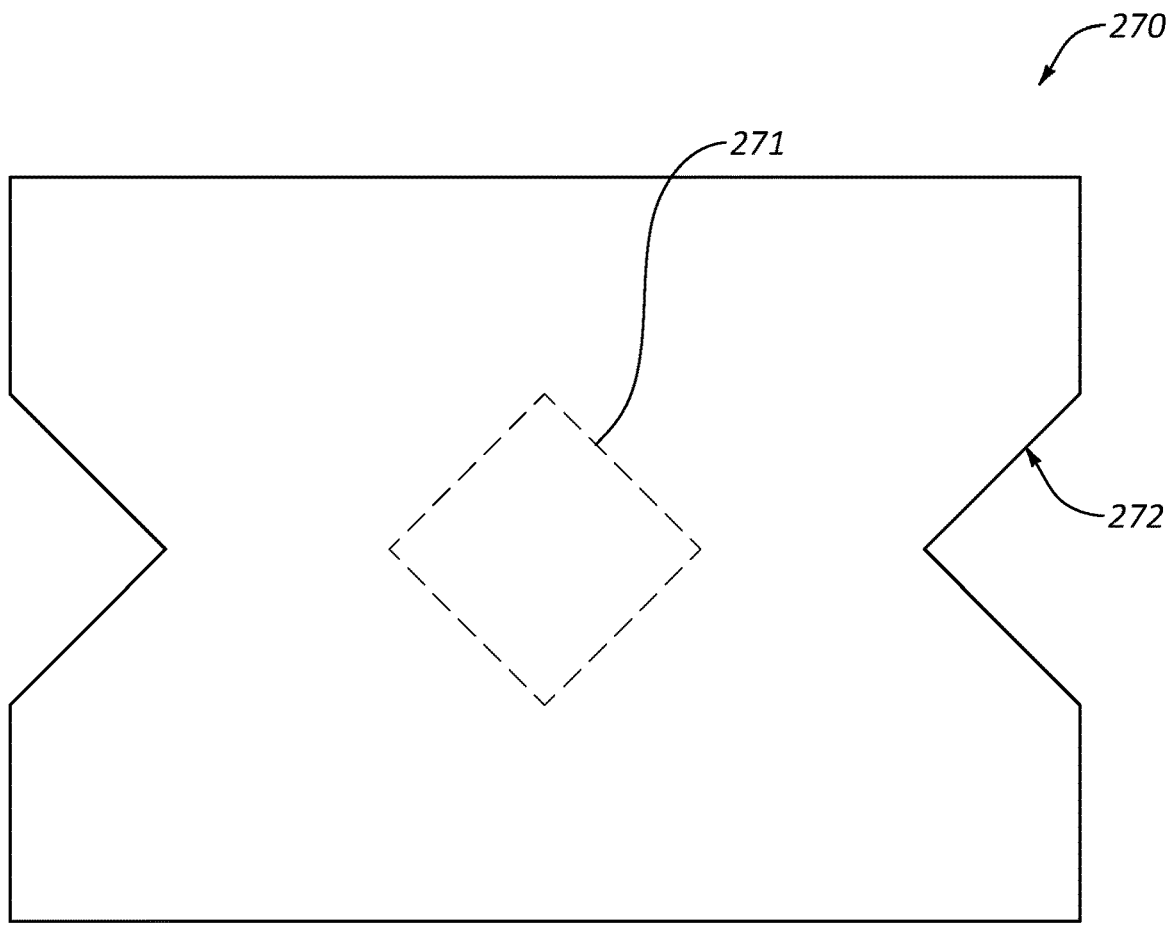
Figure 35:
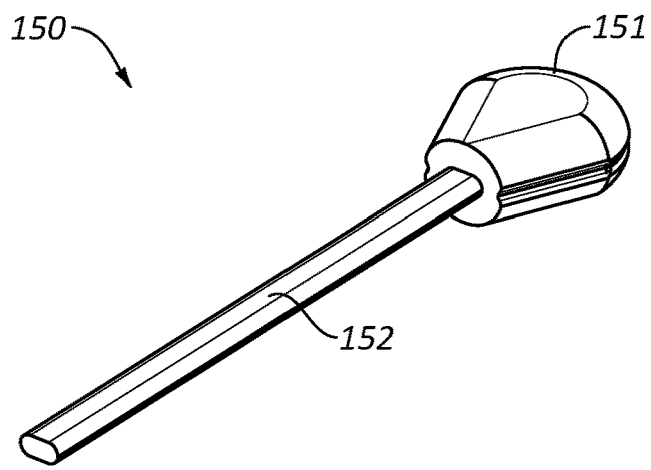
Figure 36A:
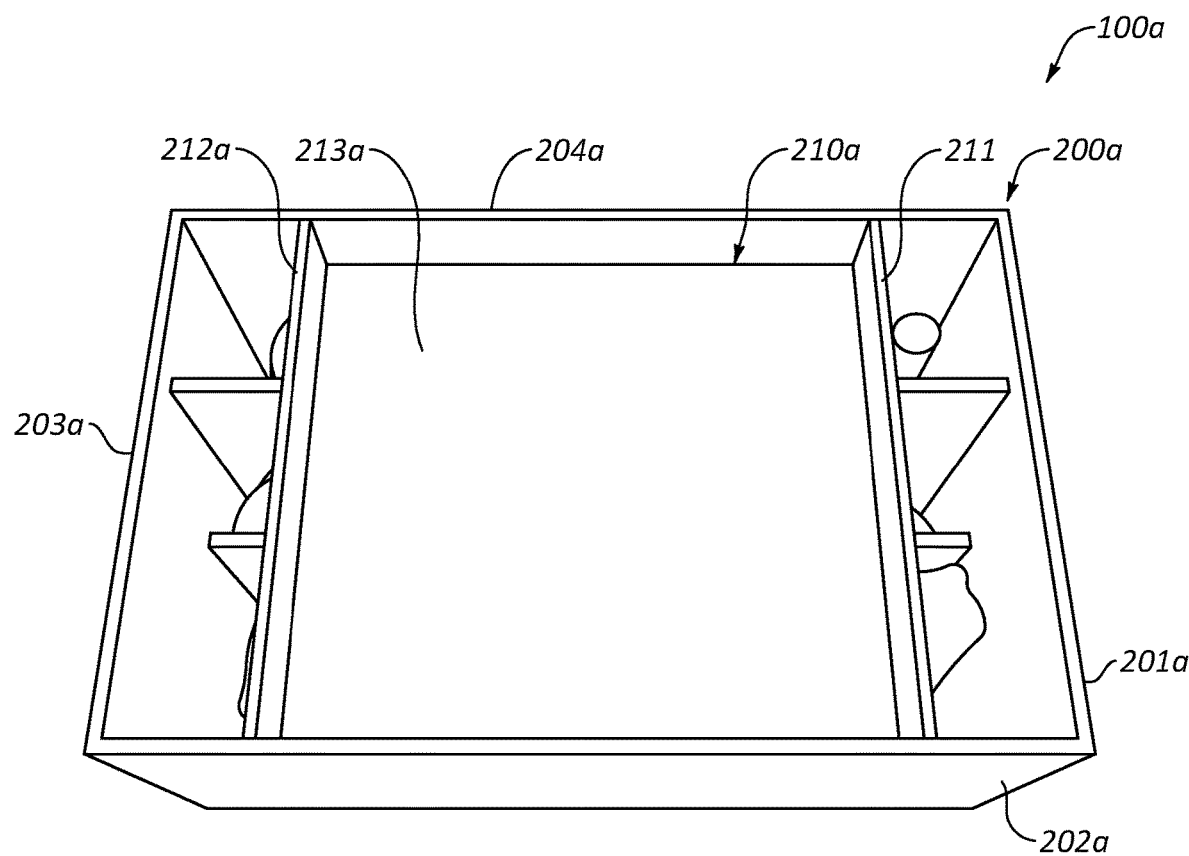
Figure 36B:
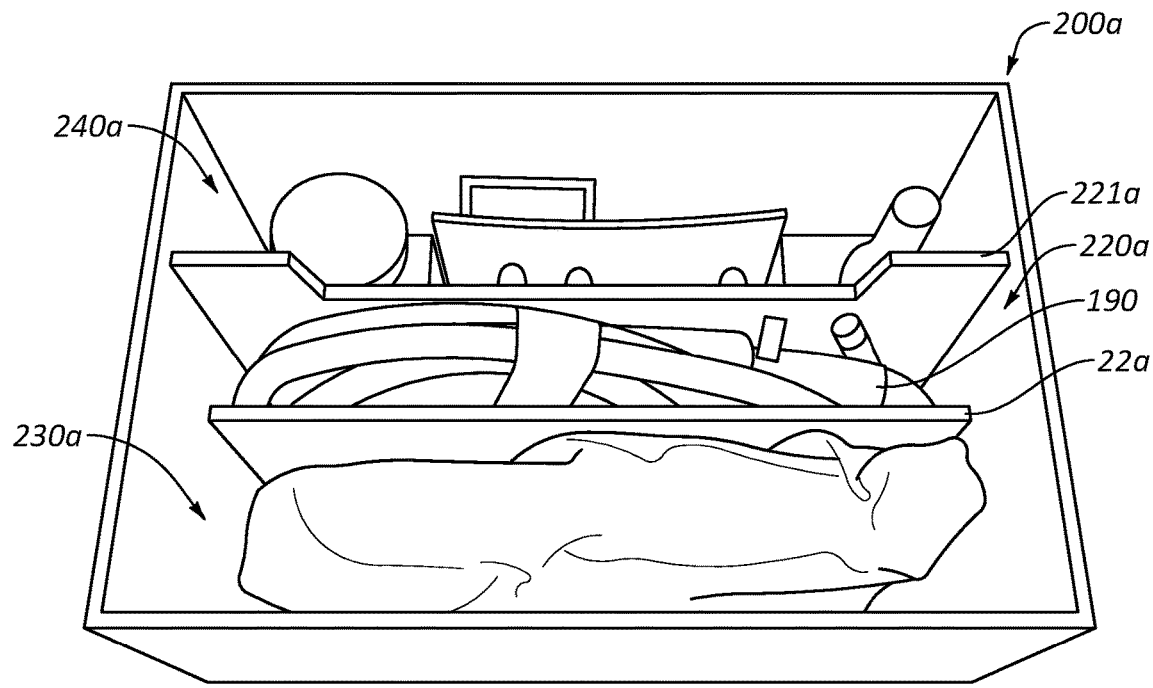
Figure 37A:
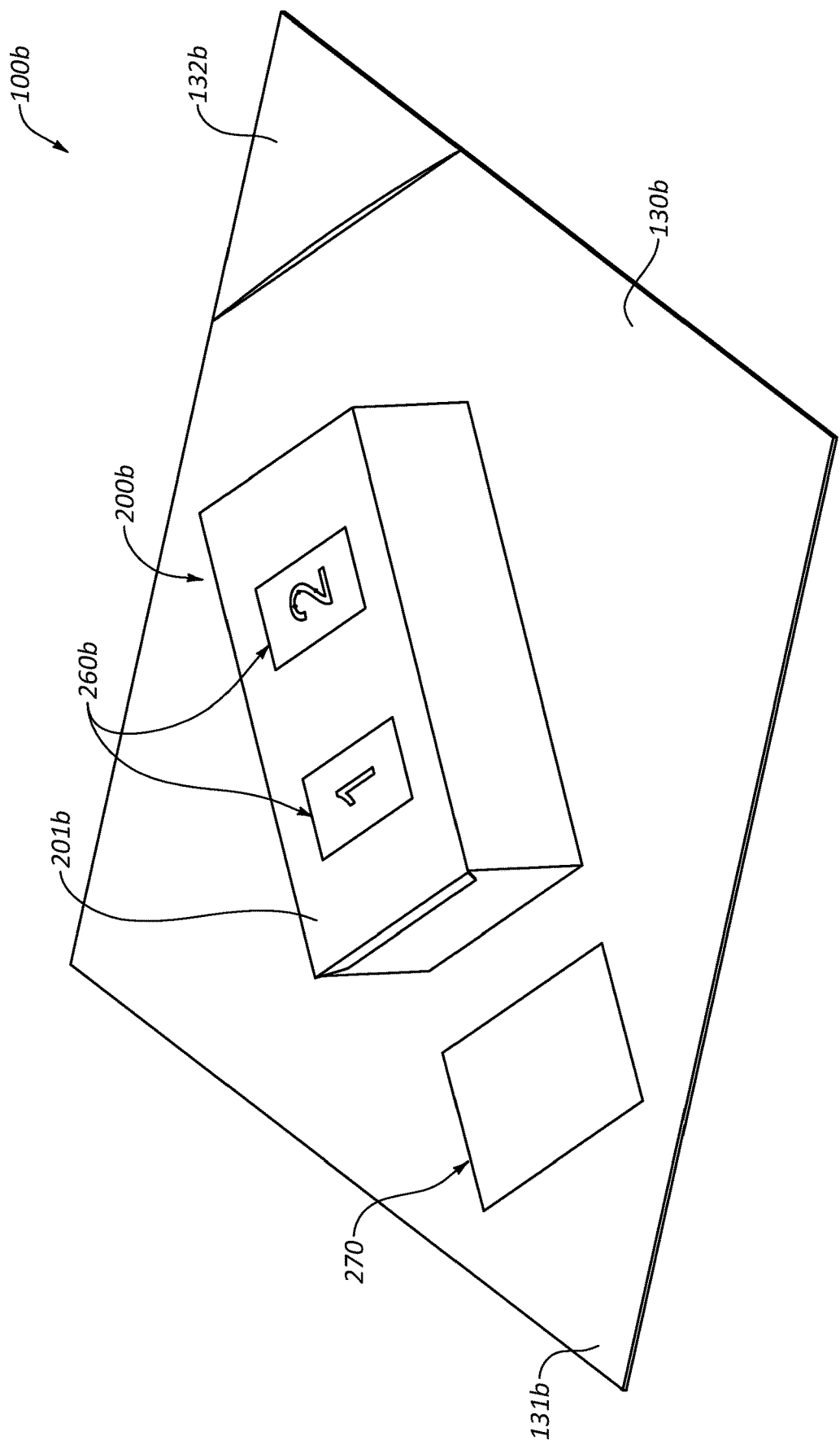
Figure 37B:
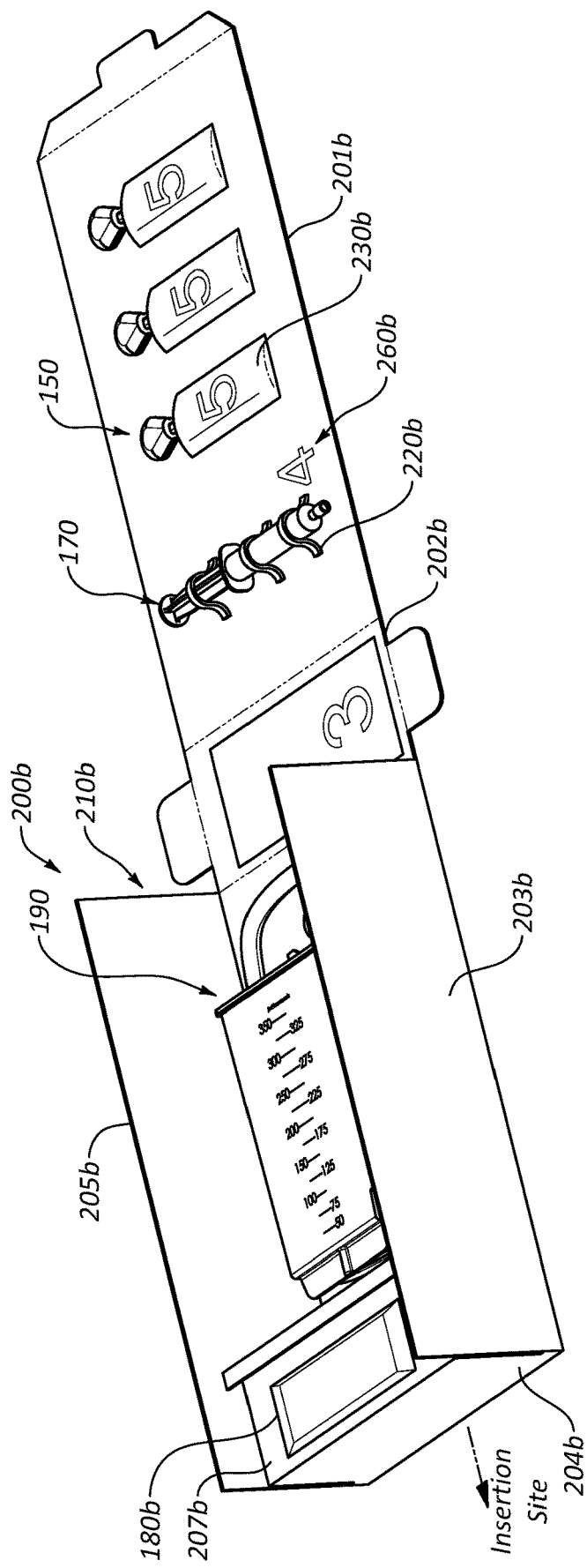
Figure 37C:
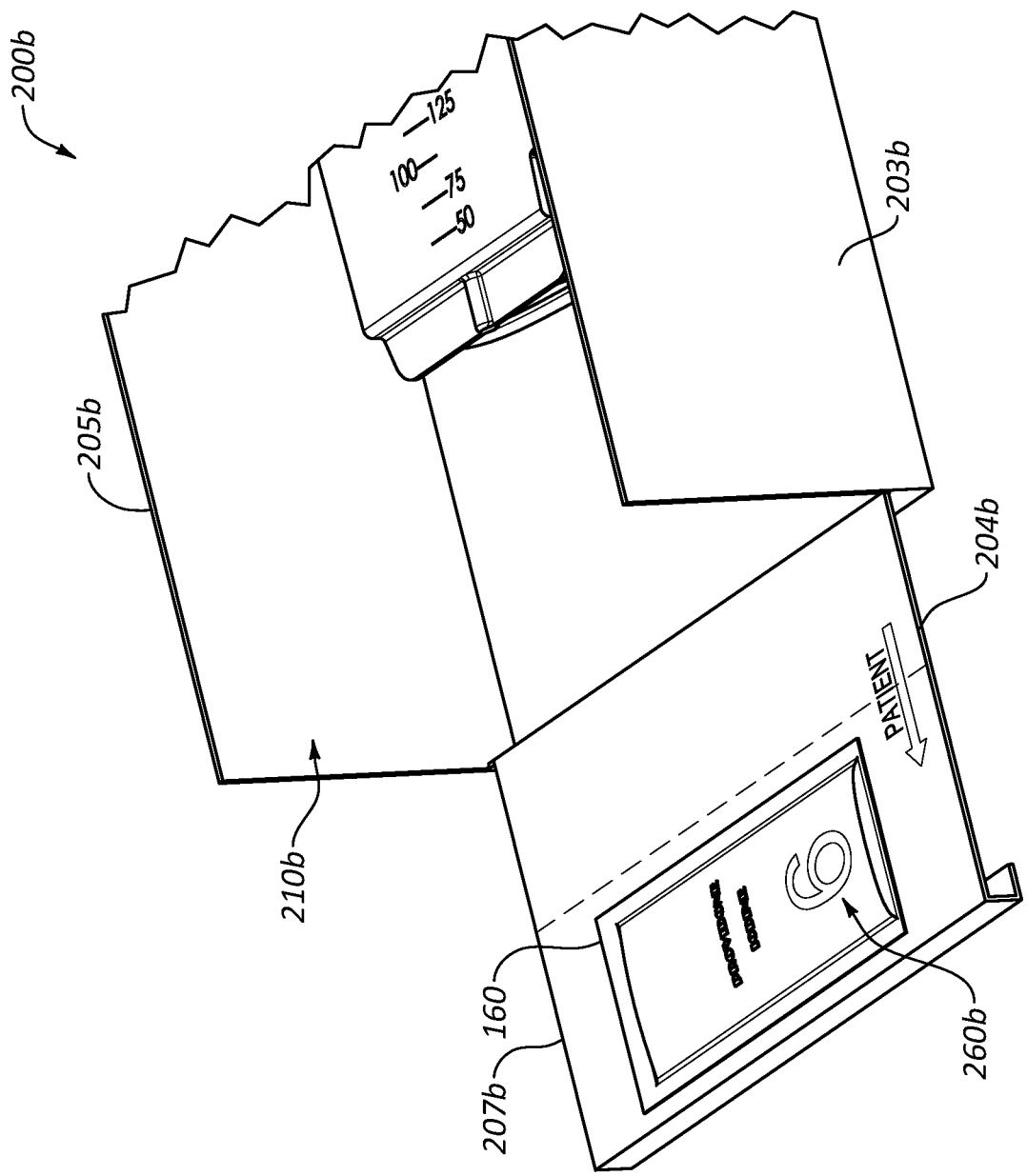

FIB. 31C is a back isometric view of the exemplary catheterization tray of FIG. 31A;

FIG. 32 is a top view of the exemplary catheterization tray of FIG. 31A with all of the contents thereof removed therefrom;

FIG. 33 is a top view of an exemplary catheterization system;

FIG. 34 is a top view of an exemplary fenestrated drape;

FIG. 35 is an isometric view of an exemplary swab;

FIG. 36A is an isometric view of an exemplary catheterization system;

FIG. 36B is an isometric view of an exemplary catheterization tray of the exemplary catheterization system of FIG. 36A;

FIG. 37A is an isometric view of an exemplary catheterization system;

FIG. 37B is an isometric view of a partially unfolded catheterization tray of the exemplary catheterization system of FIG. 37A; and FIG. 37C is a partial isometric view of the unfolded catheterization tray of the exemplary catheterization system of FIG. 37A.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but rather the intention is to cover all modifications, equivalents, and alternatives falling within the spirit and scope of the invention as defined by the appended claims.

DETAILED DESCRIPTION

The following description and accompanying figures, which describe and show certain embodiments, are made to demonstrate, in a non-limiting manner, several possible configurations of medical procedure packages, medical procedure trays, catheterization packages, catheterization trays, and associated components, assemblies, and systems, etc. and various methods of manufacturing and methods of using these according to various aspects and features of the present disclosure.

Various packages, trays, systems, assemblies, devices, and methods are described herein, including those used in various medical procedures (including, for example, catheterization procedures). While specific embodiments are discussed below by way of example, the embodiments and examples described are not intended to be limiting. Accordingly, while aspects of the invention may be described, for example, in terms of catheterization packages, catheterization trays, catheterization procedures, etc. disclosure is not limited to catheterization-related packages, trays, systems/assemblies, procedures, etc. Rather, the inventive principles associated with the embodiments described herein, may be applied to other embodiments and other types of packages, trays, systems/assemblies, devices, methods, etc.

According to various embodiments, the objectives described above and elsewhere herein may be accomplished by providing an improved medical procedure package and/or an improved medical procedure tray, e.g., with a more intuitive or better organized layout and/or instructions/procedural indicators included on the tray. For example, an improved catheterization package and/or an improved catheterization tray may be provided to improve ease of use, improve adherence to proper techniques, reduce the likelihood of infection, etc.

In accordance with various embodiments, the medical procedure package may include a medical procedure tray therein. The medical procedure package may also include any other components necessary or helpful to the medical procedure. The medical procedure tray(s) contemplated herein may be a single level tray or have multiple levels. The medical procedure tray(s) may have a variety of shapes and sizes. For example, a medical procedure tray may have a generally or approximately rectangular, square, circular, oval, triangle, hexagonal, polygon, or other shape. The medical procedure tray(s) may also include multiple compartments of varying shapes and sizes (e.g., the compartments may be of any of the shapes described above or of other shapes). Additionally, the medical procedure tray(s) and compartment dimensions may vary. As a non-limiting example, a generally rectangular medical procedure tray may have a length in the range from 7 inches to 20 inches, a width in the range from 4 inches to 12 inches, and a height in the range from 1 inch to 4 inches. In one embodiment, a generally rectangular medical procedure tray (e.g., a catheterization tray similar to that shown in FIGS. 1-4) may have a length of approximately 11 inches, a width of approximately 8.5 inches, and a height of approximately 2 inches. In one embodiment, a generally rectangular medical procedure tray (e.g., similar to the tray shown in FIGS. 5, 31A-31C, & 32) may have a length of approximately 14 inches, a width of approximately 8.5 inches, and a height of approximately 2.5 inches.

In accordance with various embodiments, the medical procedure package may be a catheterization package that includes one or more catheterization trays therein. For example, a catheterization package may include an improved catheterization tray with a more intuitive or better organized layout and/or instructions/procedural indicators included on the tray. While various features are described below in terms of a catheterization package and/or catheterization tray, the features described may also be included in or applied to medical procedure packages and/or trays used for procedures other than catheterization.

The catheterization package may include any components necessary or helpful to catheterization. Some components helpful to catheterization that may be included in the catheterization package include a drainage system, a drainage/collection bag, drainage tubing, a catheter (e.g., a Foley catheter), a drainage outlet, a stabilization device (e.g., C.R. Bard, Inc.'s StatLock® Foley stabilization device), a urine meter, swabs or swabsticks, prepping balls (e.g., absorbent cotton balls), forceps, a specimen or sample container, a label that can be filled out with details regarding the sample and adhered to the specimen or sample container, a packet or container of a sterilizing skin cleanser (e.g., a packet or container of povidone-iodine solution), a packet or container of lubricant (e.g., a syringe of lubricating jelly), a syringe of sterile liquid (e.g., a 10 cc syringe of sterile water for inflating the retention balloon of the Foley catheter), a fenestrated drape to place on patient, an underpad to place under the buttocks of a patient (e.g., a waterproof absorbent underpad), gloves (e.g., a package of rubber gloves, latex gloves, latex-free gloves), a sterile wrap (e.g., a CSR wrap), a belly band (e.g., to hold the sterile wrap in a folded configuration), a perineal care packet, hand sanitizer (e.g., antiseptic gel hand rinse), moist towelettes (e.g., a package of castile soap towelettes), instructions/procedural indicators (e.g., instruction sheet for health care provider and/or instruction pamphlet for patient), a checklist of safety considerations/steps, a patient information chart, an insert sheet, a packaging label, an outer container (e.g., a sealed bag), and/or other components. The components included in the catheterization package may be included in one or more compartment of the catheterization tray, in a separate package or bag (e.g., a package outside the tray), or in a second catheterization tray.

The catheterization tray(s) may be labeled with step-wise instructions/procedural indicators arranged in logical locations on the tray(s). The catheterization tray(s) may have a layout and design that makes the catheterization procedure more intuitive. A single-level catheterization tray having a generally rectangular shape, including multiple compartments of varying shapes, including step-wise instructions/procedural indicators, and having an improved layout is shown, for example, in FIGS. 1-4 and described below. Other similar single-level catheterization trays are shown in FIGS. 5, 31A-31C, & 32 as well.

According to various embodiments and as shown, for example, in FIGS. 1-5, the catheterization tray may include: a main compartment 1; a syringe or catheter compartment 2; a swab compartment 3; a small storage or overflow compartment 4; and a corner storage compartment 5. The tray also includes stiffening ribs (e.g., stiffening ribs 20 shown in FIG. 2; see also stiffening ribs 205 in FIGS. 31A-31C), which help to strengthen the tray and keep the tray from bending when held, e.g., when held by one hand.

Figure 1:
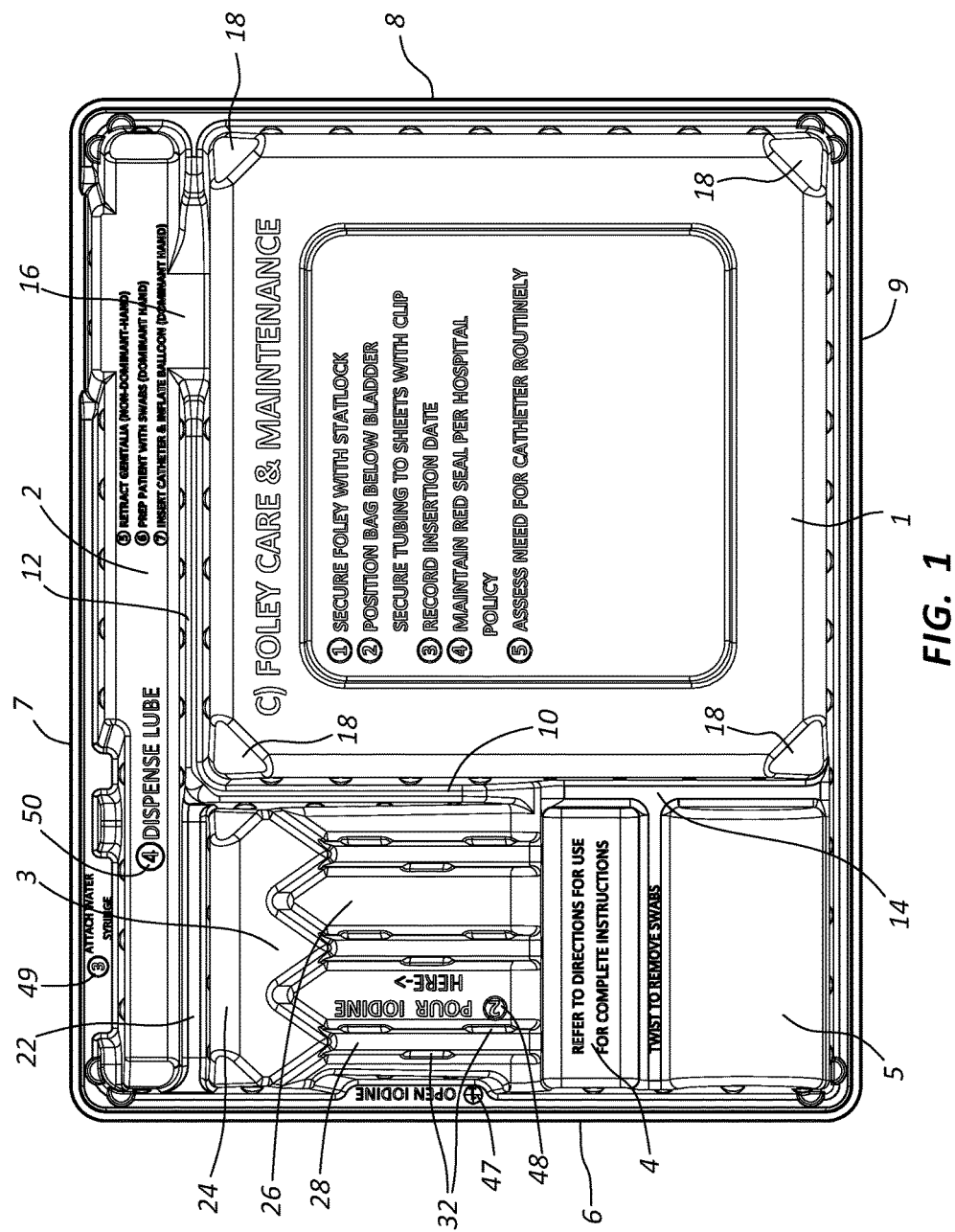
FIG. 1 shows a top view of an exemplary medical procedure tray including integrated instructions/procedural indicators in the form of a catheterization tray.
Figure 2:
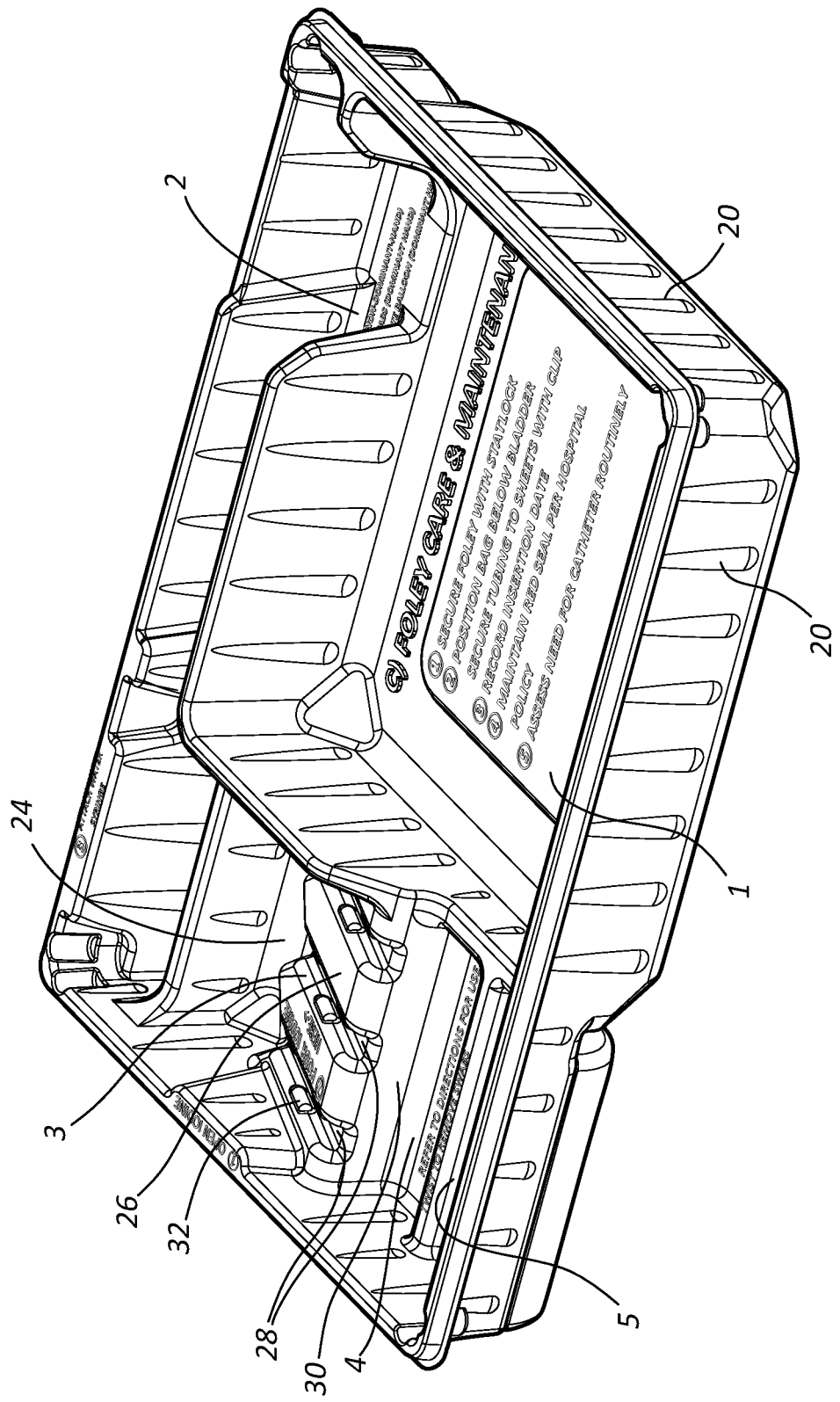
FIG. 2 shows a top, front (or proximal), right perspective view of the exemplary medical procedure tray of FIG. 1.
Figure 5:
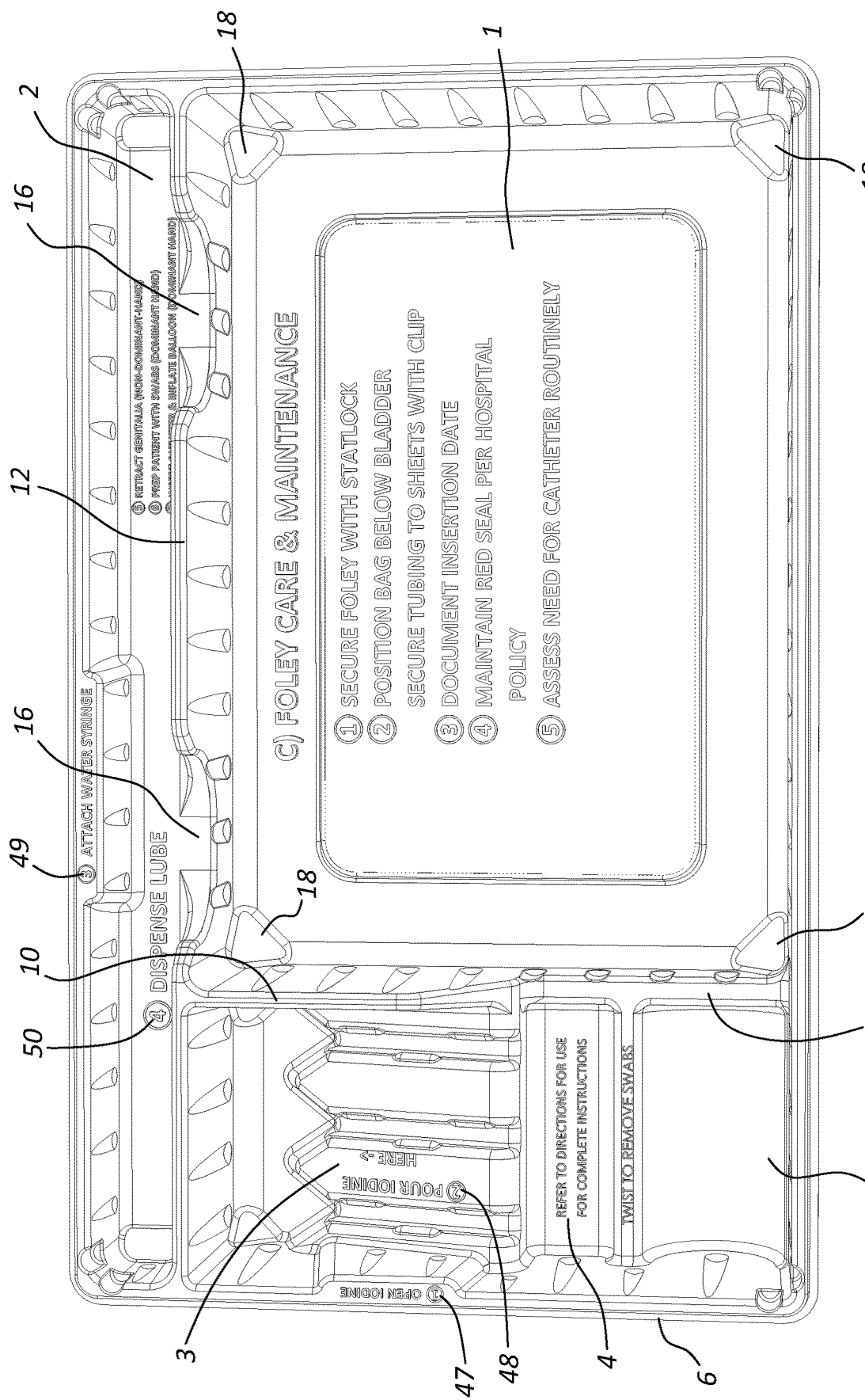
FIG. 5 shows a top view of another exemplary medical procedure tray including integrated instructions/procedural indicators in the form of a catheterization tray that is larger than the tray in FIG. 1.

With reference to FIGS. 1, 2, and 5, the main compartment 1 is the largest compartment in the tray and may contain any number of items for the catheterization procedure, for example, a drainage system, a collection bag, a drape, an underpad, an inflation syringe, and/or gloves. A drainage system that may be included in the catheterization package and/or in the main compartment 1 may include, for example, a drainage/collection bag, drainage tubing, a catheter (e.g., a Foley catheter), a drainage outlet, a urine meter, and/or other drainage system components. The drainage system components may be pre-connected and stored in the catheterization package in a pre-connected state, or the drainage system components may be stored as separate components to be assembled/connected later.

The drainage system and tubing included in the catheterization package may be configured and arranged in a way that helps improve drainage of urine through the system and tubing. For example, the tubing or other components of the drainage system may be designed to break up the surface tension of the fluid in order to improve drainage. The drainage tubing may be short to accommodate lower bed profiles or may have an adjustable length for various size beds. The tubing or other drainage system components may have a coating (e.g., a lubricious coating) thereon to facilitate drainage therethrough. Optionally, the tubing or other drainage system components may include a superhydrophobic pattern thereon to facilitate drainage.

Additionally, there are a range of suitable durometers of the tubing or other drainage system components. However, for components that may be coiled in the tray (e.g., drainage tubing and/or the catheter), it is desirable to have a tubing durometer that does not tend to hold a set shape at room temperature. For example, one can experiment with different durometers to ensure that the durometer ultimately used for coiled components does not tend to leave the component in a coiled shape when removed from the tray and put to use. It is desirable, for example, to give the drainage tubing a durometer such that, despite being packaged in the main compartment in a coiled state, when connected to a patient, the drainage tubing does not remain coiled, but tends to straighten out to facilitate drainage. The drainage tubing can be made of polyvinyl chloride (PVC), silicone, latex, Teflon, or another polymer material.

As shown in FIG. 1, outer or peripheral walls on sides 8 and 9 of the tray form two orthogonal walls of the main compartment 1 and form a corner of the main compartment 1 where the outer or peripheral walls on sides 8 and 9 intersect each other. Two additional, interior walls 10 and 12 separate the main compartment 1 from other compartments. The two interior walls 10 and 12 include reduced height portions 14 and 16 (with reduced heights compared with the tray's full-height interior or outer walls).

Also, the main compartment 1 includes interior fillets 18 at the corners formed between the floor of the main compartment 1 and its walls. Such fillets 18 may reinforce the corners of the main compartment 1.

As shown, for example, in FIGS. 1, 2, and 5, the main compartment of the tray may include instructions/procedural indicators and/or other information integrated thereon. For example, the main compartment may include a logo or trademark name written thereon, e.g., "SureStep™ Foley Tray System" and "BARD." The main compartment may also, or alternatively, include instructions/procedural indicators related to the catheterization printed or otherwise included thereon. For example, the main compartment may include instructions/procedural indicators for how to catheterize a patient or instructions/procedural indicators for steps to take after catheterization. Optionally, the main compartment may include instructions/procedural indicators for proper Foley care and maintenance. As shown, for example, in FIGS. 1 and 5, the instructions/procedural indicators integrated on the main compartment may include instructions/procedural indicators stating, "(1) Secure Foley with StatLock®", "(2) position bag below bladder", "secure tubing to sheets with clip", "(3) document insertion date", "(4) maintain red seal per hospital policy", "(5) assess need for catheter routinely." The instructions/procedural indicators or other information may be in upper case letters, in bold, or otherwise called out for greater visibility to ensure the clinician reads the instructions/procedural indicators or other information. Optionally, instructions/procedural indicators may be printed or otherwise included on the main compartment to remind the health care provider/clinician to instruct the patient regarding how to properly care for and maintain the catheter after catheterization. The instructions/procedural indicators may be written to help the health care provider/clinician remember to cover important instructions that should be given to the patient.

The syringe or catheter compartment 2 has an elongated shape and spans approximately an entire length of the tray. Outer or peripheral walls of the tray contribute to form three walls of the syringe or catheter compartment 2. Interior wall 12 spans between opposing outer or peripheral walls of the tray and separates the syringe or catheter compartment 2 from other compartments—namely, from the main compartment 1 and from the swab compartment 3. The syringe or catheter compartment 2 is sized and shaped to contain one or more syringes (e.g., a syringe of lubricating jelly and a syringe of sterile liquid to inflate the retention balloon) and/or a catheter, such as a Foley catheter. For example, a syringe of lubricating jelly and a syringe of 10 cc sterile water may be packaged in the syringe or catheter compartment 2, but the end user (e.g., a clinician) may remove the syringes at the time of catheterization and place the catheter in the syringe or catheter compartment 2 prior to insertion into a patient (e.g., to facilitate lubrication of the catheter).

A portion of the interior wall 12 separates the catheter compartment 2 from the main compartment 1. Some of interior wall 12 has a full height (e.g., extends as high as the outer walls of the tray), but interior wall 12 also includes reduced height portions 16 and 22 (which have a reduced height relative to the full height of the interior wall 12, tray, or the outer walls). Reduced height portion 16 of interior wall 12 may act as a break or opening in the wall, which may place the syringe or catheter compartment 2 in fluid communication with the main compartment 1 and vice versa. Along reduced height portion 16, the interior wall 12 may form a small step between the syringe or catheter compartment 2 and the main compartment 1, e.g., as shown in FIGS. 2 and 6 (see also FIGS. 31A-31C). The step may also be formed by the main compartment 1 having a lower/deeper floor than the floor of the syringe or catheter compartment 2, e.g., as shown in FIGS. 2 and 6 (see also FIGS. 31A-31C).

In FIGS. 1 and 2, another reduced height portion of the interior wall, i.e., reduced height portion 22, separates the syringe or catheter compartment 2 from the swab compartment 3. Reduced height portion 22 of the interior wall 12 has a partial or reduced height relative to the full height of the tray or the outer walls. FIG. 5 shows an alternate arrangement of reduced height portions 16, wherein both reduced height portions 16 are located along the interior wall between the syringe or catheter compartment and the main compartment (i.e., there is no reduced height portion 22 between the syringe or catheter compartment and the swab compartment). Other arrangements and configurations are also possible. If syringes are packaged or included in syringe or catheter compartment 2, the reduced height portions (e.g., reduced height portions 16 and 22) help facilitate easy removal of the syringes from the syringe or catheter compartment 2 by providing more open space for the end user to reach into the tray and grasp onto the syringes. This makes removal of the syringes easier than if the interior wall 12 did not have any reduced height portions and the clinician had to try to grasp the syringes within a narrower region.

As shown, for example, in FIGS. 1 and 5, the syringe or catheter compartment of the tray may also include instructions/procedural indicators and/or other information integrated thereon. For example, the syringe or catheter compartment may optionally include instructions/procedural indicators related to the catheterization written thereon. As shown in FIGS. 1 and 5, the instructions/procedural indicators integrated on the syringe or catheter compartment may include instructions/procedural indicators stating "Dispense & Lube Foley here" (alternatively, this instruction may simply say "Lube Foley"), "retract genitalia (non-dominant hand)", "prep patient with swabs (dominant hand)", "insert catheter & inflate balloon (dominant hand)." As shown in FIGS. 1 and 5 and as stated above, the instructions/procedural indicators may inform the health care provider which hand to use for a given step, e.g., dominant or non-dominant hand. The instructions/procedural indicators or other information may be in upper case letters, in bold, or otherwise called out for greater visibility to ensure the clinician reads the instructions/procedural indicators or other information.

Note that the outer or peripheral walls of the catheterization tray may also include instructions/procedural indicators or other information thereon. For example, as shown in FIGS. 1, 2, and 5, the outer or peripheral wall 6 may include a reduced height portion with an instruction/procedural indicator 47 to "open iodine," while outer or peripheral wall 7 may include a reduced height portion with an instruction/procedural indicator 49 to "attach water syringe." The instructions/procedural indicators or other information may be in upper case letters, in bold, or otherwise called out for greater visibility to ensure the clinician reads the instructions/procedural indicators or other information.

As shown in FIGS. 3 and 4, the base 55 of the syringe or catheter compartment 2 may be offset from the bases of all other compartments. In other words, the base 55 of the syringe or catheter compartment 2 may be not as deep or separated from the top of the tray as, for example, the base 57 of the main compartment 1. As the base 55 is offset from the bases of the other compartments, the bottom/floor of the syringe or catheter compartment is offset from bottoms/floors of the other compartments, including being offset from the bottom/floor of the main compartment 1.

The swab compartment 3 spans along a portion of the tray's outer or peripheral wall along side 6 of the tray; that portion of the outer wall forms a wall of the swab compartment 3. The swab compartment 3 may contain various items, for example, swabs or swabsticks and iodine. Portions of interior wall 10 and interior wall 12 extend along two sides of the swab compartment 3 forming walls of the swab compartment 3, and separate the swab compartment 3 from the main compartment 1 and the syringe or catheter compartment 2, respectively. Also, the small storage or overflow compartment 4 extends along a fourth side of the swab compartment 3. In one embodiment as shown, for example, in FIGS. 1 and 2, interior wall 10 has a full height where it separates the swab compartment 3 from the main compartment 1, while interior wall 12 has a reduced height (i.e., at reduced height portion 22) that separates the swab compartment 3 from the syringe or catheter compartment 2. In one embodiment as shown, for example, in FIG. 5, interior wall 10 and interior wall 12 both have a full height whether they separate the swab compartment 3 from the main compartment 1 and the syringe or catheter compartment 2.

The swab compartment 3 has an angled bottom/floor that spans between the small storage or overflow compartment 4 and the syringe or catheter compartment 2 and has a downward slope therebetween (i.e., the bottom/floor of the swab compartment 3 near the catheter compartment 2 is lower than near the storage compartment 4). As such, fluid poured into the swab compartment may flow in a direction toward the catheter compartment 2 and pool in the lowest/deepest portion or well 24 of the swab compartment near interior wall 12 (e.g., adjacent reduced height portion 22 in FIGS. 1 and 2) where it separates the swab compartment 3 from the catheter compartment 2. Fillets may be included in the corners of the swab compartment 3 similar to fillets 18 in the main compartment 1, e.g., as shown in FIGS. 1 and 2.

Figure 8:
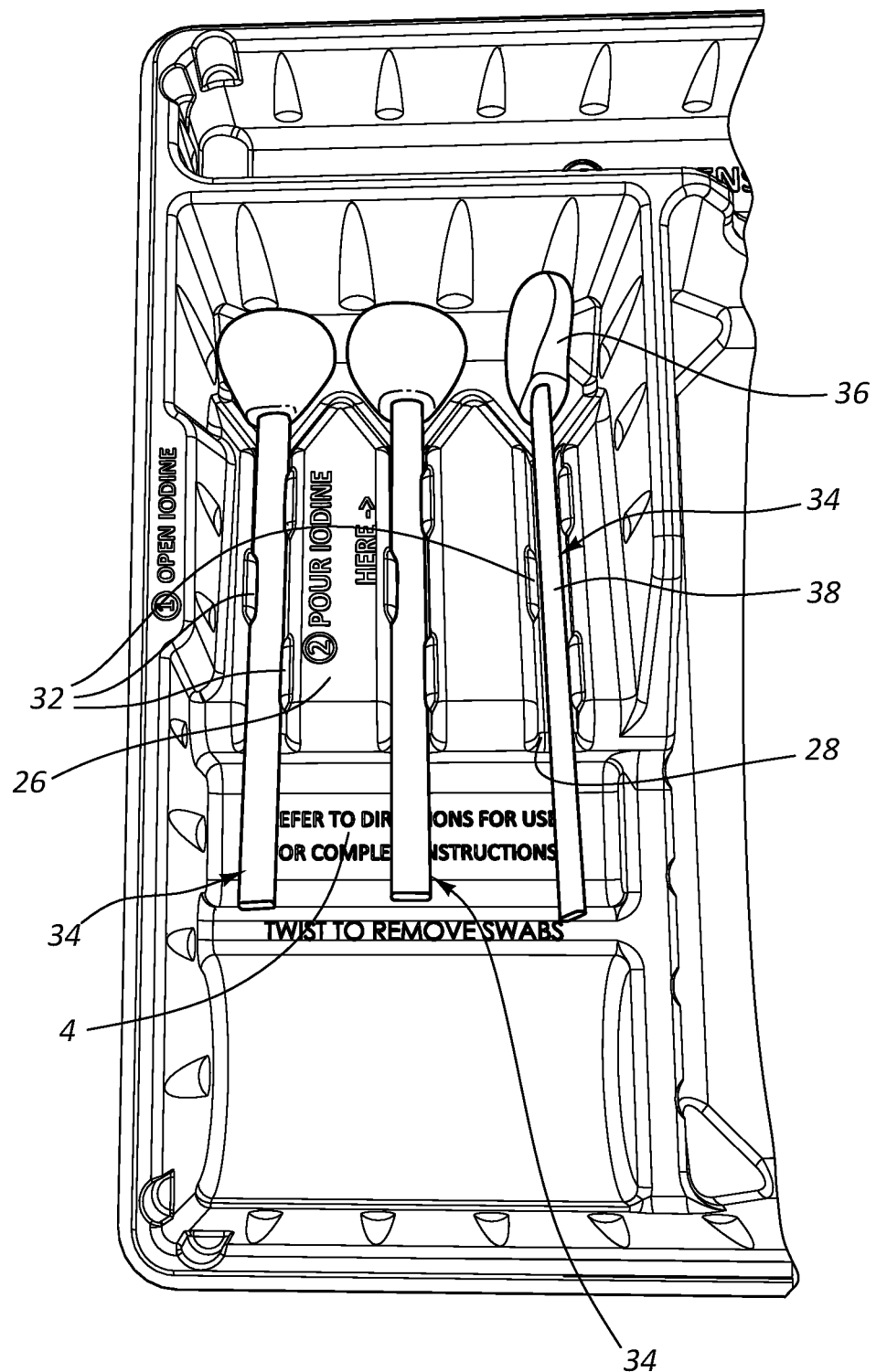
FIG. 8 shows a top view of an exemplary swab compartment and small storage or overflow compartment of a catheterization tray including exemplary swabs or swabsticks similar to the swab or swabstick shown in FIGS. 7A-7C, wherein one swab or swabstick is rotated approximately 90° to release it from the securement features of the swab compartment.

FIG. 8 shows a larger view of the swab compartment 3 and the adjacent small storage or overflow compartment 4 with swabs or swabsticks contained in the swab compartment 3. Near the small storage or overflow compartment 4, the bottom/floor of the swab compartment 3 may be supported by another interior wall 30 (shown on FIG. 2) that separates the small storage or overflow compartment 4 from the swab compartment 3. Also, this interior wall 30 may extend upward (from the bottom/floor of the small storage or overflow compartment 4) only to the bottom/floor of the swab compartment 3, leaving the bottom/floor of the swab compartment 3 unobstructed near the small storage or overflow compartment 4 (as such, swabs or swabsticks with a longer stick/stem may extend over a portion of the small storage or overflow compartment 4 from the bottom/floor of swab compartment 3 as shown, for example, in FIG. 8). This design or arrangement also allows small storage or overflow compartment 4 to act as an overflow well in case too much fluid/iodine is poured into swab compartment 3.

The bottom/floor of the swab compartment 3 includes one or more channels 28 extending at least partially along the region between the small storage or overflow compartment 4 and the catheter compartment 2. Near the catheter compartment 2, the channels 28 extend to and are in fluid communication with the lowest/deepest portion or well 24 of the bottom/floor of the swab compartment 3 adjacent interior wall 12, such that liquid poured into the channel(s) 28 can flow downward through the channel(s) 28 along the downward slope and pool in the lowest/deepest portion or well 24 of the bottom/floor of the swab compartment 3, near the catheter compartment 2. The channel(s) 28 may be designed to hold an elongated device (e.g., swabs or swabsticks) and each channel 28 may be separated by one or more barriers 26 to help space the elongate devices (e.g., swabs or swabsticks) apart. Channel(s) 28 may also include undercutting or snap-in features (e.g., features 32) that may help secure elongated devices, such as swabs, swabbing sticks, or swabsticks in the channel(s) 28.

As shown, for example, in FIGS. 1, 5, and 8, the swab compartment of the tray may also include instructions/procedural indicators and/or other information integrated thereon. For example, the swab compartment (e.g., on one of barriers 26) may optionally include instructions/procedural indicators related to the catheterization printed or otherwise included thereon. As shown in FIGS. 1, 5, and 8, the instructions/procedural indicators integrated on the swab compartment may include an instruction/procedural indicator stating "pour iodine here." The instructions/procedural indicators or other information may be in upper case letters, in bold, or otherwise called out for greater visibility to ensure the clinician reads the instructions/procedural indicators or other information.

One or more swabs or swabsticks (e.g., swab or swabstick 34 shown in FIGS. 6A-8) may be packaged in the swab compartment 3 and held in channels 28 (e.g., as shown in FIG. 8). The swabs or swabsticks may be specially designed to fit in swab compartment 3 and to be held in channels 28. Swab compartment 3 may also include iodine or povidone-iodine solution. The iodine or povidone-iodine solution may be packaged in its own container, packet, or syringe in the swab compartment 3, e.g., povidone-iodine packet 52 shown in FIG. 26. Alternatively, the iodine or povidone-iodine solution may be stored and/or sealed in swab compartment 3 in direct contact with the swab(s) or swabstick(s) 34 (e.g., packaged/sealed such that it is in contact with a portion of the bottom/floor of swab compartment 3).

Figure 6A:
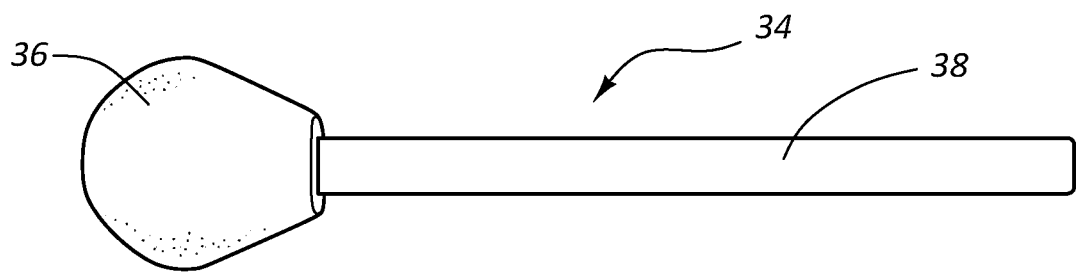
FIG. 6A shows a top view of an exemplary swab or swabstick that may be included in a catheterization package and/or tray.
Figure 6B:
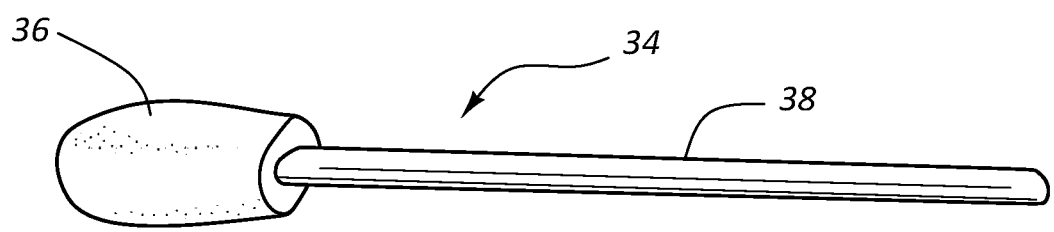
FIG. 6B shows a side perspective view of the exemplary swab or swabstick in FIG. 6A.
Figure 6C:
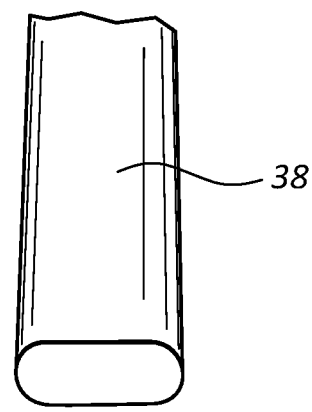
FIG. 6C shows an end view of the exemplary swab or swabstick in FIG. 6A to show the cross-sectional shape of the elongate member or stick.
Figure 7A:
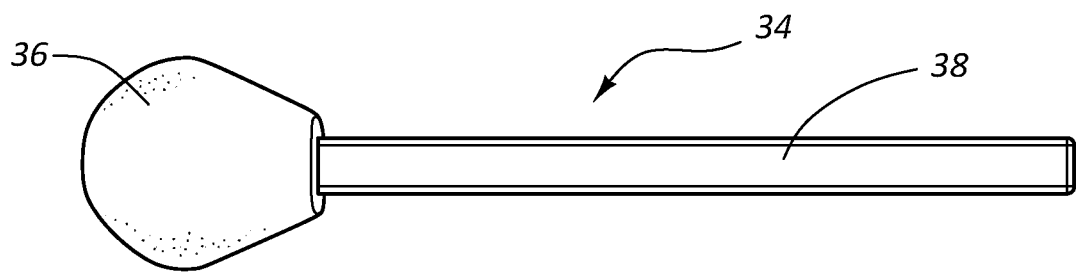
FIG. 7A shows a top view of an exemplary swab or swabstick that may be included in a catheterization package and/or tray.
Figure 7B:
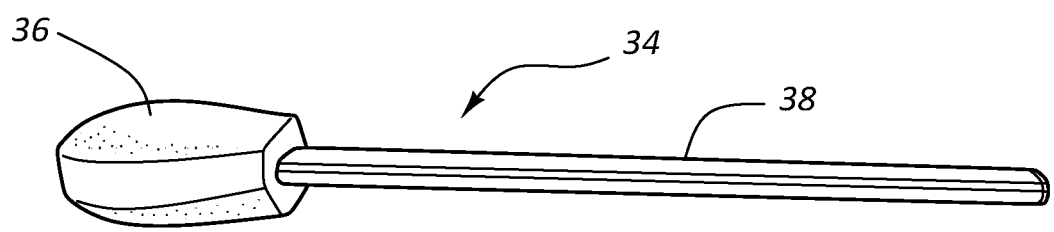
FIG. 7B shows a side perspective view of the exemplary swab or swabstick in FIG. 7A.
Figure 7C:
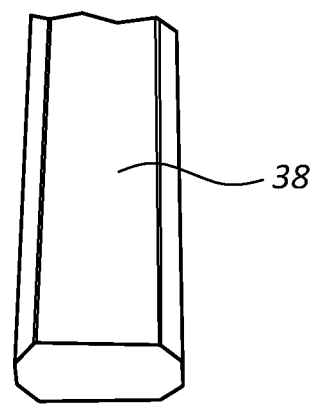
FIG. 7C shows an end view of the exemplary swab or swabstick in FIG. 7A to show the cross-sectional shape of the elongate member or stick, the cross-sectional shape being different from that shown in FIG. 6C.

FIGS. 6A-6C show one embodiment of swab or swabstick 34 with an elongate member or stick/stem 38 having more rounded sides (e.g., in cross-section) than the swab or swabstick 34 shown in FIGS. 7A-7C. FIGS. 7A-7C show one embodiment of swab or swabstick 34 with an elongate member or stick/stem 38 having less rounded or more angular sides than the swab or swabstick 34 shown in FIGS. 6A-6C. Swab or swabstick 34, as shown in FIGS. 6A-7C, is representative of other possible swabs or swabsticks that may be included. Swab or swabstick 34 includes an absorbent head 36 and an elongate member or stick/stem 38. Absorbent head 36 is designed to allow for greater saturation in cleansing solution (e.g., in iodine or povidone-iodine solution) and for greater contact with the surface area of the region to be cleansed. Absorbent head 36 may be formed from various materials, including foam, rayon (e.g., puffs of rayon or a spiral of rayon), cotton, other materials, and/or a combination of one or more of these materials. To improve saturation of the absorbent head, the absorbent head 36 is desirably made of a material that readily absorbs and distributes the cleansing solution. Any material that absorbs a significant percentage of its weight in cleansing solution is desirable for use in the absorbent head, especially if it also releases a large percentage of absorbed cleansing solution, i.e., it is desirable to use a material that absorbs a large amount of cleaning solution and also releases a large amount of cleaning solution when used on the patient for cleaning. It has been found that forming the absorbent head 36 of foam (as opposed to rayon or other materials) provides the absorbent head 36 with improved absorption of and saturation with cleansing solution. Further, a foam absorbent head readily releases a large amount of the cleansing solution when put in contact with the region of the patient to be cleansed and when compressed slightly against the region being cleansed. This ready release of cleansing solution makes cleansing the region of the patient easier and allows the end user to be more gentle when cleansing the patient. If absorbent head 36 is made entirely or partially of foam, the foam may be open-cell foam, closed-cell foam, polyurethane foam, high density foam, latex foam, honey gold foam, or other types of foam. The absorbent head may be heated such that it bonds to the elongate member or stick (e.g., the foam may be heated to bond to the stick), or other means of attachment may be used, e.g., using an adhesive.

Preferably the foam or other material(s) selected for the absorbent head do not degrade or at least resist degrading when in contact with the cleansing solution. In one embodiment, the swabs or swabsticks may be stored in contact with iodine or a povidone-iodine solution, so they are already saturated when they are first accessed in the catheterization package. For example, a seal may be placed in or over swab compartment 3 that holds a cleansing solution in contact with the absorbent head(s) of the swab(s) or swabstick(s) while preventing leaks until the seal is removed. When packaged and stored in contact with the cleansing solution, it is vital that the absorbent head not degrade over time. Honey gold foam, for example, is sufficiently resistant to degradation when in contact with an iodine or povidone-iodine solution.

Absorbent head 36 may be of a variety of sizes and shapes. Preferably, the foam is shaped in such a way as to provide for greater contact with the surface area of the region to be cleansed. For example, the absorbent head 36 may be shaped such that the distal end or distal region (e.g., regions that come into contact with the patient), are substantially larger than regions that are less likely to come into contact with the patient (e.g., the proximal end or where the absorbent head 36 attaches to the elongate member or stick 38). This provides more surface area in the patient-contacting end of the absorbent head and makes cleansing the patient quicker and easier. Further, with the distal region of the absorbent head being larger, the majority of the iodine is absorbed into the area that contacts the patient (in contrast, when the largest region of the absorbent head is not at or near the distal end, much of the iodine is wastefully absorbed into a location that does not contact or cleanse the patient). The absorbent head 36 may be shaped as shown in FIGS. 6A-7B and may be wider than it is thick. The absorbent head 36 could also be shaped to be generally or approximately circular, rectangular, or trapezoidal. Optionally, the shape of absorbent head 36 may be generally or approximately conical, pyramidal, tear drop, ovoid, or triangular in shape (with the larger base end positioned at the distal tip of the swab or swabstick), or may be another shape. If generally pyramidal in shape, the base of the pyramidal shape may be generally triangular, square, pentagonal, hexagonal, etc. Even if otherwise generally conical, pyramidal, or another shape, the edges of the absorbent head at the distal end may be curved or tapered (e.g., as the distal edges are curved in FIGS. 6A-7B). Further, the distal end of the elongate member or stick 38 may also be curved (e.g., the distal end may be semi-circular rather than flat across the top or distal-most edge), as curves are less likely to harm patient when cleansing with a swab or swabstick.

In one embodiment, the length of the absorbent head may be between 0.5 and 2 inches (in one embodiment, the length may be approximately 1 inch), the width of the absorbent head at its widest may be between 0.5 and 2 inches (in one embodiment, the width at its widest may be approximately 1 inch) and the width of the absorbent head at its narrowest may be between 0.1 and 1 inches (in one embodiment, the width at its narrowest may be approximately ½ of an inch). Further, if the absorbent head is not generally conical or pyramidal in shape (i.e., such that its width and thickness are the same all around), it may have a thickness less than its width, e.g., a thickness between 0.1 and 1 inches (in one embodiment, the thickness may be approximately ⅜ of an inch).

In one embodiment, the elongate member or stick 38 may have a length between 2 and 7 inches (e.g., the elongate member or stick 38 may have a length between 3.5 and 4.5 inches, or a length of approximately 4.25 inches). The length of penetration of the stick 38 into the absorbent head 36 (i.e., the length the stick 38 that extends distally beyond the proximal end of the absorbent head) may be between 0.25 inches and 1 inch (e.g., the length of penetration may be approximately 0.5 inches). It is preferable to ensure that the length of penetration is within a good range relative to the overall length of the absorbent head. If the stick 38 extends too far into the absorbent head 36, the patient's skin may be too easily damaged by the stick 38 (e.g., it may be more likely to scrape against the patient during cleansing, and may not be padded by enough foam). Whereas, if the stick 38 does not extend far enough into the absorbent head 36, the absorbent head 36 will lack structure and flop around (especially if saturated with liquid), which makes it harder for the end user to guide the absorbent head of the swab or swabstick and effectively cleanse the patient. Ideally, the length of penetration of the stick 38 will extend between 35 and 70% of the length of the absorbent head 36 (e.g., the length of penetration may be about 50% of the length of the absorbent head). The elongate member or stick 38 may be formed from various materials, including a plastic or polymer material.

The elongate member or stick 38 may have a variety of different cross-sectional sizes and shapes. For example, the swab or swabstick may be biased to be relatively flat or have a generally rectangular cross-section (or a rectangular-like cross-section but with rounded edges as shown, for example in FIG. 6C, or with cut off edges as shown, for example, in FIG. 7C), so it is easier to hold. The elongate member or stick 38 shown in FIGS. 6A-6C has rounded edges, but has a roughly rectangular shape otherwise. This is a shape that is easier to hold and manipulate while cleaning a patient than a stick with a circular cross-section. Further, this and similar cross-sectional shapes for the elongate member or stick 38 make it possible for the swabs or swabsticks to snap into the tray or be held under features 32 to prevent movement of the swabs or swabsticks during shipping or before use. To remove a swab or swabstick of this cross-section, one can simply twist the elongate member or stick 38 in a clockwise or counter clockwise direction and the features 32 easily release the swab or swabstick for use. For example, FIG. 8 shows two swabs or swabsticks that are snapped or held in place under the features 32, and also shows one swab or swabstick that has been twisted such that the features 32 no longer hold the swabstick or prevent its removal. This makes the swabs or swabsticks very secure in the swab compartment 3 during shipping and before use, but also makes removal of the swabs or swabsticks at the time of catheterization very simple and easy.

In one embodiment, if the elongate member or stick is of a generally flattened (e.g., generally rectangular) shape, the width or diameter of the elongate member or stick 38 may be between approximately ⅛ of an inch and ¾ of an inch (e.g., the width may be about ¼ of an inch), whereas the thickness may be between ¹⁄₁₆ of an inch and ½ of an inch (e.g., the thickness may be approximately ⅛ of an inch). If the elongate member or stick is of a generally circular cross-section or is generally cylindrical in shape, the diameter of the elongate member or stick 38 may be between ⅛ of an inch and ½ of an inch (e.g., the diameter may be about ¼ of an inch).

The swabs or swabsticks are loaded into the tray and held in such a way that the absorbent head 36 is in the lowest/deepest portion or well 24 of the bottom of the swab compartment 3 such that they are exposed to the iodine that pools in the lowest/deepest portion or well 24 of the bottom of the swab compartment 3 and easily saturate with the iodine or povidone-iodine solution. However, the elongate member or stick 38 may be loaded into the tray and held in such a way that the elongate member or stick 38 is not itself exposed to the iodine or povidone-iodine solution.

The small storage or overflow compartment 4 spans along a portion of the tray's outer or peripheral wall 6, which forms a wall of the small storage or overflow compartment 4. Three other walls of the small storage or overflow compartment 4 are formed by partial-height interior walls that separate the small storage or overflow compartment 4 from the main compartment 1, swab compartment 3, and corner compartment 5. These compartments may surround the small storage or overflow compartment 4 on three sides thereof. The small storage or overflow compartment 4 may act as an overflow well to collect any fluid that might overflow from the swab compartment. Optionally, the small storage or overflow compartment 4 may store or hold one or more items useful for catheterization.

As shown, for example, in FIGS. 1 and 5, the small storage or overflow compartment of the tray may also include instructions/procedural indicators and/or other information integrated thereon. For example, the small storage or overflow compartment may optionally include instructions/procedural indicators related to the catheterization printed or otherwise included thereon. As shown in FIGS. 1 and 5, the information integrated on the small storage or overflow compartment may include a reminder that the health care provider/clinician should "refer to directions for use for complete instructions." The instructions/procedural indicators or other information may be in upper case letters, in bold, or otherwise called out for greater visibility to ensure the clinician reads the instructions/procedural indicators or other information.

The corner storage compartment 5 spans along portions of the tray's outer or peripheral wall 6 and outer or peripheral wall 9, which form two walls and a corner of the corner storage compartment 5. Two other walls of the corner storage compartment 5 may be formed by partial-height interior walls that separate the corner storage compartment 5 from the main compartment 1 (e.g., reduced height portion 14) and small storage or overflow compartment 4. These compartments surround the corner storage compartment 5 on two sides thereof.

The bottom/floor of the corner storage compartment 5 may be non-planar; namely, the bottom/floor may have a non-planar, rounded, or partially cylindrical shape. This shape may be particularly useful for holding a specimen or sample container. Corner storage compartment may store or hold various implements useful for catheterization. For example, corner storage compartment may hold a label that can be filled out by a clinician on a first side and adhered to a specimen or sample container on a second side. The second side may already include an adhesive thereon; the adhesive may be covered by a removable cover sheet that may be removed at the time of adhering. The corner storage compartment may also include a specimen or sample container 54.

In one embodiment, at least some of the compartments may be sealed in a manner that prevents contamination thereof. In one embodiment, at least one of the compartments may be unsealed independently of at least one other compartment. For example, a user may first unseal the main compartment, leaving other compartments sealed. After using items contained in the main compartment, the user may unseal another compartment and use items contained in that compartment.

In one embodiment, a user may unseal the swab compartment 3 prior to unsealing the syringe or catheter compartment 2 or the main compartment 1. The user may pour iodine or other sterilizing solution into the swab compartment and may use the swab compartment for applying the sterilizing solution onto swabs, and then use the iodine soaked swabs to cleanse the patient. A user may then unseal the syringe or catheter compartment 2 and dispense lubricant therein prior to unsealing the main compartment 1. A user may then unseal the main compartment 1 to access the catheter. The shape and size of the catheter compartment facilitate lubrication of the catheter (e.g., a tip of the catheter can rotate within the elongated shape of the catheter compartment and collect lubricant on its surface during the rotation). The catheter may be lubricated in the syringe or catheter compartment 2 and then inserted into the patient's urethra.

According to various embodiments, and as shown in FIGS. 1, 2 and 5, and as discussed above, the tray may have ordered, stepwise instructions/procedural indicators thereon for a suitable or preferred catheter insertion technique.

Other aspects or features of the catheterization package(s) and catheterization tray(s) are also described below in the context of exemplary procedures or methods of using the catheterization package and catheterization tray, and in the context of methods of manufacturing or packaging a catheterization package. The aspects or features described below may be incorporated into the various embodiments already discussed above. The arrangement of components and how they are accessed is part of the overall intuitive design of the catheterization package, i.e., components and features are arranged in a logical manner that flows from step to step to make the catheterization procedure more intuitive and make completing the procedure easier and/or quicker. Step-by-step ordering of the components in the catheterization package helps a user/clinician to logically know what step comes next. For example, a first item may be revealed in the package, then once the first item is used, a second item that was underneath the first item is revealed, the second item being next logical item for use in the catheterization procedure. Once the second item is used, a third item that was underneath the second item may be revealed, the third item being the next logical item for use in the catheterization procedure, and so on.

The catheterization package(s) and catheterization tray(s) described herein may be used in many different ways. An exemplary, non-limiting, method of use is described below. However, clinicians may vary the steps or procedures described herein, may reorder the steps, may perform additional steps beyond those described, and/or may omit certain steps as circumstances and a patient's unique needs may require. Further, the description below can be considered a description of an overall procedure with many steps or can be considered a series of individual methods or procedures each including only a subset of the steps described.

Figure 9:
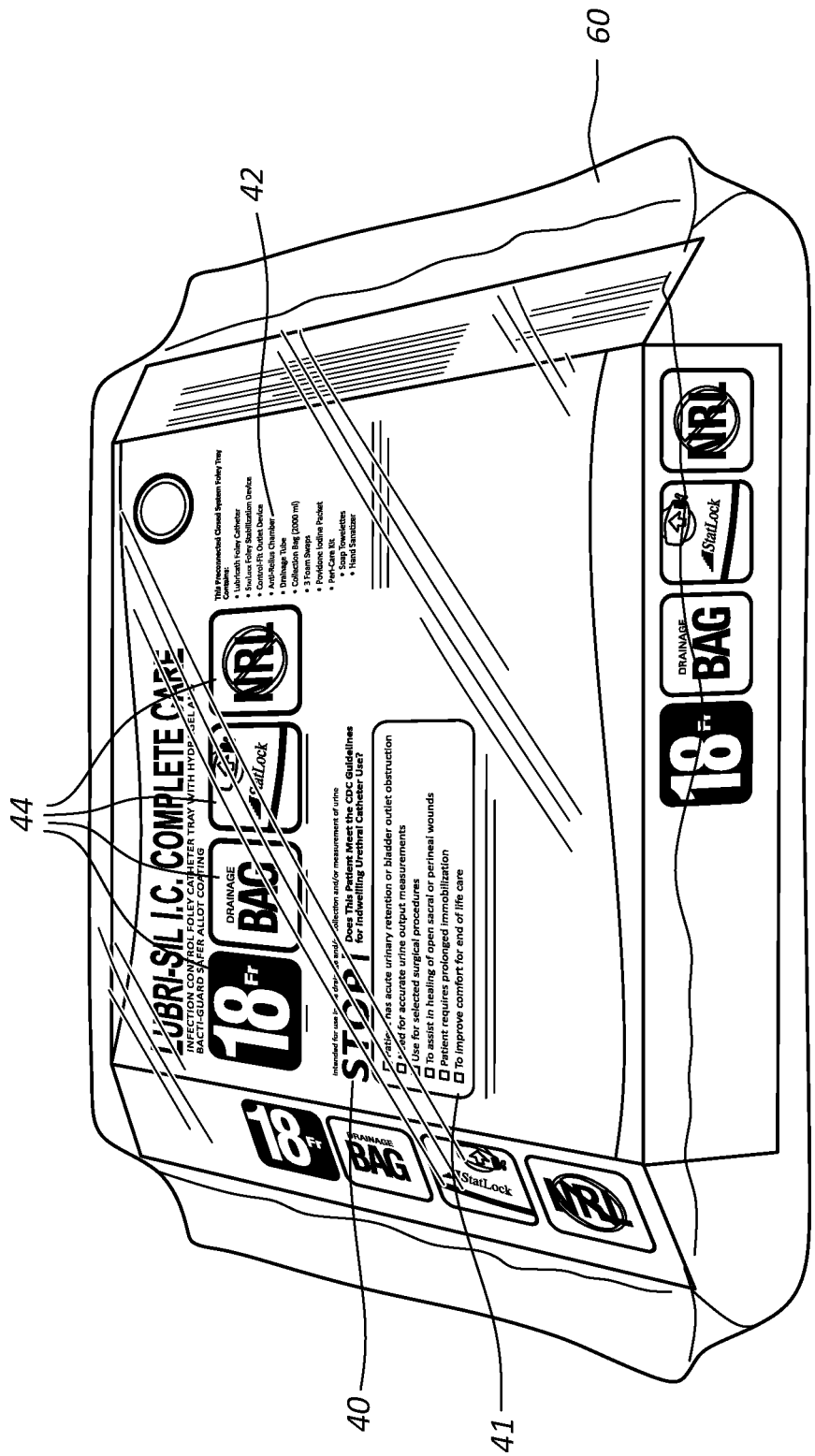
FIG. 9 shows a top view of an exemplary catheterization package sealed in a sealed bag and having a packaging label with information squares on a top and two sides thereof, the sides providing for easy viewing even if the catheterization package were in a stack of other catheterization packages.
Figure 10:
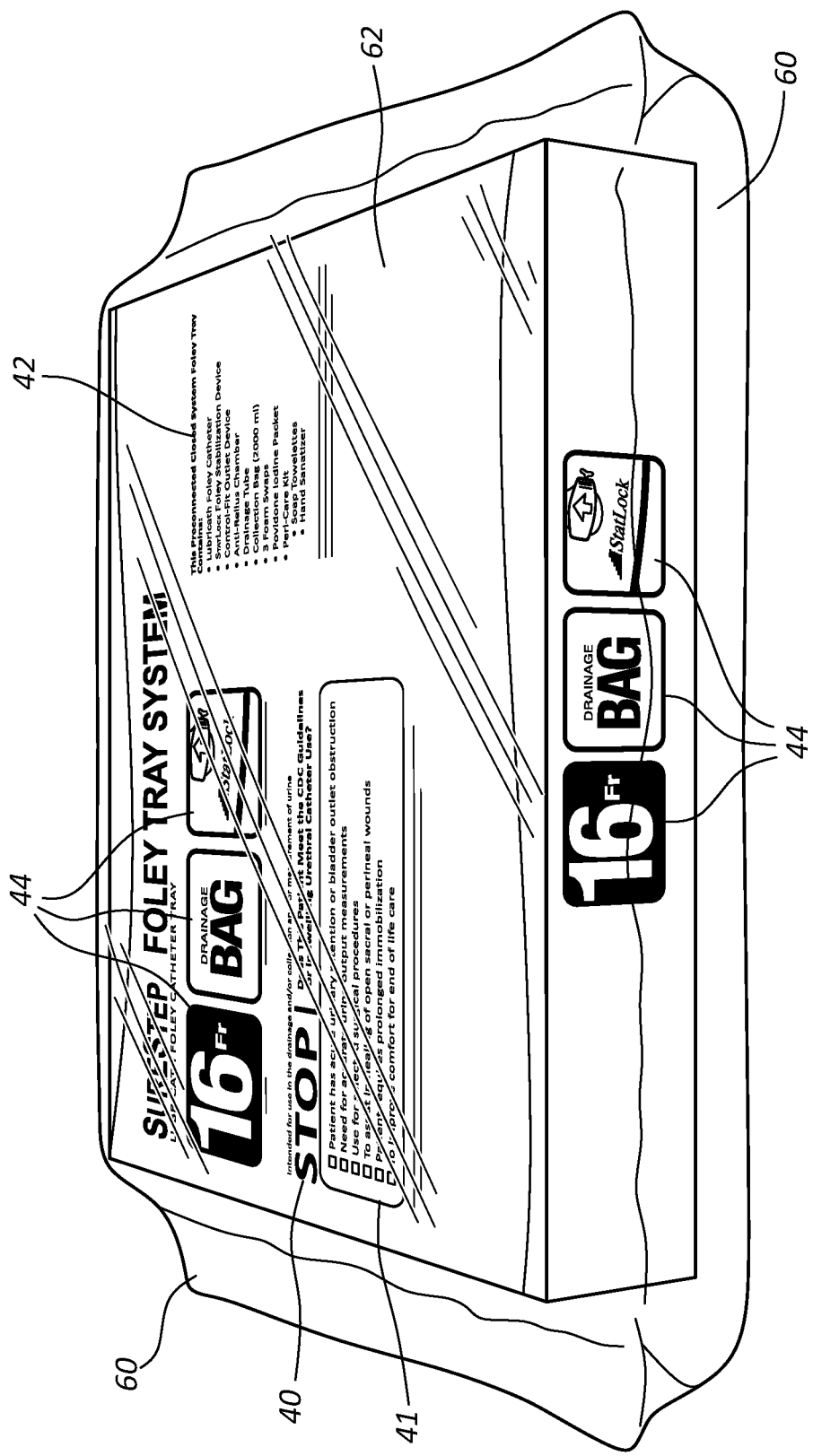
FIG. 10 shows a top, front perspective view of another exemplary catheterization package (different from that shown in FIG. 9) sealed in a sealed bag and having a packaging label with information squares on a top and two sides thereof (one side of which is visible), the sides providing for easy viewing even if the catheterization package were in a stack of other catheterization packages.
Figure 11:
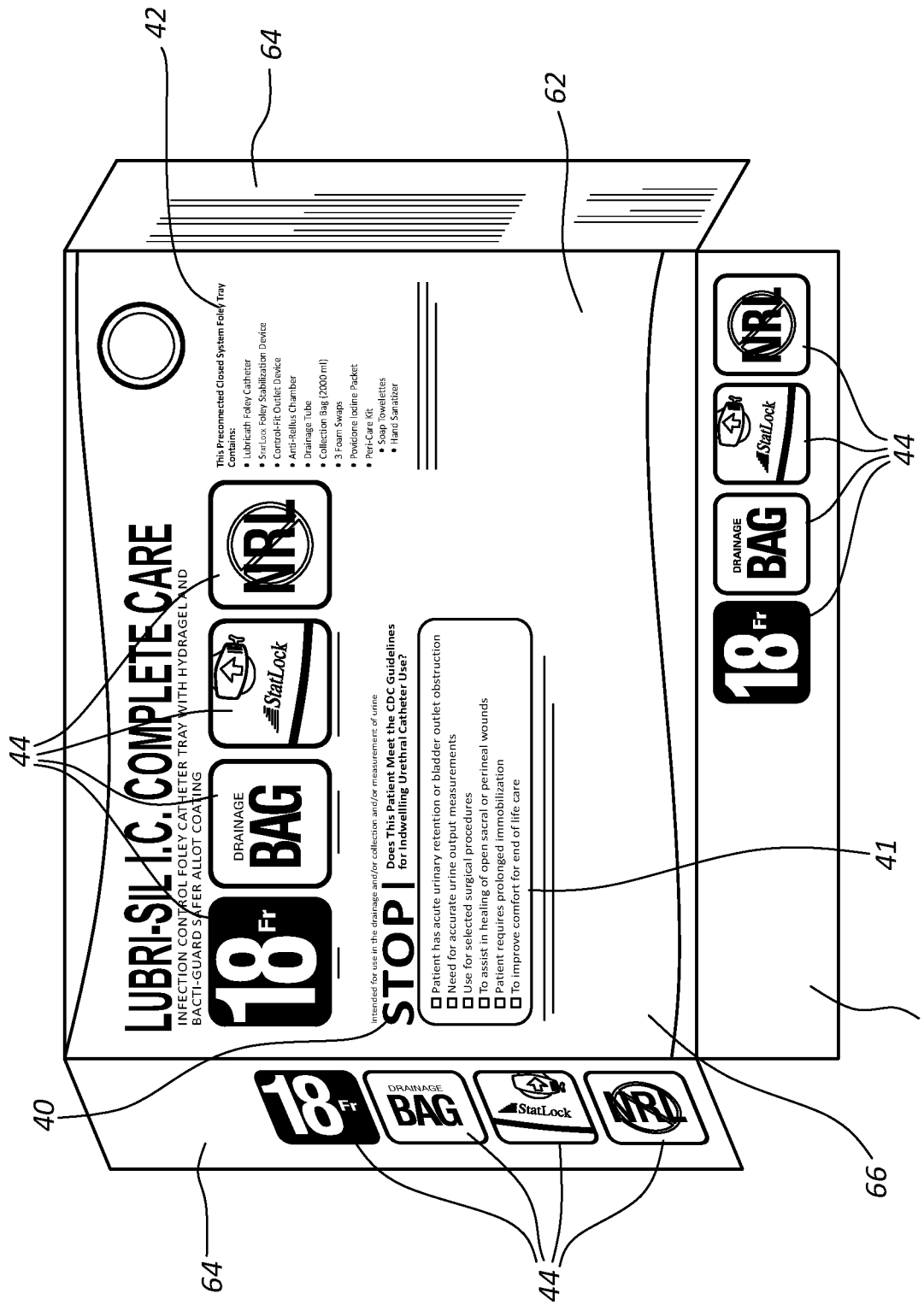
FIG. 11 shows a top view of the exemplary catheterization package of FIG. 9 outside of the sealed bag, but still having the same packaging label thereon.
Figure 12:
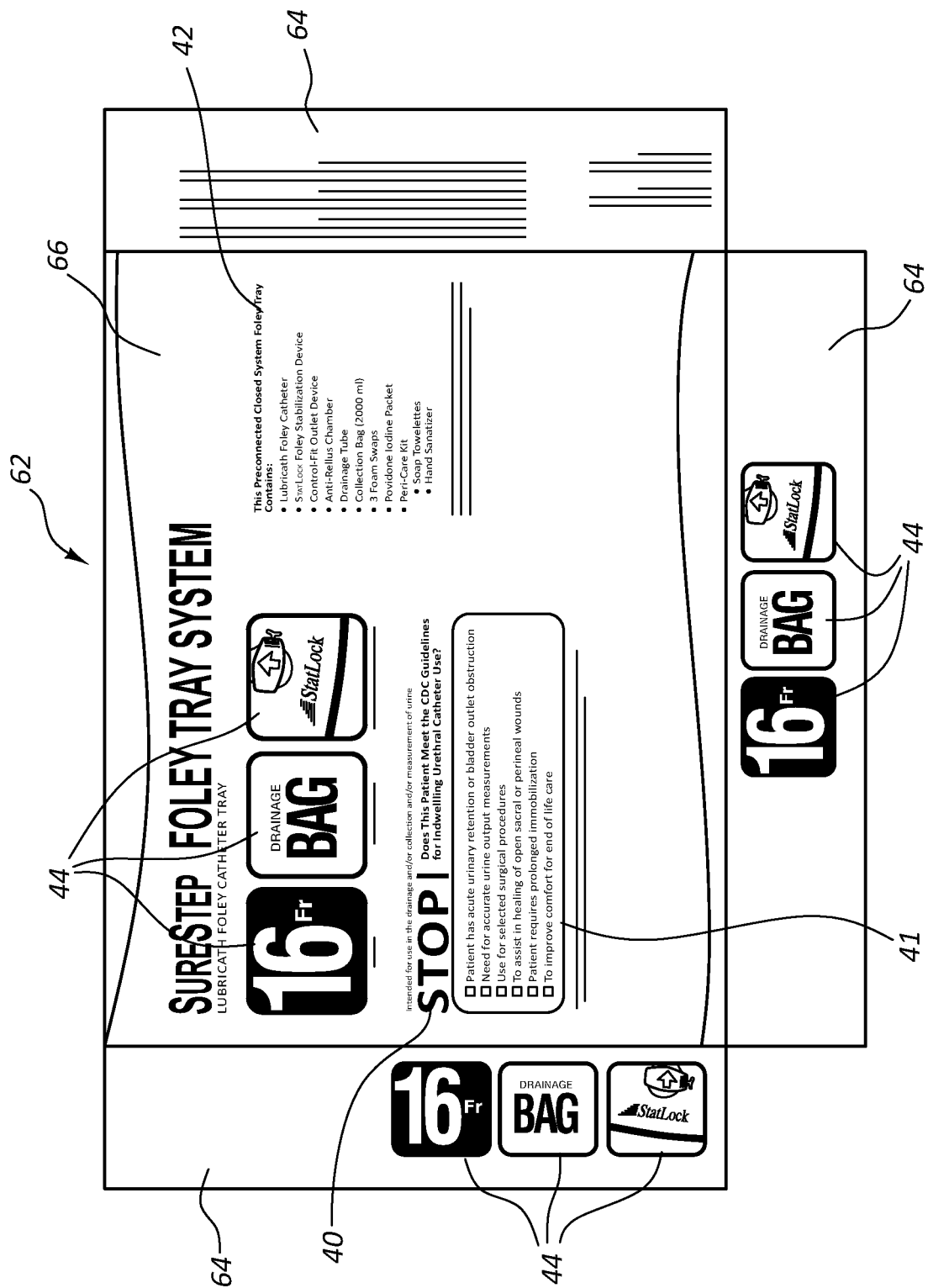
FIG. 12 shows a top, flattened view of the packaging label of the exemplary catheterization package of FIG. 10 including lines added to show where the sides may be folded when placed over other components of a catheterization package prior to sealing the catheterization package in a sealed bag.

First, a catheterization package as shown, for example, in FIGS. 9 and 10 may be provided (e.g., a health care provider/clinician may obtain or select the catheterization package from shelf or through a purchase, or may place the catheterization package in the hospital room where the patient is waiting for catheterization.) As can be seen in FIGS. 9 and 10, the catheterization package may be sealed, e.g., by an outer container 60 (e.g., a sealed bag) surrounding the other contents of the catheterization package, such that the contents remain sterile and properly contained. Just inside the sealed bag (or other external container), a paper or cardboard packaging label 62 may be included in the catheterization package. The external container 60 (or sealed bag) may be transparent, or at least partially transparent, such that a clinician may see the label 62 or portions of the label. The label 62 may include sides 64 that are foldable such that they extend down the sides of the catheterization package. The label may include one, two, three, or four sides. For example, FIGS. 11 and 12 each show a label 62 that a large top portion 66, and 3 smaller sides or side portions 64 foldable to a different plane from the plane in which the large top portion 66 resides. Lines on FIG. 12 show where the folds may be made to form the sides or side portions. In one embodiment, the label has four sides or side portions 64 instead of three.

The packaging label 62 may include instructions and or other information thereon. For example, the label 62 may include initial instructions for catheterization. The label 62 may include a logo, trademark, or product name printed or otherwise included thereon, e.g., "SureStep™ Foley Tray System", "Lubri-sil® I.C. Complete Care®", and/or "BARD." The label 62 may also, or alternatively, include instructions related to the catheterization written thereon. For example, the label may include instruction(s) 40 to verify whether the patient meets the CDC guidelines for indwelling urethral catheter use, as shown in the bottom left quadrant of the top portion 66 of the labels 62 in FIGS. 9-12. The label may include a checklist 41 to verify the different factors that qualify a patient for indwelling urethral catheter use under the CDC guidelines, e.g., as also shown in the bottom left quadrant of the top portion 66 of the labels 62 shown in FIGS. 9-12. The label 62 may also include a list of components 42 of the catheterization package as shown on the right side the top portion 66 of the labels 62 in FIGS. 9-12. The instructions or other information may be in upper case letters, in bold, or otherwise called out for greater visibility to ensure the clinician reads the instructions or other information.

The packaging label 62 may also include key information or variables called out in a simplified and easy-to-read manner. For example, visual identifiers, squares, other shapes, and/or other features may be included that each have an indicator of one key piece of information or variable called out and easy to read. In FIGS. 9-12, the labels 62 are shown as including information squares 44 that each includes an indicator of one key piece of information about the catheterization package. Information squares 44 essentially isolate and feature particular information about the catheterization tray from a range of possibilities or variables. Various features or variables may be called out, including: (1) whether the tray includes a drainage bag or a urine meter, (2) the French size of the catheter, (3) the type of catheter included, (4) the substrate type of materials used in the catheter or other components, e.g., latex or latex-free, (5) special components or features, e.g., inclusion of a StatLock® securement device, inclusion of special infection control coating, or other features. This calling out of particular variables, separated from everything else, allows the health care provider to see what is in the catheterization package or tray at a glance. Accordingly, the health care provider can quickly determine what the key distinguishing elements of the catheterization package or tray are. For example, if the catheterization package shown in FIG. 9 and the catheterization package in FIG. 10 were both stored on the same shelf, a health care provider could quickly tell the major differences between the catheterization packages just by looking at the information squares 44. One can readily tell from the information squares 44 in FIG. 9 that the catheterization package in FIG. 9 includes an 18 French sized catheter, a drainage bag, Bard's StatLock®, and is a non-latex catheter. One can readily tell from the information squares 44 in FIG. 10 that the catheterization package in FIG. 10 includes a 16 French sized catheter, a drainage bag, and Bard's StatLock®.

Further, the packaging label 62 may be designed to be visible in multiple planes. The label may be designed to fold at the edges of the catheterization package such that the label (or a portion of the label) forms sides or side portions that are visible when the catheterization package is viewed from the sides, in addition to being visible from the top. In FIGS. 9-12, the labels 62 are designed such that information squares 44 are visible from the top of the catheterization package, and at least two sides of the tray. Optionally, the label may also be designed such that information squares 44 appear on all the sides of the catheterization package (e.g., on three sides or four sides). Accordingly, anyway you stock the catheterization package, you can see the label. Further, multiple catheterization packages may be stacked on top of each other, but because of the information squares on one or more sides of the catheterization package, a clinician can still quickly tell from the sides of the packages in the stack which catheterization package from the stack is the one desired for a particular patient.

The catheterization package may be selected based on the information squares 44, e.g., after reviewing the information squares 44. After providing/obtaining/selecting the catheterization package, the user may open the container (e.g., the sealed bag) and remove it from around the remainder of the catheterization package. After the container (or sealed bag) has been removed the remainder of the catheterization package looks, for example, as shown in FIG. 11.

The user may then remove the label 62 and set it aside to reveal other components that were underneath the label 62. For example, when the label is removed from the catheterization packages shown in FIGS. 9-11, detailed instructions for catheterization or the directions for use document 68 of the catheterization package or tray may be revealed as shown, for example, in FIG. 13. Detailed instructions and/or information on safety considerations are thereby one of the first items accessed in the catheterization package. Providing detailed instructions up front allows the user/clinician/health care provider to review the entire procedure in advance of any other steps and before breaking the sterile field formed by the CSR wrap around the catheterization tray. This helps the procedure to run more efficiently and safely. Pages of exemplary detailed instructions may be seen on various pages of document 68 in FIGS. 14A-14D. All the steps contained in FIGS. 14A-14D may be performed as an exemplary catheterization method or procedure.

Additionally, there may also be associated patient education information whether attached to the detailed instructions or separately placed in the catheterization package. The patient education information may be used by a health care provider to instruct the patient on care of the indwelling catheter and may, ultimately, be given to the patient for reference. FIGS. 15A and 15B show an example of patient education information that may be included on a patient sheet/pamphlet 70 in the catheterization tray. FIG. 15A shows a first side of the patient education information sheet 70 in English, whereas FIG. 15B shows a second side of the patient education information sheet 70 in Spanish.

Figure 16:
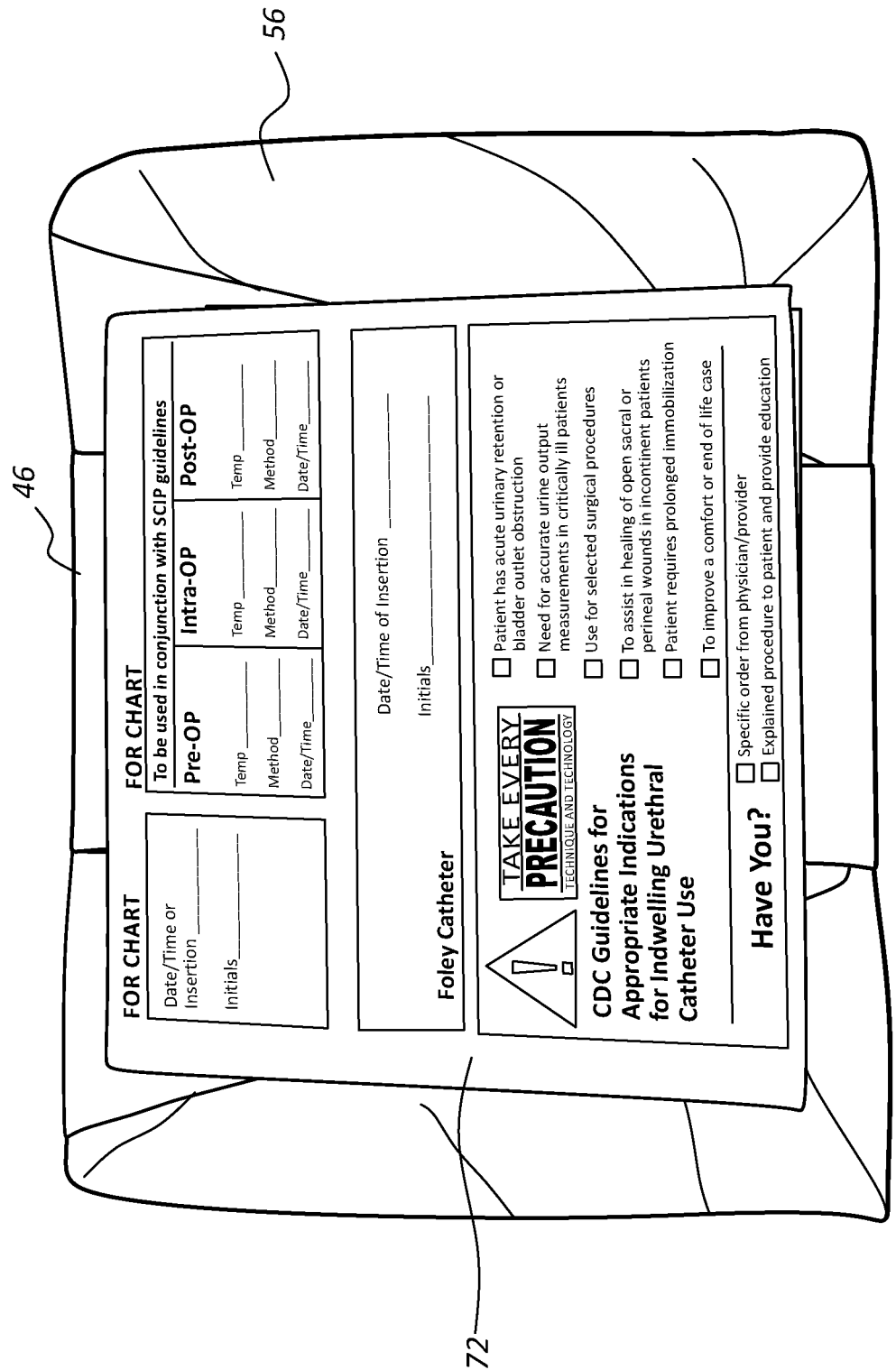
FIG. 16 shows a top view of the exemplary catheterization package of FIG. 13 without the exemplary detailed instructions/procedural indicators document or directions for use (DFU) document, and showing an exemplary label or insert sheet thereon.

Underneath the detailed instructions or directions for use document, the catheterization package may include a checklist of safety considerations/steps, a patient information chart, or an insert sheet including safety consideration/steps and a patient information chart combined on the same insert sheet. FIG. 16 shows and exemplary insert sheet 72 on which patient information can be recorded or charted and including safety information. This insert sheet 72 may be accessed after the detailed instructions are removed from the package. It may be beneficial to have an insert sheet 72 in this location to do one last safety check prior to treating the patient and to have important patient information at hand. The insert sheet 72 may be configured as a sticker label, e.g., the insert sheet 72 may include a backing that protects a sticker adhesive, and when the backing is removed, the insert sheet 72 may be stuck to a file or chart associated with the patient.

Figure 17:
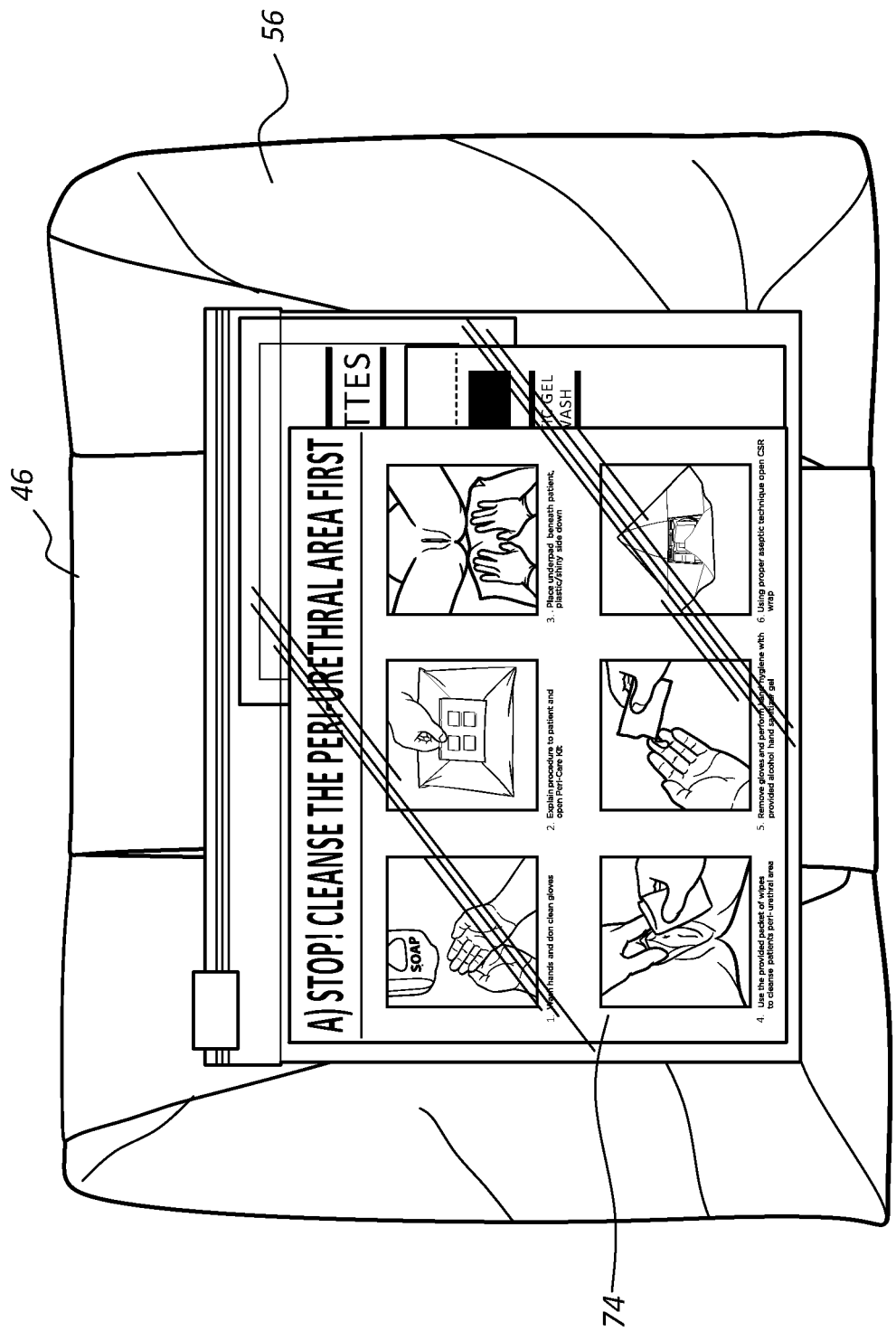
FIG. 17 shows a top view of an exemplary catheterization package (e.g., similar to the exemplary catheterization package of FIG. 16) without the exemplary label or insert sheet, and showing an exemplary perineal care or peri-care kit/packet thereon.
Figure 18:
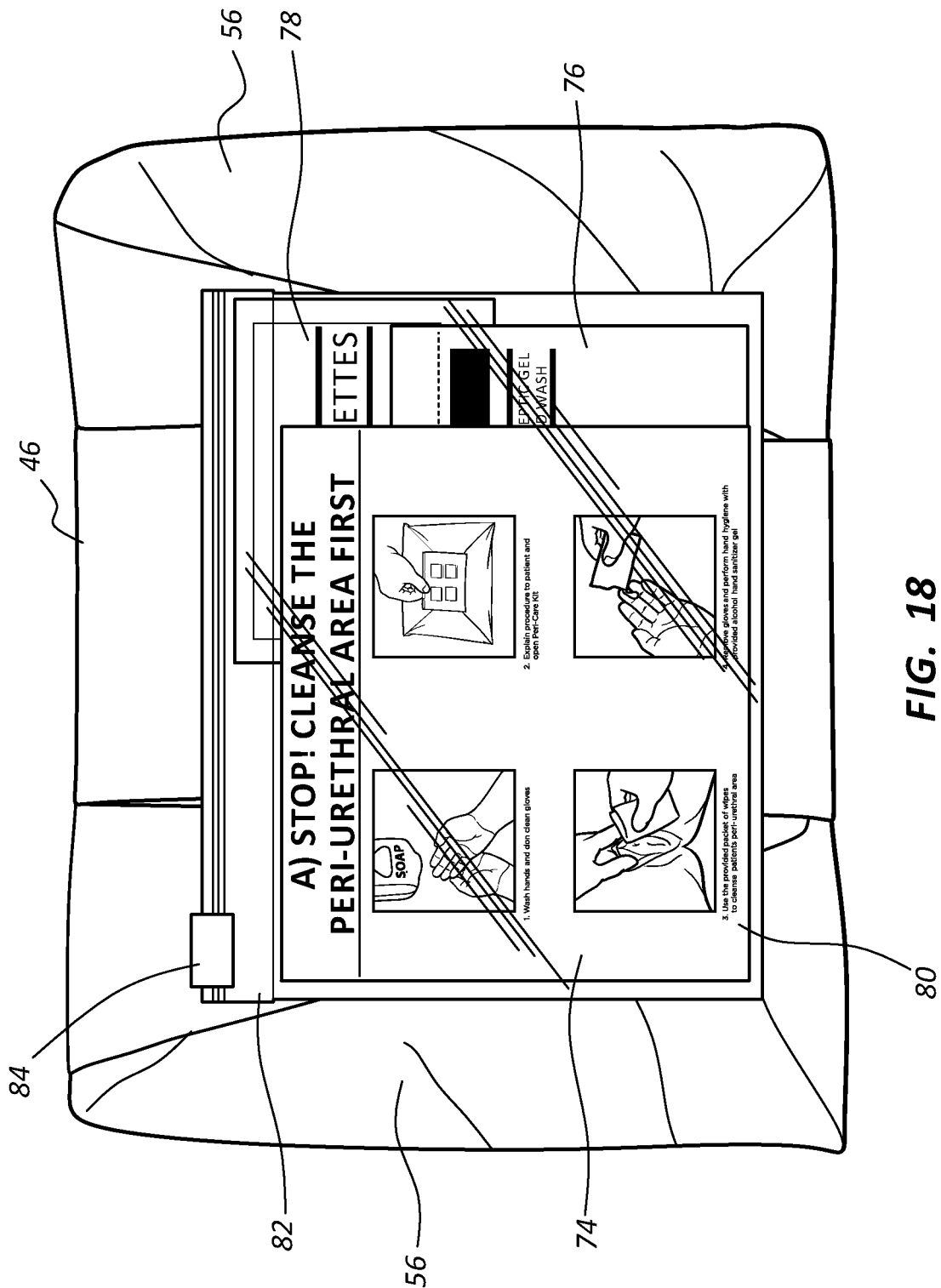
FIG. 18 shows a top view of an exemplary catheterization package (e.g., similar to the exemplary catheterization package of FIG. 16) without the exemplary label or insert sheet, and showing another, different exemplary perineal care or peri-care kit/packet thereon.
Figure 19:
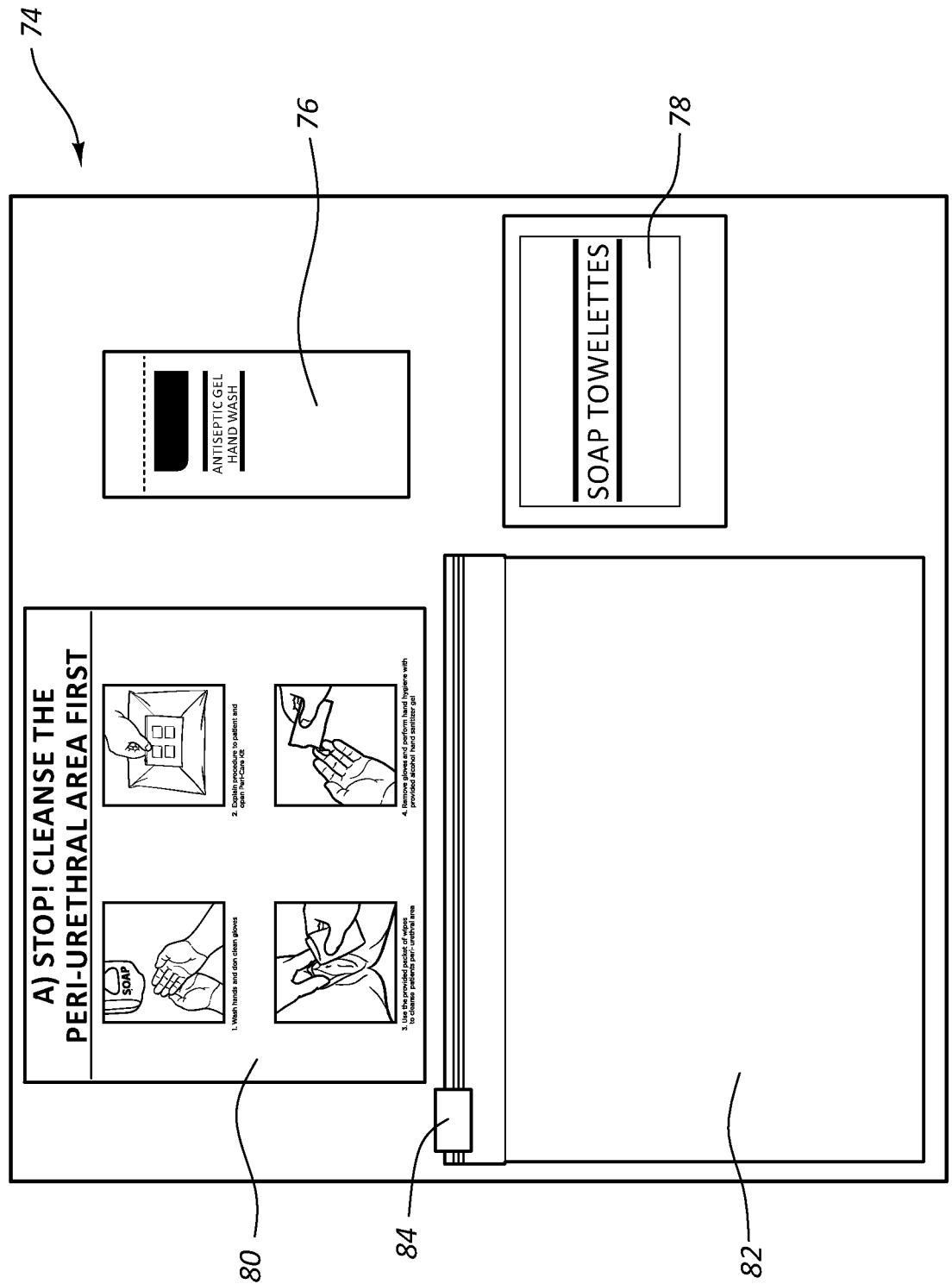
FIG. 19 shows a separated view of the components of the exemplary perineal care (or peri-care) kit or packet of FIG. 18.

After removing the detailed instructions 68 and the insert sheet 72 from the catheterization package, a perineal care (or peri-care) packet or kit 74 is revealed, as shown in FIGS. 17 and 18, and may be accessed. A peri-care kit is helpful to provide an initial cleaning of the area where the catheterization takes place prior to using an iodine solution to further cleanse and sterilize the area. This is especially true for patients who are very dirty and must have an initial cleaning before the iodine solution will be most effective. The peri-care kit may include any items helpful for an initial cleaning of the patient's perineum or for perineum care in general. For example, as shown in FIGS. 18 and 19, the peri-care kit may include hand sanitizer 76 (e.g., antiseptic gel hand rinse) for the health care provider to sterilize his/her hands, moist towelettes 78 (e.g., a package of castile soap towelettes), instructions/procedural indicators 80 (e.g., instructions/procedural indicators for health care provider and/or instructions for patient). The hand sanitizer may be designed to have improved efficacy and/or to enable single-handed usage.

As shown in FIGS. 17-19, the items of the peri-care kit may be included in a bag 82 (e.g., a zip lock baggy) or other package to keep the items/components together. In one embodiment, the bag type used is a baggy including a zipper 84. It has been found such a bag type is easier to open with gloves on rather than, for example, a bag without a zipper or a bag that must be opened by tearing. However, a bag with perforations on the bag instead of a zipper or zip-lock feature is also contemplated, as such may be cheaper to manufacture.

Exemplary peri-care instructions/procedural indicators 80 are shown in FIGS. 17-19. The instructions 80 may inform a health care provider to: "1. Wash hands and don gloves," "2. Explain procedure to patient and open Peri-Care kit," "3. Use the provided packet of towelettes to cleanse the patient's peri-urethral area," and "Remove gloves and perform hand hygiene with provided alcohol hand sanitizer gel." Other instructions/procedural indicators are also possible. The exemplary method may include performing some or all of the four steps recited above as steps on the instructions.

The exemplary method may proceed in three main stages, i.e., (A) the initial peri-care stage, (B) the catheterization stage, and (C) the catheter care and maintenance stage. Each of these stages is denoted on the instructions/procedural indicators and/or other materials with a large "A" "B" or "C" to signify the different main stages. As can be seen on the peri-care instructions 80, there is a large "A" at the top of the instructions/procedural indicators to indicate the first stage. As discussed elsewhere herein, the belly band 46 includes a large "B" to indicate the second stage, and the main compartment 1 of the catheterization tray includes a large "C" to indicate the third stage.

Figure 20:
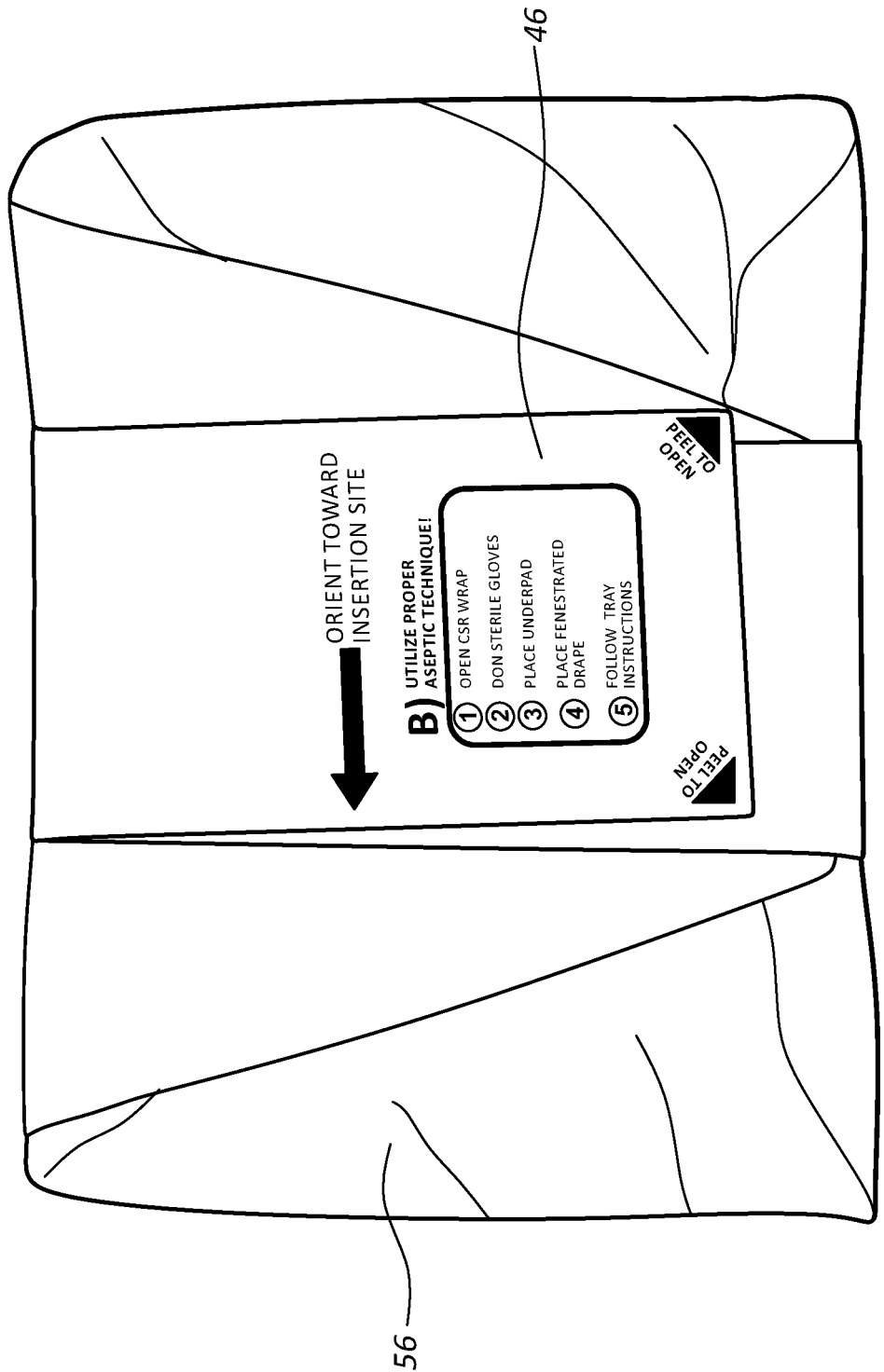
FIG. 20 shows a top view of an exemplary catheterization package (e.g., similar to the exemplary catheterization package of FIG. 17 or FIG. 18) without the perineal care (or peri-care) kit or packet, and showing a belly band including instructions/procedural indicators thereon.
Figure 30A:
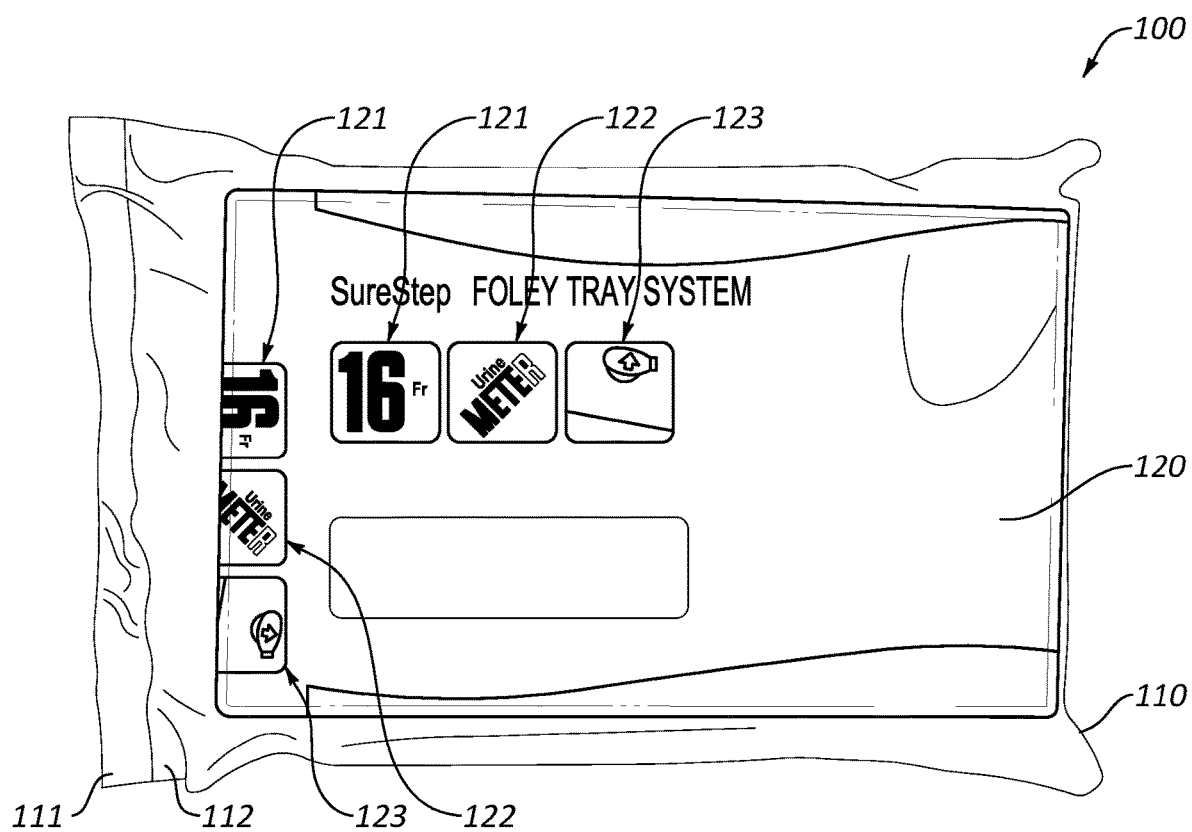
FIG. 30A is a top view of an exemplary catheterization system.
Figure 30B:
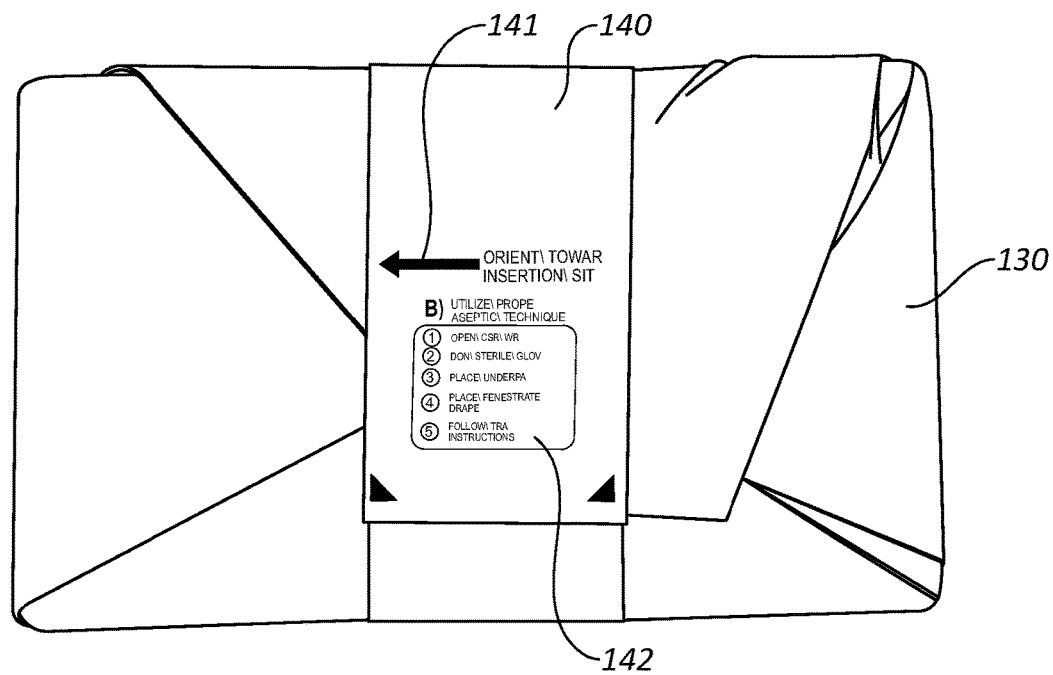
FIG. 30B is a top view of a catheterization tray of the exemplary catheterization system of FIG. 30A, which is wrapped in a wrap.

After removing and using the peri-care kit, a belly band/indicator wrapper 46 may be revealed as shown in FIG. 20 (see also indicator wrapper 140 in FIG. 30B). The belly band 46 may circumvent the tray in at least one direction. The belly band 46 may help to keep the CSR wrap intact and maintain the sterile barrier. The belly band 46 may also help to keep all the contents inside the tray, so the items do not move around.

The belly band/indicator wrapper 46 may include instructions/procedural indicators and/or other information thereon. For example, as shown in FIG. 20 (see also FIG. 30B), the belly band may include an instruction/procedural indicator telling the health care provider how to orient the tray relative to the patient. For example, the belly band may say, "orient toward insertion site" and have an arrow pointing to the end of the catheterization tray that should be positioned closest to the patient's perineum and urinary tract. This ensures that the tray is properly positioned for most logical and intuitive use when the CSR wrap is opened.

Further, as shown in FIG. 20 (see also indicator wrapper 140 in FIG. 30B), the belly band 46 may include instructions/procedural indicators to "utilize proper aseptic technique," "(1) Open CSR Wrap," "(2) Don Sterile Gloves," "(3) Place Underpad," "(4) Place Fenestrated Drape," and (5) "Follow Tray Instructions. These instructions/procedural indicators include a large "B" at the top to signify that these instructions/procedural indicators are part of the second stage or catheterization stage. The instructions/procedural indicators inform the health care provider to open the CSR wrap and perform other steps once the CSR wrap is opened. Providing this information before breaking the sterile barrier gives the health care provider a preview of the procedure, and ensures he/she is prepared when the sterile barrier is broken by opening the CSR wrap. Optionally, a label or sticker may be used instead of a belly-band, which may provide the same information as the belly band described herein.

Figure 21:
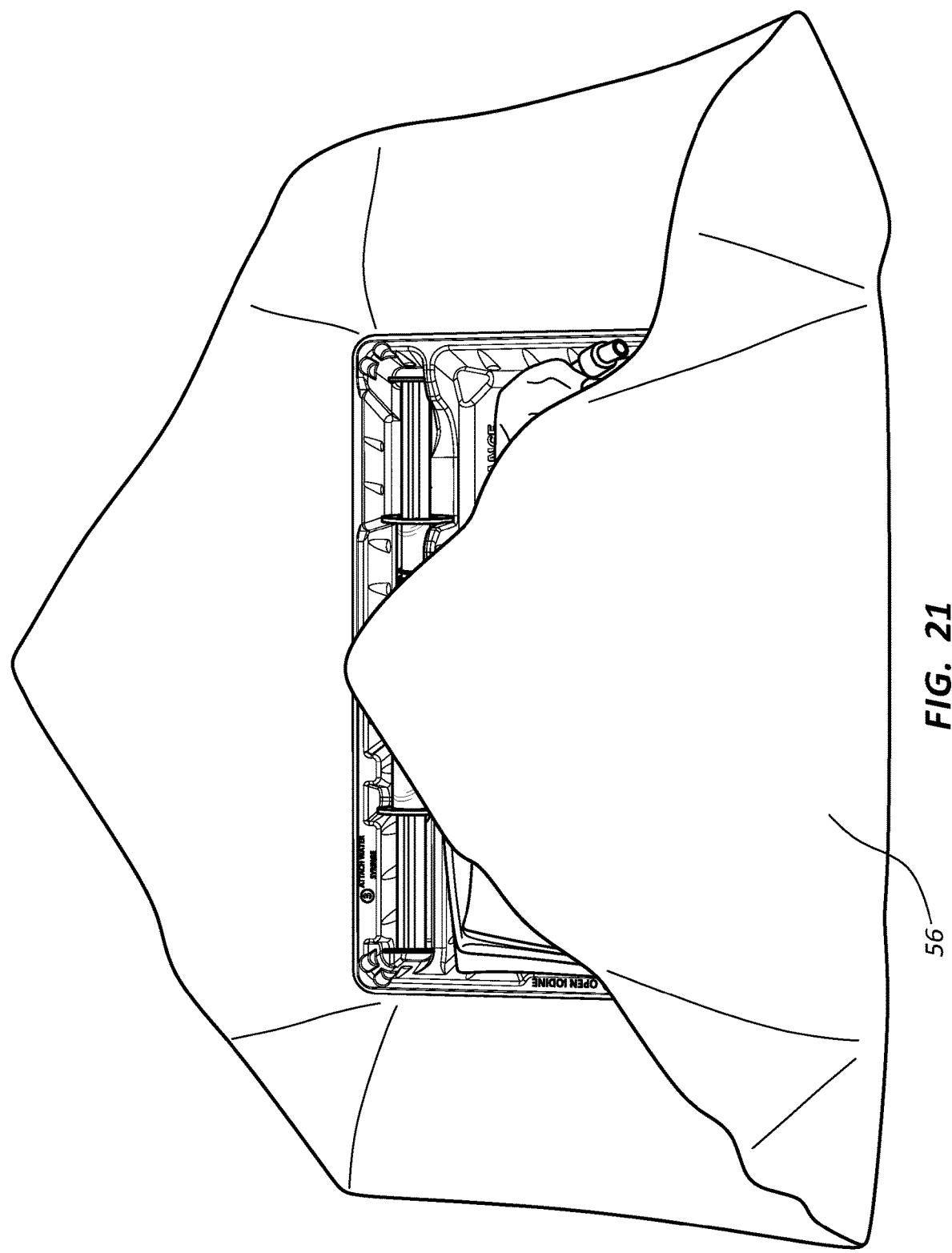
FIG. 21 shows a top view of an exemplary catheterization package (e.g., similar to the exemplary catheterization package of FIG. 20 or FIG. 21) without the belly band, and showing the sterile wrap only partially folded/wrapped around an exemplary catheterization tray.

Once the tray is oriented and the health care provider has read the belly band instructions/procedural indicators, the next step is to open and/or remove the belly band. After removing the belly band, the sterile wrap 56 (e.g., CSR wrap) may be opened. FIG. 21 shows the catheterization tray with three corners of the sterile wrap 56 unfolded to represent unfolding the sterile wrap 56. Note that until the belly band and sterile wrap are opened, the sterile barrier of the catheterization tray and its components is not broken. This maintains the sterile barrier while the initial peri-care stage is completed and while the tray is properly positioned and oriented for catheterization. By leaving the sterile barrier in tact during the initial steps of the exemplary method, there are fewer opportunities for contamination and the resulting patient infection.

Figure 22:
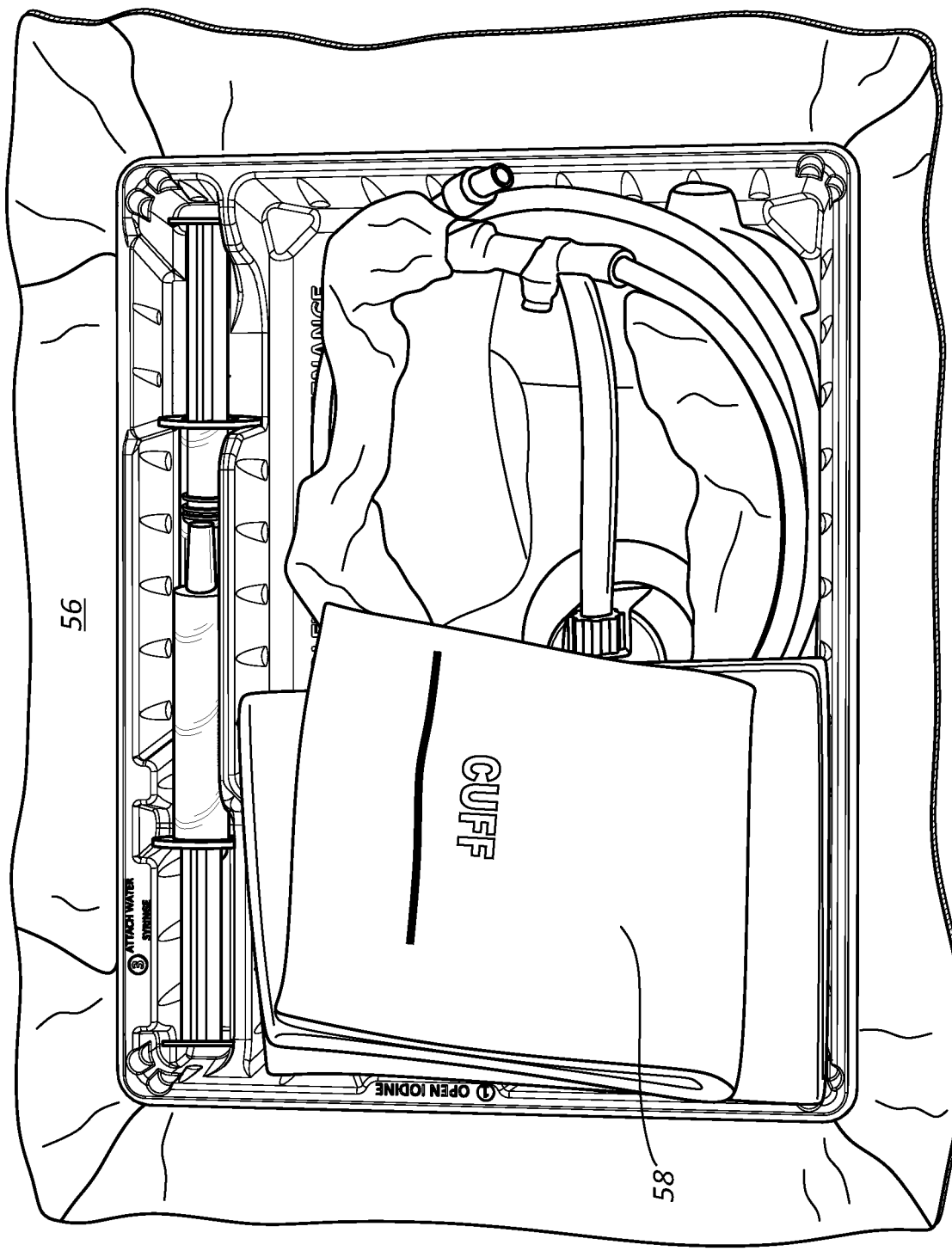
FIG. 22 shows a top view of the exemplary catheterization package of FIG. 22 with the sterile wrap completely unfolded but remaining underneath the catheterization tray, and showing the contents of the exemplary catheterization tray before any components have been removed or, during manufacture/packaging, after all the components to be within the sterile wrap have been placed therein.

If the catheterization tray is oriented as directed by the belly band 46, when the sterile wrap 56 (e.g., CSR wrap) is opened, the tray is properly oriented for logical and convenient use of the catheterization tray and its components. The tray is arranged and ordered for logical step-by-step use as described herein. The initial view of the tray after opening the sterile wrap 56 entirely is shown in FIG. 22. (A breakaway line is used to indicate that the actual edges of the sterile wrap 56 extend beyond the breakaway edges shown in FIGS. 22-29.) Note that the sterile wrap 56 may remain underneath the catheterization tray to form a sterile field for catheterization. The tray shown in FIG. 22 and the other figures are right-hand biased to make use easier for a right-handed health care provider when standing near the lower edge of the catheterization tray with the syringe or catheter compartment positioned furthest from the health care provider (i.e., if the band points toward the genitalia between the legs, the right-handed user stands on the side closest to the patient's right leg). Alternatively, a catheterization tray may be left-hand biased (e.g., essentially a mirror image of the tray shown in FIGS. 22-29 with the mirror placed along the outer wall 7 or along the syringe or catheter compartment).

Figure 23:
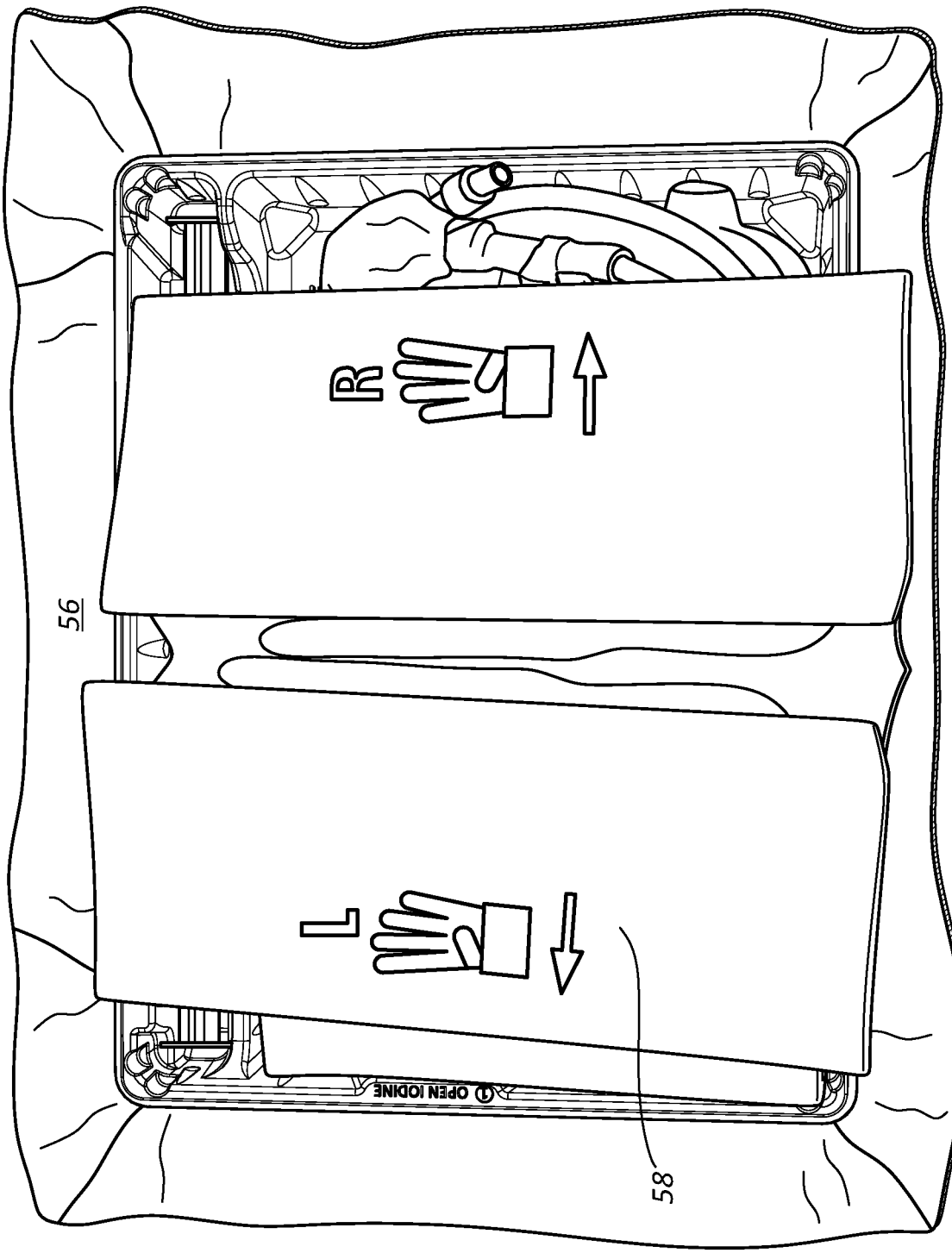
FIG. 23 shows a top view of the exemplary catheterization package of FIG. 23 with a package of sterile gloves partially unfolded and sitting on top of the exemplary catheterization tray.

As instructed on the belly band 46, after first opening the CSR wrap, the health care provider next dons the sterile gloves provided in the tray. As shown in FIG. 22, the top item in the tray after the CSR wrap is opened is a package 58 of sterile gloves (note that the cuff end of the gloves may be indicated on the package 58). The sterile gloves may be made of any material known to be suitable, e.g., latex, rubber, or latex-free materials). This placement of the gloves on top of the tray under the sterile wrap helps the health care provider to intuitively know he/she should don the gloves before proceeding further (because it is intuitive, it may be unnecessary to refer back to the instructions/procedural indicators on the belly band 46). The package of gloves 58 may be opened by folding the cuff down to be closest to the health care provider and then opening the package like a book, as shown in FIG. 23. If opened in this intuitive, logical way, the left hand glove is positioned on the health care provider's left side and the right hand glove is positioned on the health care provider's right side for easy donning of the gloves. A symbol or other indicator may be included on the package 58 to identify the left and right hand gloves as shown, for example, in FIG. 23.

Figure 24:
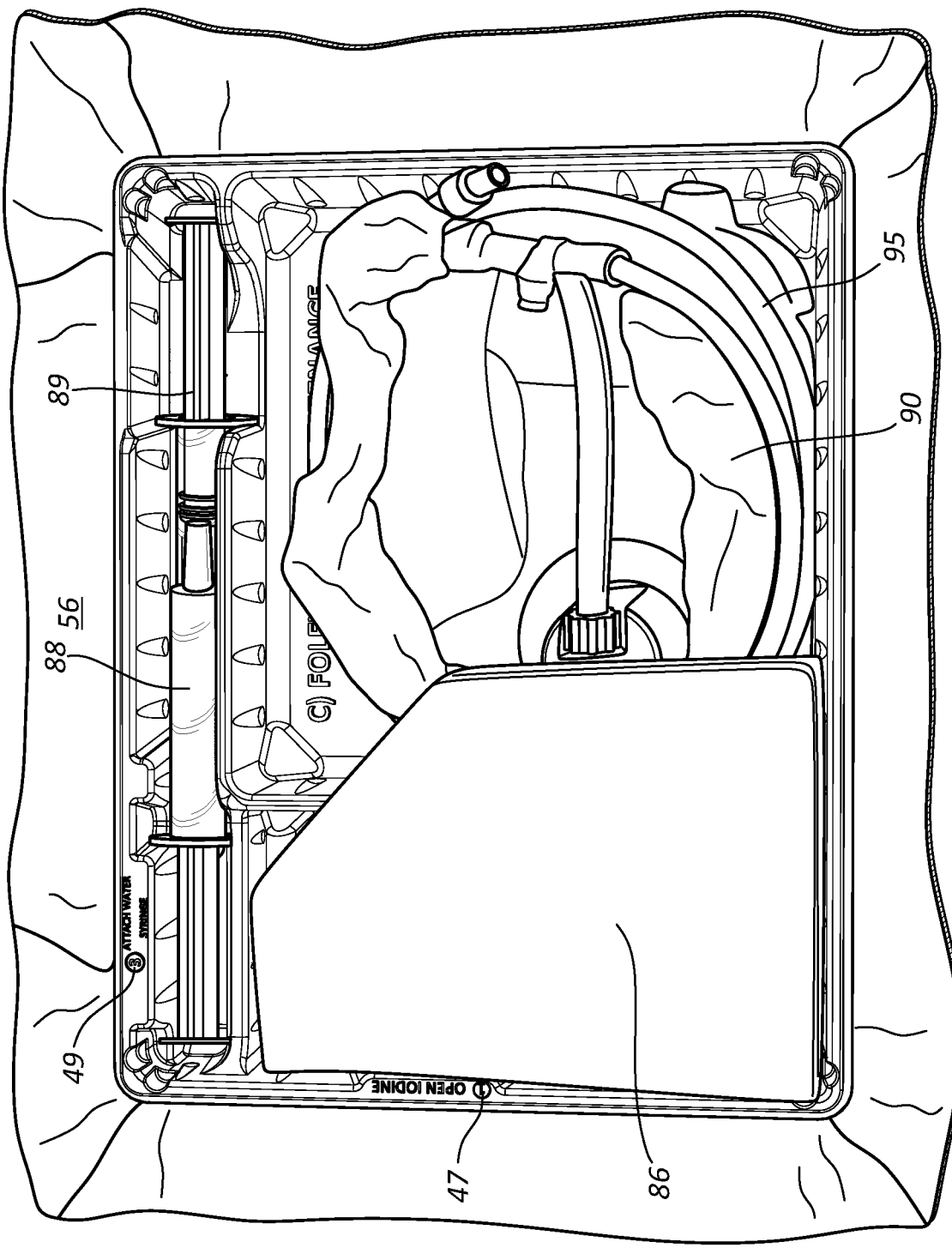
FIG. 24 shows a top view of the exemplary catheterization package of FIG. 24 without the package of sterile gloves, and revealing a pad/drape (representative of a waterproof underpad and/or a fenestrated drape) sitting on top of the exemplary catheterization tray.

As instructed on the belly band 46, after donning the gloves, the health care provider places an underpad under the patient's buttocks. As shown in FIG. 24, once the package of gloves is removed from the tray, the underpad and fenestrated drape are revealed. The folded pad/drape 86 shown in FIG. 24 is representative of: (1) a waterproof underpad, and (2) a separate fenestrated drape. The underpad may have a waterproof side and a liquid absorbent side. If so, the absorbent side is placed up under the patient, and the waterproof side (or plastic side) is placed down. As instructed on the belly band 46, after placing the underpad, the health care provider places the fenestrated drape on the patient such that the genitalia are visible through the central opening in the fenestrated drape. Although the underpad and fenestrated drape are not shown in FIG. 24 as distinct pieces, they are both included in the area of the pad/drape 86, and are arranged such that the underpad is on top of the fenestrated drape (i.e., because the underpad is placed first, which reveals the fenestrated drape for placement thereafter). The fenestrated drape is logically located and folded such that it is intuitive to open the drape away from clinician, which is preferable for how the drape is best used.

Figure 25:
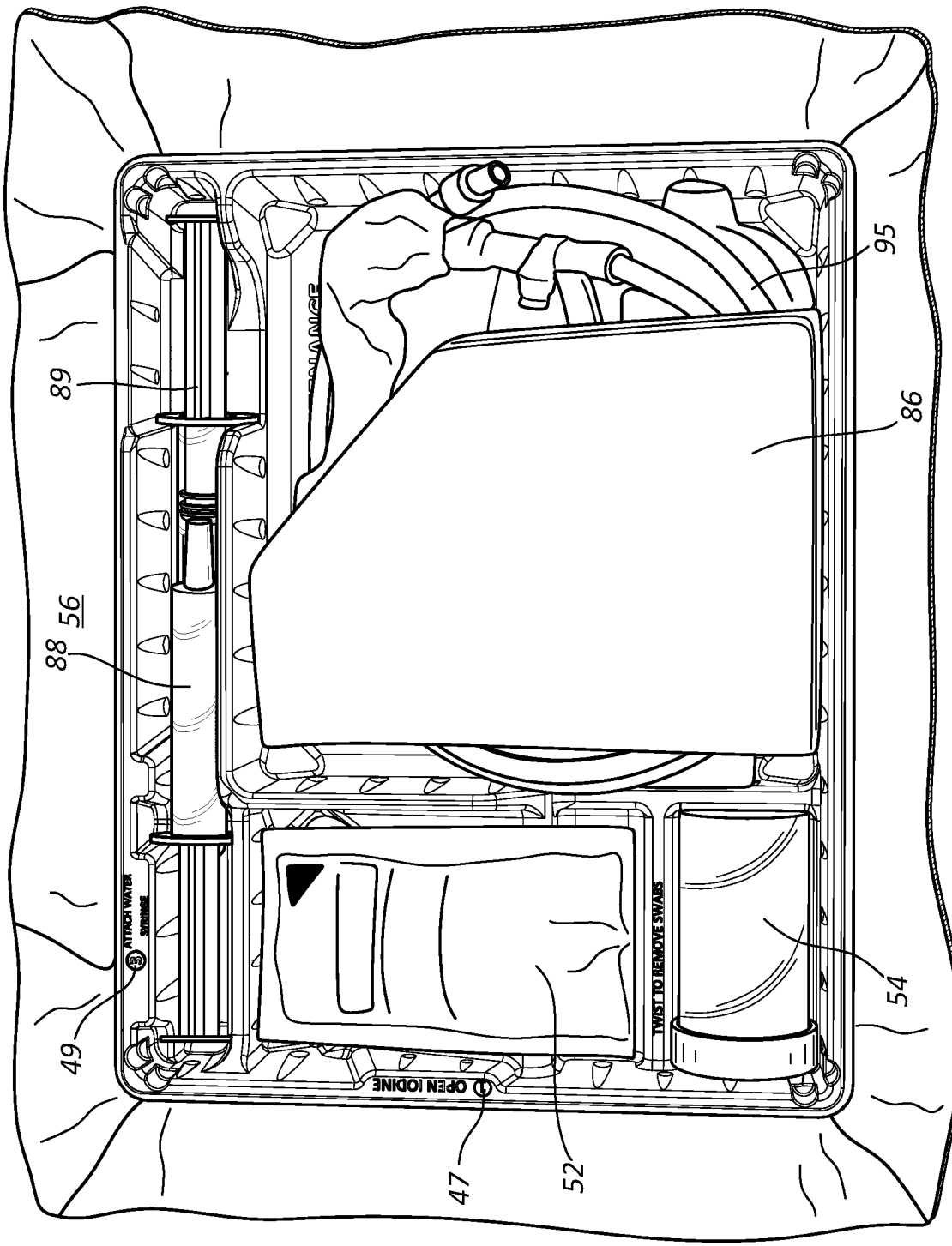
FIG. 25 shows a top view of the exemplary catheterization package of FIG. 25 with the pad/drape moved off the swab compartment, and revealing a packet of sterilizing povidone-iodine solution sitting in the swab compartment and extending over the small storage or overflow compartment of the exemplary catheterization tray.

As instructed on the belly band 46, after placing the fenestrated drape, the health care provider follows the instructions/procedural indicators and/or takes the steps written on the catheterization tray itself. As shown in FIG. 25, removal of the underpad and fenestrated drape reveals a package of sterilizing solution 52 (e.g., povidone-iodine solution). (Note that FIG. 25 shows the fenestrated drape moved from over the swab compartment 3 into the main compartment 1. Moving the drape in this way or placing the fenestrated drape on the patient will reveal the sterilizing solution in the swab compartment.) Further, the first instruction/procedural indicator 47 on the tray (i.e., "(1) Open Iodine"; although, variations on this instruction or other instructions are possible) is visible on the left side of the tray (which is also the side closest to the patient and the region to be catheterized, if oriented as instructed by the belly band 46). Placement of the first instruction 47 on the left is logical because people read English from left to right, and beginning instructions on the left is intuitive (although in countries that do not read left to right, this might be adjusted). Also the instruction/procedural indicator is located close to the sterilizing or iodine solution 52 in the tray, which makes following the instruction/procedural indicator easier and more intuitive.

Assuming the clinician is right-handed, and has oriented the tray as instructed by the belly band 46, the sterilizing or iodine solution 52 is automatically positioned closest to patient. (However, as discussed above, another arrangement is possible where the tray is left-handed biased (e.g., essentially a mirror image of the tray in the figures) such that a left-handed user positioning the tray as instructed by the belly band would also automatically position the sterilizing or iodine solution closest to the patient (e.g., with the left-handed clinician standing on an opposite side of the tray from where a right-handed clinician would stand or on the side closest to the patient's left leg).) Positioning the sterilizing or iodine solution (and the swab compartment) closest to the patient is preferable for the use of the tray. Having the swab compartment 3 and well of iodine solution closest to the patient is beneficial, because it prevents dragging or moving swabs saturated with sterilizing or iodine solution across the tray (which might drip on other components of the tray, if moved over them).

Figure 26:
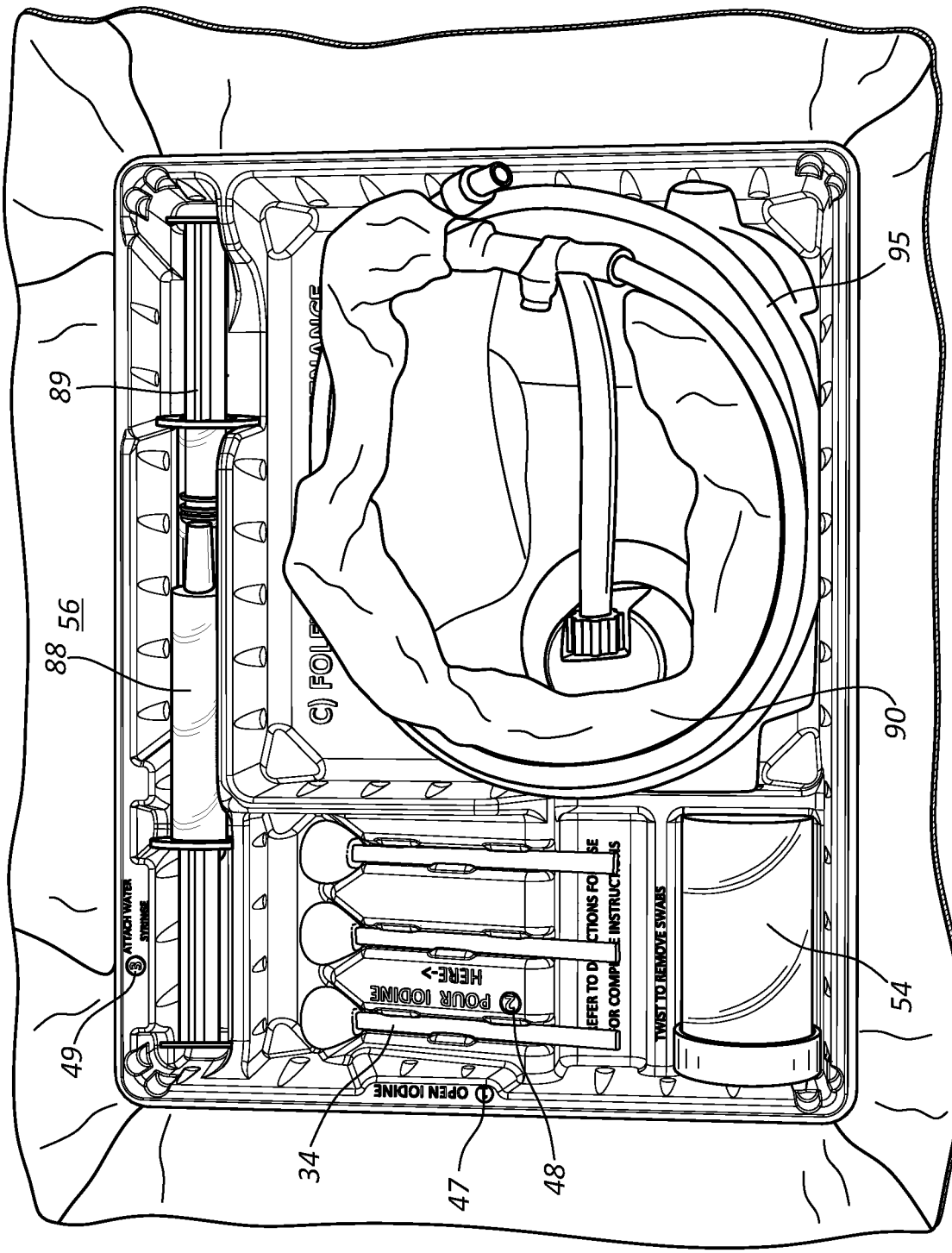
FIG. 26 shows a top view of the exemplary catheterization package of FIG. 26 without the sterilizing povidone-iodine solution, and revealing the swabs or swabsticks in the swab compartment with the proximal ends of the sticks extending over the small storage or overflow compartment of the exemplary catheterization tray.

FIG. 26 shows the catheterization tray after removal of the povidone-iodine solution. Note that removal of the packet of sterilizing or iodine solution 52 reveals the swabs or swabsticks 34 and the second instruction/procedural indicator 48 on the tray. This intuitively leads the health care provider to logically follow the second instruction 48 after picking up the packet of sterilizing or iodine solution. The second instruction 48 on the tray is in the swab compartment 3 and says "(2) Pour Iodine Here-->" and points to the lowest/deepest point or well of the swab compartment 3 (although, variations of this instruction or other instructions are possible). If sterilizing or iodine solution is poured on the barriers or channels of the swab compartment 3, the incline ensures the solution will flow to the lowest/deepest point or well.

Once the health care provider has poured the sterilizing or iodine solution into the well of the swab compartment 3 such that the absorbent heads of the swabs begin absorbing the sterilizing or iodine solution, the health care provider may then attach the syringe of sterile liquid 88 to the inflation port of the catheter 92 (e.g., a Foley catheter) as is instructed by the third instruction/procedural indicator 49. The third instruction 49 is logically located on outer wall 7 of the tray not far from the well of the swab compartment where the health care provider has just poured the sterilizing or iodine solution, and near the syringe of sterile liquid to be used in the third instruction. The third instruction 49 states "(3) Attach Water Syringe" (although, variations on this instruction or other instructions/procedural indicators are possible).

Figure 27:
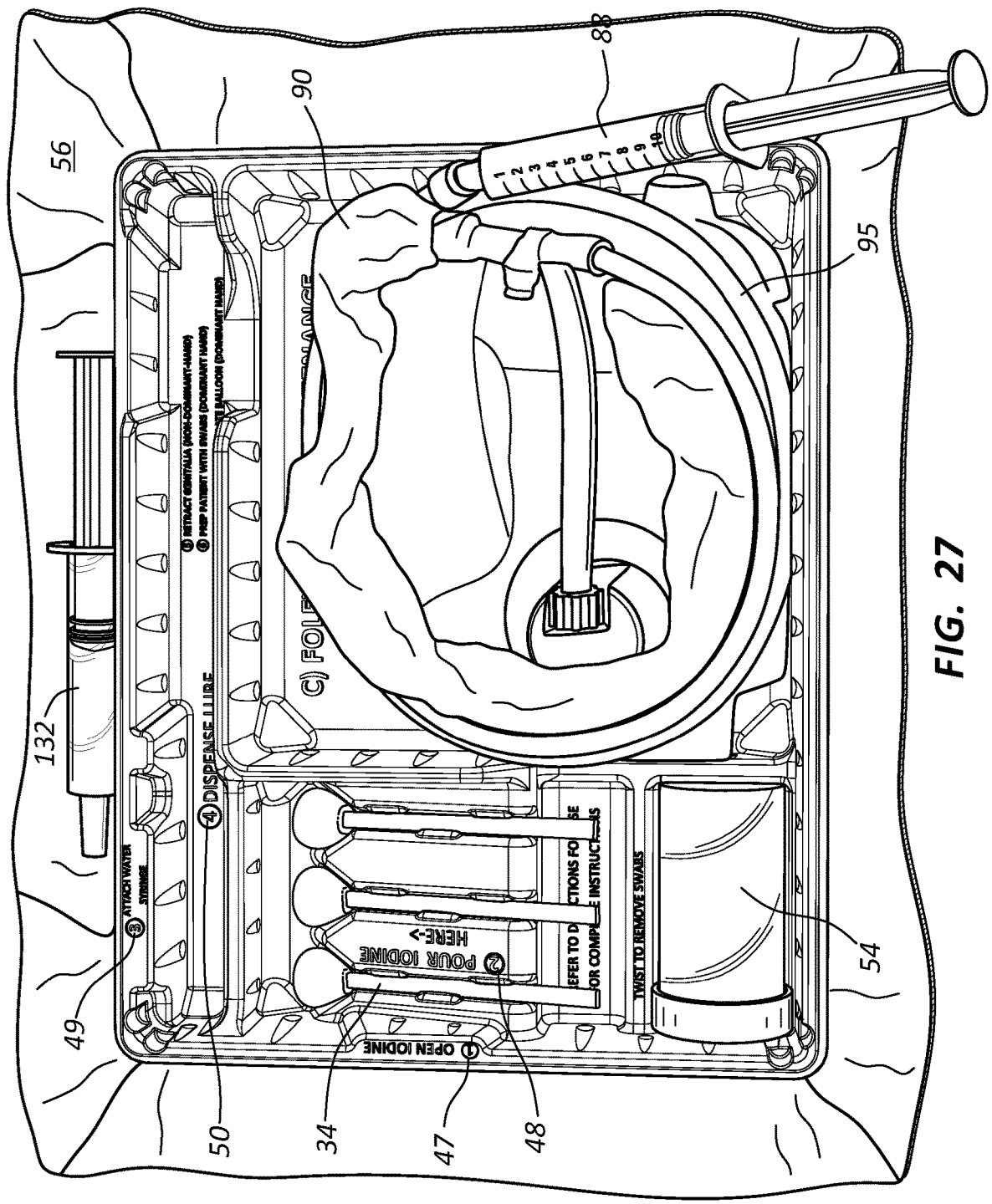
FIG. 27 shows a top view of the exemplary catheterization package of FIG. 27 with the syringe of sterile liquid attached to the inflation port of the catheter.

FIG. 27 shows the syringe of sterile liquid or water 88 after it has been attached to the inflation port of the catheter 92.

Figure 28:
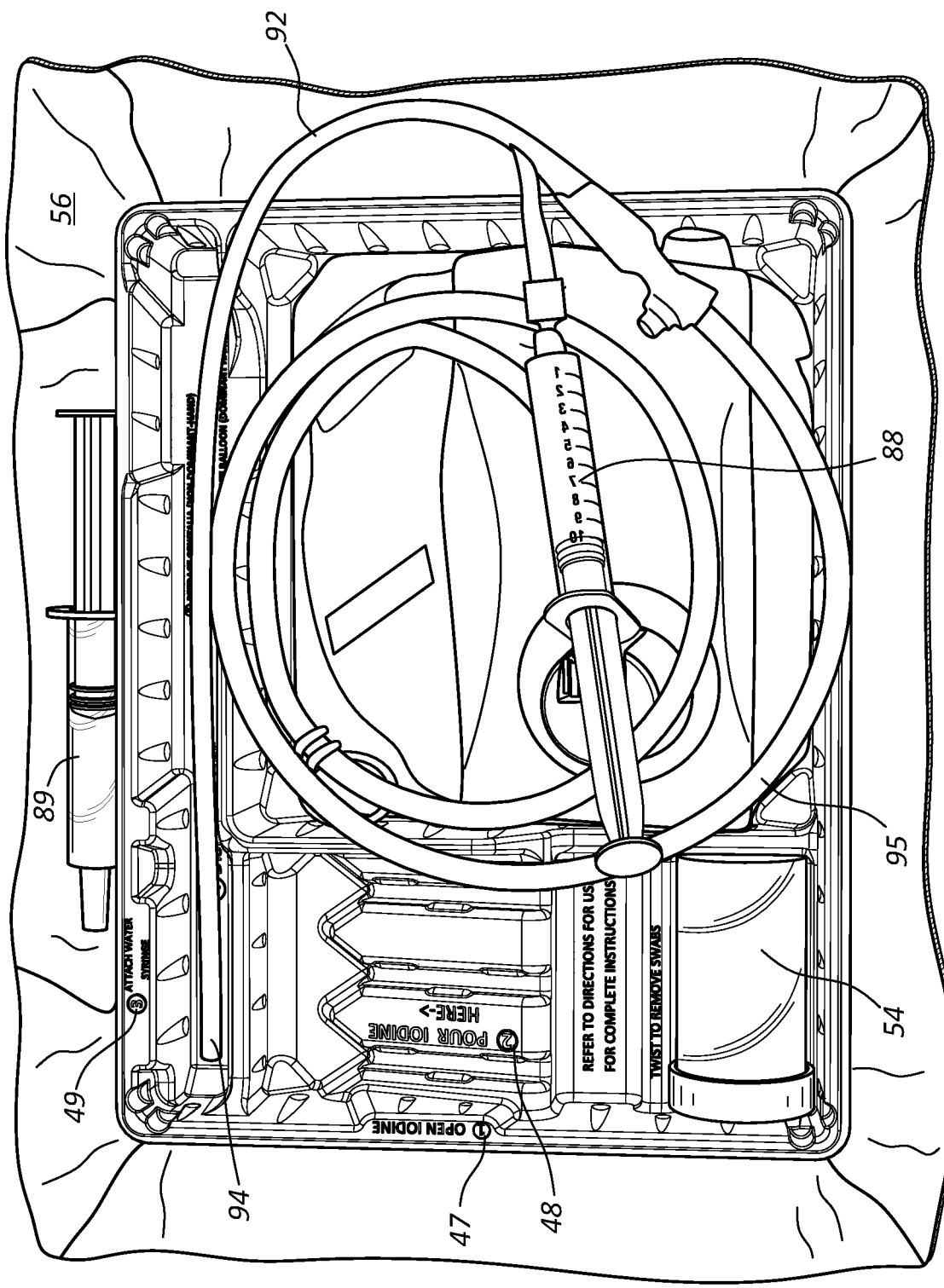
FIG. 28 shows a top view of the exemplary catheterization package of FIG. 28 with a distal portion of the catheter positioned in the syringe or catheter compartment and the syringe of lubricating jelly adjacent to syringe or catheter compartment ready to dispense the lubricating jelly on top of the distal region or distal end of the catheter.

Once the syringe of sterile liquid 88 is removed from the syringe or catheter compartment, the fourth instruction/procedural indicator 50 is revealed (which was previously obscured by the syringe of sterile liquid). The fourth instruction 50 may inform the health care provider to "(4) Lube Catheter" or "(4) Dispense & Lube Foley Here" or something similar (again, variations on this instruction or other instructions/procedural indicators are possible). Indeed, lubricating the catheter is the next step taken by the health care provider. To do so, the health care provider removes the syringe of lubricating jelly 89, which removal reveals the fifth, sixth, and seventh instructions/procedural indicators that were previously obscured by the syringe of lubricating jelly 89. The health care provider can then lubricate the catheter in any way desired. In one embodiment, the health care provider can remove the plastic wrap 90 (shown in FIGS. 27 and 28) from over the catheter 92 (which can be a Foley catheter) and move a portion of the catheter 92 into the syringe or catheter compartment 2, e.g., as shown in FIG. 28. Placing the distal end 94 of the Foley catheter 92 in the syringe or catheter compartment 2 helps to line the catheter 92 up for lubrication and catheterization. For example, as shown in FIG. 28, with the distal end 94 of the catheter 92 positioned near the left-most side of the syringe or catheter compartment 2, the distal end 94 of the catheter 92 is positioned very near the patient and the region to be catheterized (assuming the tray has been oriented as directed by the belly band 46). Further, the distal tip of the catheter 92 is positioned such that it essentially points at the region to be catheterized such that the health care provider may simply lift the catheter 92 and move it a short distance in the direction it is pointing to begin insertion of the catheter 92 into the patient. Once the catheter 92 is positioned in the syringe or catheter compartment 2, the user may dispense the lubricating jelly from the syringe 89 into the syringe or catheter compartment 2 onto a distal portion of the catheter 92 (e.g., the syringe may be dispensed on the left side of the syringe or catheter compartment near the patient and the region to be catheterized), and twist the catheter 92 in the lubricating jelly to ensure it is properly lubricated.

While the above lubrication method is beneficial for the reasons discussed above, other methods of lubricating the catheter 92 are also possible. In one embodiment, the health care provider may dispense the lubricating jelly onto a portion of the sterile/CSR wrap around the tray and put the end of the Catheter in the lubricating jelly to lubricate. In one embodiment, the user may dispense the lubricating jelly directly into the syringe or catheter compartment 2 before moving the catheter 92 from main compartment 1, and then move the distal portion of the catheter 92 into the lubricating jelly.

After lubricating the catheter 92, the health care provider may leave the catheter 92 temporarily in the syringe and catheter compartment 2 while he/she uses his/her non-dominant hand to retract the genitalia, and uses his/her dominant hand to prepare and sterilize the patient with the swabs or swabsticks saturated with sterilizing or iodine solution. The swabs or swabsticks (e.g., swabs or swabsticks 34 with absorbent head 36 and stick 38 discussed above) may be twisted either clockwise or counterclockwise to easily release them from the channels of the swab compartment as discussed above. Preferably each swab or swabstick will be used for one swipe on the patient only. For female patients, one may cleanse the patient by: (1) using a downward stroke with one swab or swab stick to cleanse the right labia minora and discard the swab or swabstick, (2) using a downward stroke with another swab or swabstick to cleanse the left labia minora and discard the swab or swabstick, and (3) using a third swab or swabstick to cleanse the middle area between the labia minora. For male patients, one may cleanse the patient with a swab or swabstick using a circular motion starting at the urethral meatus and working outward. After prepping and sterilizing the patient in this way, the health care provider uses his/her dominant hand to insert the catheter into the patient's bladder (urine becomes visible in the tubing when the catheter enters the bladder, but two additional inches beyond this point should be inserted to allow the retention balloon to enter the bladder), and inflate the retention balloon in the bladder by injecting the sterile liquid from the syringe of sterile liquid 88 into the catheter 92 through the inflation port. Indeed, these are the steps instructed on the tray in the fifth step, sixth step, and seventh step, which state, respectively, "(5) Retract Genitalia (Non-Dominant Hand)", "(6) Prep Patient with Swabs (Dominant Hand)", and "(7) Insert Catheter & Inflate Balloon (Dominant Hand)." Variations on these instructions/procedural indicators or other instructions/procedural indicators are possible. Once inflated, the health care provider may gently pull the catheter until the inflated balloon is snug against the bladder neck. These steps complete the catheterization stage or stage "B" of the procedure.

Figure 29:
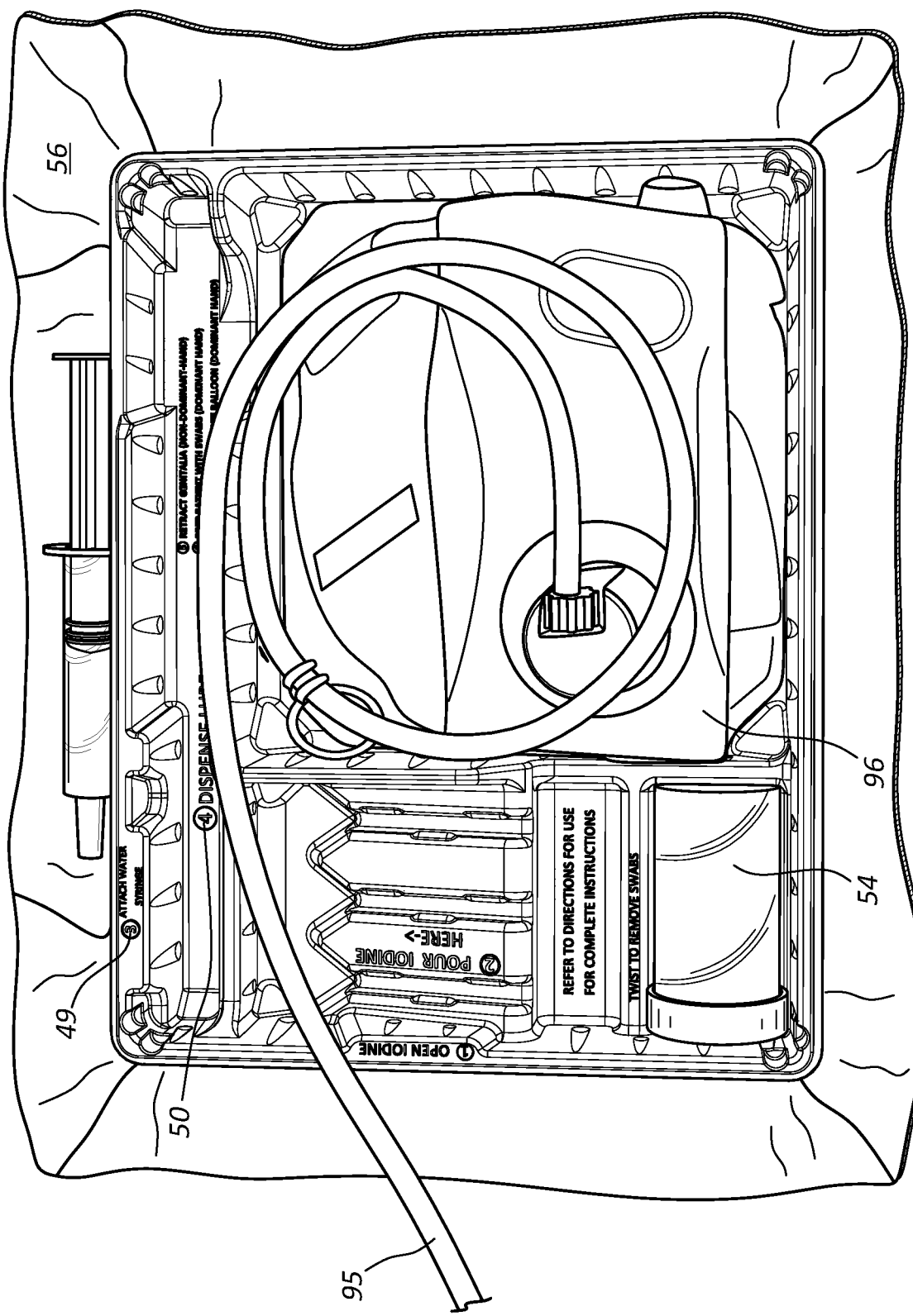
FIG. 29 shows a top view of the exemplary catheterization package of FIG. 29 after the catheter has been removed from the tray and inserted in a patient, with the drainage tubing extending in the direction of the patient.

FIG. 29 shows how the tray may look immediately after the catheter has been properly placed in the patient. Note that the drainage tubing 95 easily follows the catheter 92 toward the patient and out of the tray. A folded urine collection bag 96 is positioned in the main compartment 1 in FIG. 29 and may be packaged pre-connected to the tubing 95, catheter 92, and/or other components of the catheter assembly. Urine collection bag 96 may be unfolded and hung below the patient to collect urine as it drains from the patient.

After catheterization of the patient (i.e., after the catheter has been inserted and the retention balloon inflated in the patient's bladder), additional steps may be taken. For example, in stage "C" or the Care and Maintenance stage, the health care provider may: (1) secure the Foley catheter to the patient (e.g., using a StatLock® device), (2) position the urine bag and/or urine meter below the patient's bladder (e.g., hang the bag on a hanger on the bed rail at the foot of the bed) and secure the tubing to the bed sheets (e.g., with a clip) in such a way that the tubing is not kinked, (3) document the insertion date by indicating time and date of catheter insertion on a label and/or chart (e.g., the label/sheet 72 shown in FIG. 16) and document the procedure according to hospital protocol, (4) maintain the catheter (e.g., if it has a sterile red seal, then maintain the red seal), (5) re-assess the need for the indwelling catheter routinely evaluate whether the catheter becomes unnecessary, (6) and/or other care or maintenance steps.

Stage "C" and associated instructions/procedural indicators are identified in the main compartment of the catheterization tray as shown in FIGS. 1, 2, and 5. For example, the stage "C" instructions/procedural indicators may include: "(1) Secure Foley with StatLock®", "(2) position bag below bladder", "secure tubing to sheets with clip", "(3) document insertion date", "(4) maintain red seal per hospital policy", "(5) assess need for catheter routinely." Variations on these instructions/procedural indicators or other instructions/procedural indicators are possible. Urine samples may be taken as instructed in FIG. 14D. Ultimately, the catheter may be removed as instructed in FIG. 14C.

The catheterization package(s) and catheterization tray(s) described herein made be manufactured/packaged in different ways. For example, a manufacturer or vendor of catheterization packages may vary the steps or procedures described herein, may reorder the steps, may perform additional steps beyond those described, and/or may omit certain steps as circumstances and unique needs may require. Further, any features, components, arrangements, designs, ordering of components, etc. described above (e.g., features or arrangements that make using the catheterization package more intuitive or logical) may be added to or included in the catheterization package during manufacturing, e.g., in a method of manufacturing/packaging. However, exemplary, non-limiting, methods of manufacture/packaging are described below. The steps described herein may be done in order as described or out of order.

In one embodiment, a catheterization package is manufactured/packaged by providing a catheterization tray (e.g., a catheterization tray similar to or including features of those shown in FIGS. 1-5 and described above). The tray may be purchased or formed by the manufacturer of the catheterization package. If manufactured, the tray may be formed using an injection molding process or other suitable processes. Instructions/procedural indicators may be integrated on, printed, or otherwise included on the tray as described above and as shown, for example, in FIGS. 1, 2, and 5.

Various components (e.g., any of the components discussed above or elsewhere herein) may be added to the tray. In one embodiment, a pre-connected drainage system may be added to/included in the tray, e.g., in the main compartment 1 as shown in FIG. 26. The drainage system may include a drainage/collection bag 96, drainage tubing 95, a catheter 92 (e.g., a Foley catheter), a drainage outlet, a urine meter, or other drainage components. Swabs or swabsticks 34 may be added to/included in the tray, e.g., in the swab compartment 3 as shown in FIG. 8 or FIG. 26. A specimen or sample container 54 and a label that can be filled out with details regarding the sample and adhered to the specimen or sample container may be added to/included in the tray, e.g., in the corner storage compartment 5 a shown in FIG. 26. A packet or container of a sterilizing skin cleanser 52 (e.g., a packet or container of povidone-iodine solution) may be added to/included in the tray, e.g., in the swab compartment 3 on top of the swabsticks 34 as shown in FIG. 25. A packet or container of lubricant 89 (e.g., a syringe of lubricating jelly) may be added to/included in the tray, e.g., in the syringe or catheter compartment 2 as shown in FIG. 26. A syringe of sterile liquid 88 (e.g., a 10 cc syringe of sterile water for inflating the retention balloon of the Foley catheter) may be added to/included in the tray, e.g., in the syringe or catheter compartment 2 on top of or partially on top of the syringe of lubricating jelly 89 as shown in FIG. 26. A fenestrated drape to place on patient may be added to/included in the tray, e.g., on top of other components, and may span portions of more than one compartment as shown in FIG. 24. An underpad to place under the buttocks of a patient (e.g., a waterproof absorbent underpad) may be added to/included in the tray, e.g., on top of the fenestrated drape or other components, and may span portions of more than one compartment. Both the underpad and fenestrated drape are represented in the figures by pad/drape 86. Gloves (e.g., a package 58 of rubber gloves, latex gloves, latex-free gloves) may be added to/included in the tray, e.g., on top of the underpad or other components and may span portions of more than one compartment as shown in FIG. 22.

Figure 13:
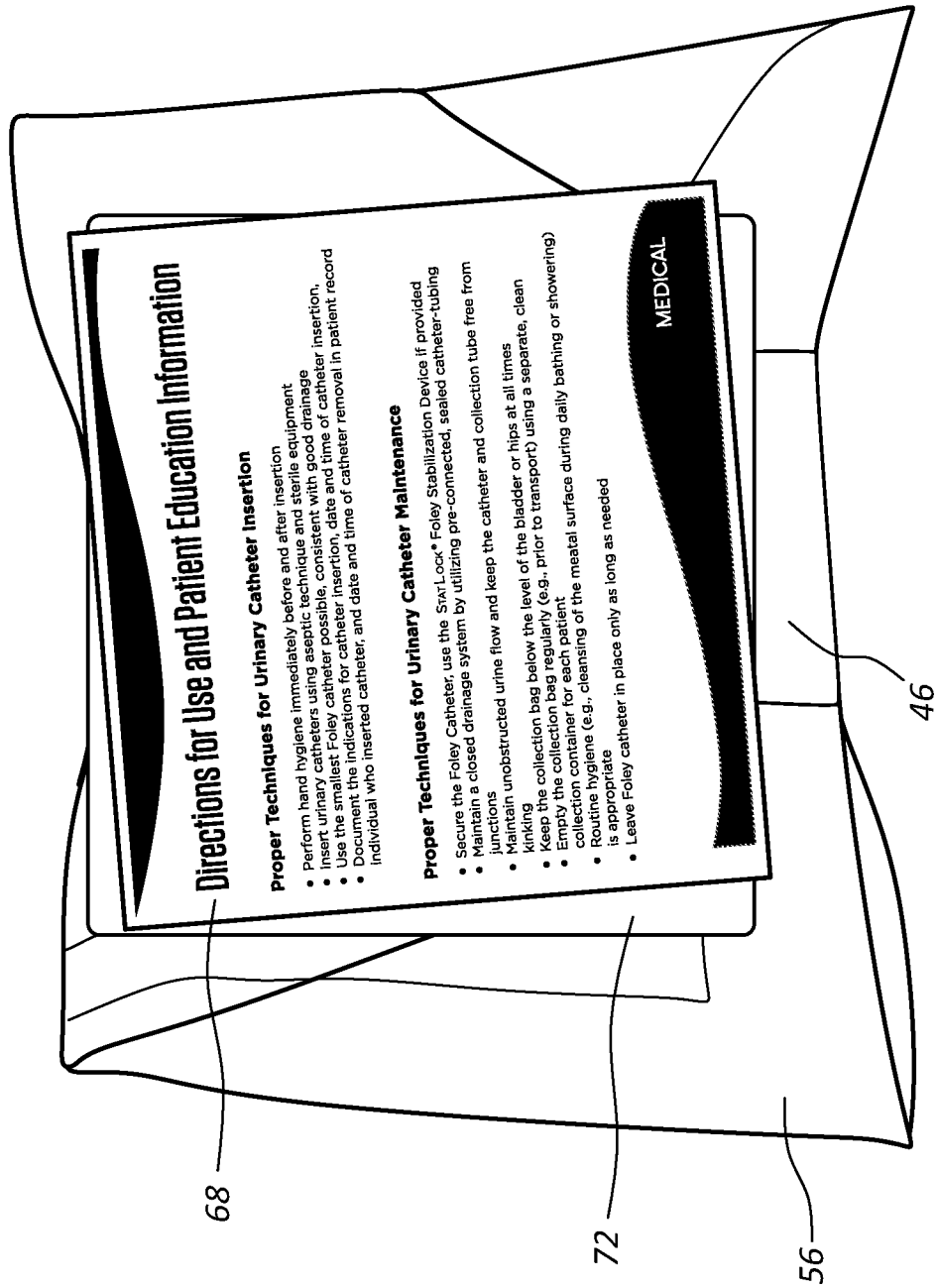
FIG. 13 shows a top view of an exemplary catheterization package (e.g., either the exemplary catheterization package of FIG. 9 or FIG. 10) after the sealed bag and packaging label have been removed, and showing an exemplary detailed instructions/procedural indicators document or directions for use (DFU) document thereon.
Figure 14B:
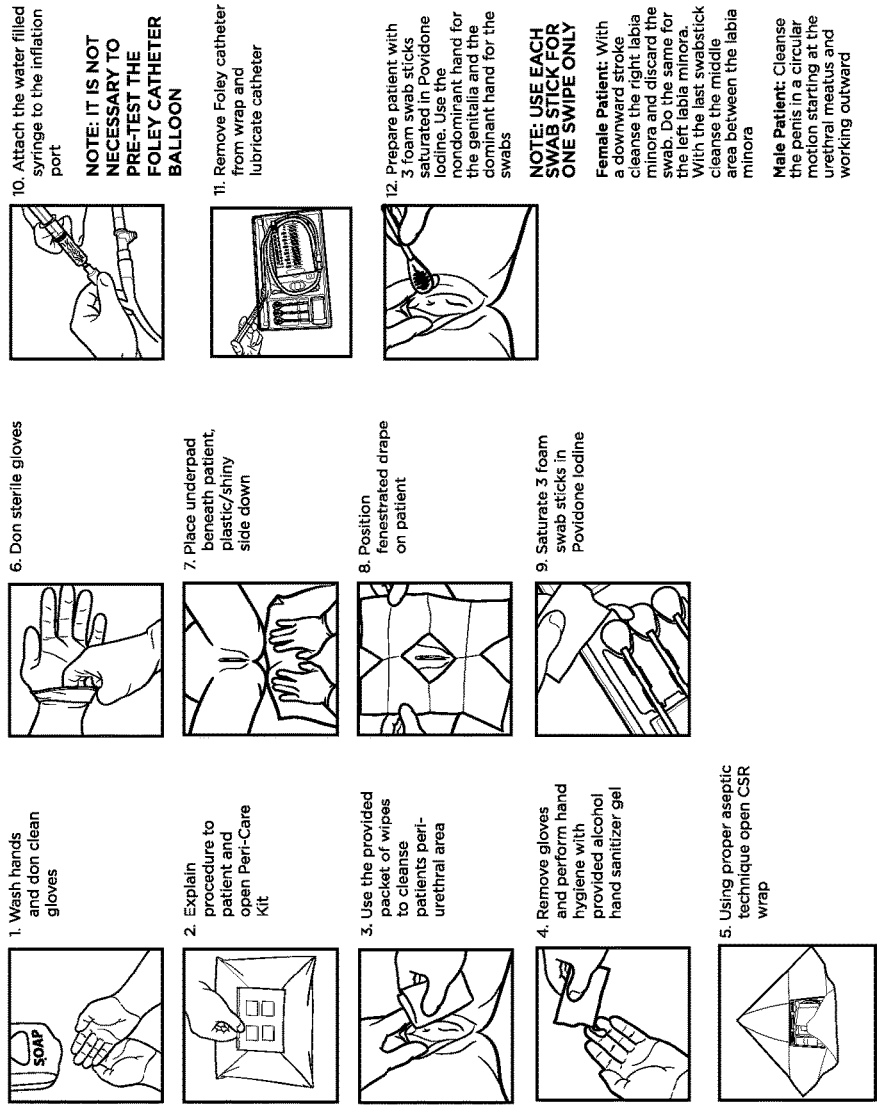
FIG. 14B shows another page of the exemplary document of detailed catheterization instructions/procedural indicators or directions for use (DFU) document of FIG. 14A.
Figure 14C:
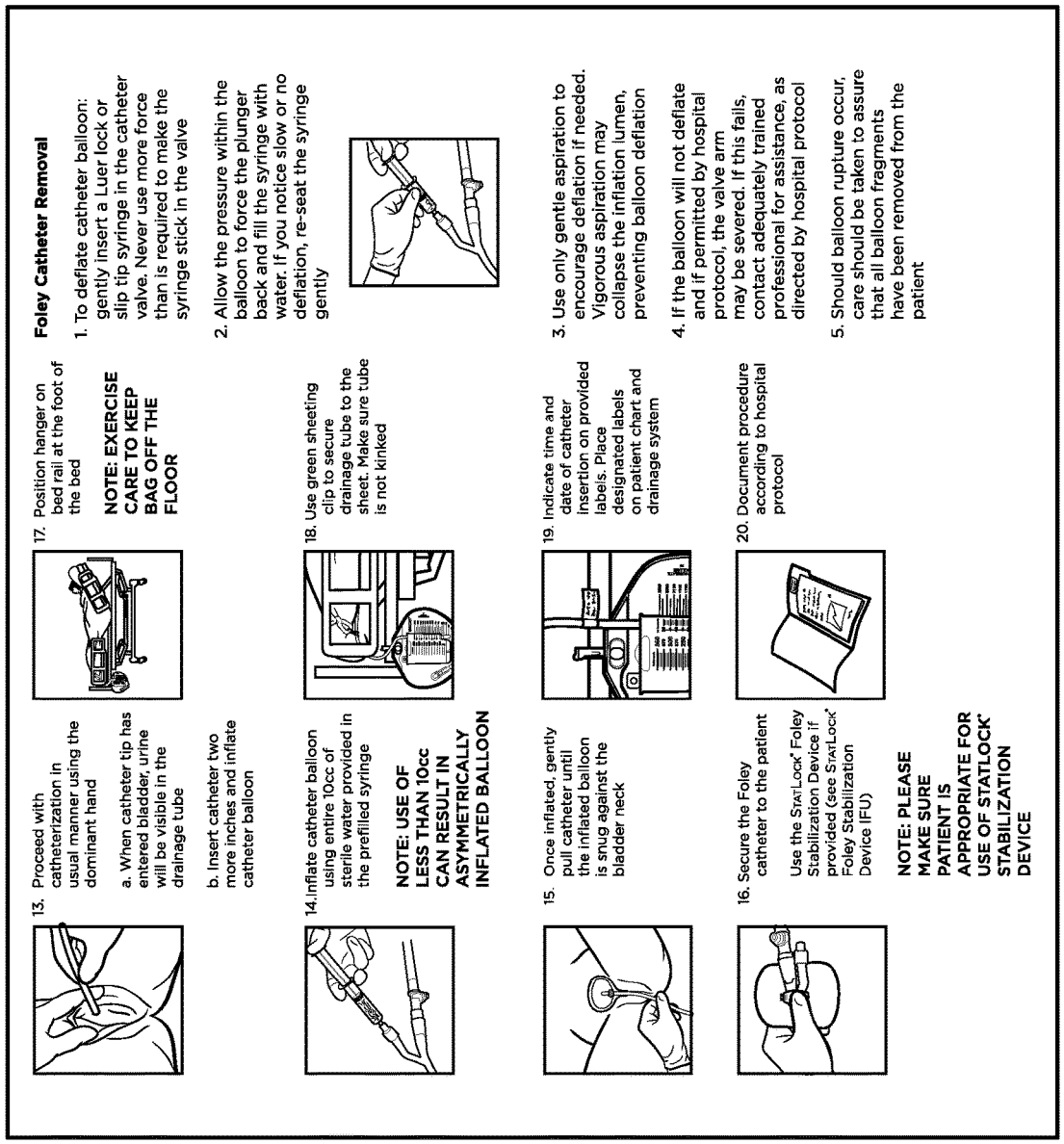
FIG. 14C shows another page of the exemplary document of detailed catheterization instructions/procedural indicators or directions for use (DFU) document of FIG. 14A.

The tray and components may be sterilized, and a sterile wrap 56 (e.g., a CSR wrap) may be folded or wrapped around the catheterization tray as shown in FIGS. 20-21. A belly band 46 (e.g., to hold the sterile wrap in a folded configuration and help to keep all the contents inside the tray, so the items do not move around) may be included around the sterile wrap 56 as shown in FIG. 20. A perineal care (or peri-care) packet or kit 74 (e.g., as shown in FIGS. 17-19) may be added to/included in the catheterization package, e.g., placed over the belly band 46 and/or sterile wrap 56 as shown in FIGS. 17 and 18. The perineal care packet or kit 74 may include hand sanitizer 76 (e.g., antiseptic gel hand rinse), moist towelettes 78 (e.g., a package of castile soap towelettes), instructions 80 (e.g., instruction for health care provider and/or instructions for patient), and/or other components (see e.g., FIG. 19). An insert sheet or label 72 with instructions or other information may be added to/included in the catheterization package, e.g., an insert sheet or label 72 with a checklist of safety considerations/steps and/or a patient information chart may be included on top of the perineal care packet or kit as shown in FIG. 16. A detailed instructions document (e.g., as shown in FIGS. 14A-14D) and/or patient educational information (e.g., as shown in FIGS. 15A and 15B) may be added to/included in the catheterization package, e.g., a directions for use (DFU) document 68 and/or a patient educational pamphlet 70 may be included on top of the insert sheet as shown in FIG. 13. A packaging label 62 (e.g., a packaging label as described above and shown in FIGS. 9-12) may be added to/included in the catheterization package, e.g., on top of all the other components and with edges folding down to cover the sides of the catheterization tray. The catheterization package may be sterilized and sealed, e.g., in sealed container or bag 60 as shown in FIGS. 9 and 10. Other components useful to catheterization or care may also be included.

In one embodiment, a catheterization system may include a ureteral catheter assembly and/or materials or supplies (e.g., catheterization elements or components, such as sanitizer liquid, lubricant, inflation liquid, gloves, etc.) suitable or necessary for a ureteral catheterization procedure. For instance, the catheterization system may include a catheterization tray that has multiple compartments for housing and/or securing a ureteral catheter assembly (e.g., an assembly including a Foley catheter) as well as other sterile and/or non-sterile catheterization elements, including any of those discussed above. Sterile catheterization elements may be housed in the catheterization tray in a manner that the sterile elements remain uncontaminated by non-sterile catheterization elements.

The catheterization tray may include one or more visual, procedural indicators or instructions that may aid a user during the catheterization procedure. For instance, the procedural indicators may aid the user in orienting the catheterization tray (and catheterization components or elements thereof) relative to a patient, such that the catheterization components and/or elements may be positioned at predictable and suitable or desirable locations and/or orientations relative to the user and/or to the patient. Additionally or alternatively, the procedural indicators may aid the user in sequencing use of the catheterization components and/or removal thereof from the catheterization tray.

As mentioned above, the catheterization tray and system including such tray may facilitate aseptic techniques during a catheterization procedure. In one embodiment, as shown in FIG. 30A, catheterization system 100 includes container 110 (e.g., a sealed bag), which may hermetically seal or contain the catheterization tray and catheterization components. For instance, the container 110 may facilitate maintaining sterility of sterile catheterization components. For example, the container 110 may be a plastic bag (e.g., a polyethylene bag). Moreover, the container 110 may include a peelable side 111, which may be detached from a non-peelable side 112 to form an opening in the container 110 (container 60 above may have similar features and properties); the contents located in the container 110 may be removed through the opening.

In one embodiment, the catheterization tray and at least some of the contents thereof (i.e., catheterization components) may be at least partially surrounded or enveloped by an identification cover 120. In one embodiment, the packaging label or identification cover 120 (e.g., similar to packaging label 62 discussed above) may include one or more visual identifiers including key information or variables, such as visual identifiers 121, 122, 123 (e.g., these can be similar to the information squares discussed above), which may provide indication related to the type and/or contents of the catheterization system 100.

For example, the packaging label or identification cover 120 may be fabricated from a sheet-like material, such as paper, cardboard, plastic (e.g., plastic film), etc. The visual identifiers 121, 122, 123 may be configured to convey sufficient information for the user to identify the specific type of the catheterization system 100 and/or contents thereof. For instance, the visual identifier 121 may identify the size of the catheter (e.g., 16 French, etc.). In one example, the visual identifier 122 may indicate that the catheterization system 100 includes a urine meter (which may be attached to the catheter), and/or the visual identifier 123 may indicate that the catheterization system 100 includes a catheter stabilization device (e.g., STATLOCK).

The visual identifiers 121, 122, 123 may be visually separated or isolated one from another. For example, the visual identifiers 121, 122, 123 may include a generally square or rectangular perimeter outline that may delimit or define the outer contours thereof. In other words, the identifying information of the visual identifiers 121, 122, 123 may be contained within the generally rectangular outlines of the visual identifiers 121, 122, 123. Hence, for instance, the user may easily and/or quickly locate the pertinent information of the identification cover 120, to identify and/or select the particular catheterization system 100 suitable for the procedure.

One, some, or all of the visual identifiers 121, 122, 123 may include any visible indications or information that may inform the user about specifics of the catheterization system 100. For example, the visual identifiers 121, 122, 123 may include text, images, symbols, etc. Moreover, the visual identifiers 121, 122, 123 and/or portions thereof may have any suitable color or multiple colors, which may aid the user in identifying and/or distinguishing among the visual identifiers 121, 122, 123. In one embodiment, at least one of the visual identifiers 121, 122, 123 may have a different color than others.

It should be appreciated that the particular contour shape, size, thickness, or combinations thereof, which surrounds or contains the identifying information of the visual identifiers 121, 122, 123 may vary from one embodiment to the next. As such, the visual identifiers 121, 122, 123 may have generally circular, triangular, or polygonal shapes. Furthermore, the identification cover 120 may include any number of suitable materials that may carry the visual identifiers 121, 122, 123 may vary from one embodiment to another. For instance, the visual identifiers 121, 122, 123 may be printed, embossed, or otherwise transferred onto the identification cover 120.

The identification cover 120 may include any number of visual identifiers. In other words, the visual identifiers 121, 122, 123 may be located at any number of suitable locations on the identification cover 120 and/or may be duplicated. For example, the identification cover 120 may include visual identifiers 121, 122, 123 on a major face thereof and on a minor face thereof. In one embodiment, the visual identifiers 121, 122, 123 may be located on one, some, or all visible sides of the catheterization system 100 (e.g., one, some, or all of the visual identifiers 121, 122, 123 may be visible from any side of the catheterization system 100 during storage thereof).

The identification cover 120 may be removable from the catheterization tray. For instance, the identification cover 120 may be generally detached from the catheterization tray (e.g., the identification cover 120 may lie on the catheterization tray and may be secured relative to the catheterization tray by the container 110). Furthermore, as shown in FIG. 30B, removing the identification cover may expose the catheterization tray, which may be wrapped by or into a central supply room (CSR) sterile wrap 130. Accordingly, the CSR sterile wrap 130 may at least temporarily secure components in the catheterization tray.

The CSR sterile wrap 130 may be unwrapped and removed from the catheterization tray and may be used during the catheterization procedure. For example, the CSR sterile wrap 130 may be placed near and/or under the patient to provide at least a partially sterile environment near the site of the catheterization procedure, thereby reducing risk of infections associated with the catheterization procedure. The CSR sterile wrap 130 may be substantially opaque, such that the contents of the catheterization tray and/or locations catheterization components are obscured or not be visible to the user. Optionally, the CSR sterile wrap 130 may be translucent or transparent, such that the user may view and/or visually identify catheterization components contained in the catheterization tray.

The catheterization system 100 may include a belly band or directional indicator wrapper 140, which may provide an indication of relative positioning and/or orientation of the components in the catheterization tray, which may not be visible to the user. For example, the belly band or indicator wrapper 140 may include a direction arrow 141 that may be aligned by the user to point toward the catheter insertion site, which may orient the catheterization tray and catheterization components therein relative to the patient. For instance, orienting the catheterization tray in a manner that aligns the direction arrow 141 in the direction of the insertion site may position the catheterization components and/or elements at least partially sequentially, such that the catheterization elements and/or components to be used earlier in the procedure are located closer to the patient than the catheterization components intended to be used later in the procedure.

In addition, the belly band or indicator wrapper 140 may include a warning indicator 142 to alert the user to proper aseptic technique for the catheterization procedure. For example, the warning indicator 142 may include one or more specific elements identifying the particular steps suitable or necessary for proper aseptic procedure. In one embodiment, the warning indicator 142 identifies one or more of the following steps: (1) open CSR sterile wrap 130; (2) don sterile gloves; (3) place underpad; (4) place fenestrated drape; or (5) follow steps identified by procedure indicators located inside the catheterization tray.

While the indicator wrapper 140 may wrap around the CSR sterile wrap 130, this disclosure is not so limited. For example, a sticker or an adhesive label may be attached to the CSR sterile wrap and may include the same or similar indicators as the indicator wrapper 140. Alternatively or additionally, the indicators may be placed directly onto the CSR sterile wrap 130 (e.g., may be printed, embossed, or otherwise transferred thereto).

After the CSR sterile wrap 130 is removed or unwrapped from the catheterization tray, the contents of the catheterization tray may be exposed. FIG. 31A illustrates a catheterization tray 200 of the catheterization system 100. The catheterization tray 200 may include multiple compartments that may secure or house various catheterization components. The shape and size of the catheterization tray 200 may be defined by peripheral walls thereof. For instance, peripheral walls 201, 202, 203, and 204 may define an approximately rectangular outer shell or exterior perimeter of the catheterization tray 200.

The catheterization tray 200 may be molded (e.g., injection molded, thermoformed) or stamped (e.g., from a plastic material). Hence, the outer or peripheral walls 201, 202, 203, and 204 may be formed from a sheet-like material. One or more of the outer or peripheral walls 201, 202, 203, or 204 may include stiffening ribs 205, which may provide rigidity and/or stiffness to the peripheral walls 201, 202, 203, 204. The stiffening ribs 205 may have an approximately tapered shape and/or may protrude outward from the respective peripheral walls 201, 202, 203, or 204. More specifically, for example, lower portions of the stiffening ribs 205 (portions closer to the bottom/floor of the catheterization tray 200) may protrude out of the respective peripheral walls 201, 202, 203, or 204 more than the upper portions of the stiffening ribs 205 (portions closer to the opening of the catheterization tray 200). At least a portion of one, some, or all of the stiffening ribs 205 may have a partially conical shape.

The catheterization tray 200 may include a swab compartment 210, which may include one or more swabs 150 therein. Additionally or alternatively, the compartment 210 may include a cleansing/sterilizing solution or sanitizer packet 160, which may contain one or more sanitizing agents or cleansing/sterilizing solutions (e.g., containing povidone-iodine solution). The compartment 210 may be positioned near and at least partially defined by the peripheral wall 201 of the catheterization tray 200. In some instances, the exterior of the sanitizer packet 160 may be non-sterile. Hence, the cleansing/sterilizing solution or sanitizer packet 160 may be placed inside another packaging or a bag, which may have a sterile exterior that may prevent or reduce contamination of other catheterization components in the catheterization tray 200 from the unsterilized packet 160 of cleansing solution or sanitizer. The plastic bag may include a zipper or similar mechanism that may be operated by the user to open and access the packet 160 and/or other components therein.

Catheterization instructions may include images and description of various steps or acts taken during the catheterization procedure. In some instances, instructions also may identify specific step or act numbers, thereby suggesting a particular sequence of steps or acts for the catheterization procedure. Catheterization instructions, which may be non-sterile, may be placed into a sterile container, such as a plastic bag, thereby isolating or separating the non-sterile instructions from sterile catheterization components in the catheterization tray 200. Also, in some examples, the catheterization system may include multiple sets of catheterization instructions, which may improve compliance with aseptic catheterization procedures. For example, catheterization instructions may could be attached or adhered to (e.g., as a sticker) inside the sterile plastic bag and/or to another catheterization element or component (e.g., to the sterile container with the sanitizer packet 160), to an exterior sleeve or portion of the catheterization system, etc.

The compartment 210 may be configured to contained sanitizing substance (e.g., liquid), which may be dispensed in the compartment 210 from the sanitizer packet 160. For example, as described below in more detail, the compartment 210 may have a slanted bottom/floor, such that the cleansing or sterilizing solution (e.g., povidone-iodine solution) or sanitizer from the packet 160 may pool near and/or at a lowermost corner between a bottom/floor and a sidewall and/or separator/divider wall (e.g., internal separator/divider wall 211) of the compartment 210. Furthermore, tips of the swabs 150 may be located at or near the lowermost corner between the bottom/floor and the sidewall of the compartment 210, such that the tips of the swabs 150 are positioned in the dispensed sterilizing or sanitizing liquid.

The compartment 210 may be at least partially defined by a portion of the peripheral wall 201, the internal separator/divider wall 211, by an internal separator/divider wall 212, and by the slanted bottom/floor. For instance, the lowermost portion of the compartment 210 may be located at the corner edge formed by and between the internal separator wall 211 and the slanted bottom/floor. Hence, positioning the tips/absorbent heads of the swabs 150 near the slanted bottom/floor and/or near the internal separator wall 211 of the compartment 210 may locate the tips/absorbent heads of the swabs 150 at or near the lowermost portion of the compartment 210.

As described above, the catheterization tray 200 may be oriented relative to the patient in a manner that places the peripheral wall 201 and the compartment 210 closer to the insertion site than the opposing peripheral wall 203 of the catheterization tray 200. In other words, orienting the catheterization tray 200 based on the direction arrow of the directional indicator wrapper (while the contents and compartments of the catheterization tray 200 are concealed or covered by the CSR sterile wrap 130 (FIG. 30B) may place the peripheral wall 201 and the compartment 210 near the insertion site. In some instances, the insertion site may be first sterilized with the swabs 150 that may be saturated with the sanitizing liquid from the sanitizer packet 160. As such, positioning the compartment 210 together with the swabs 150 and sanitizer packet 160 near the insertion site may reduce spillage of the sanitizer liquid (e.g., onto one or more catheterization components in the catheterization tray 200) and/or contamination of the swabs 150, which may lead to contamination of the insertion site.

As described below in more detail, the compartment 210 may have a slanted bottom/floor. For instance, an upper edge (or surface), such as an upper edge 206 of the catheterization tray 200 may lie in an imaginary plane that may be approximately parallel to a support surface that may support the catheterization tray 200 (e.g., surface of the patient's bed). The slanted bottom/floor of the compartment 210 may have a non-parallel orientation relative to the imaginary plane of the upper edge 206 and/or to the support surface.

Furthermore, the bottom/floor of the compartment 210 may be non-parallel relative to bottoms/floors of one or more other compartments in the catheterization tray 200. For example, the catheterization tray 200 may be set on the support surface, such that bottoms/floors of one or more compartments support and/or orient the catheterization tray 200 on the support surface. Hence, as described above, the bottom/floor of the compartment 210 may have a non-parallel orientation relative to the support surface.

The catheterization tray 200 may include a side compartment 220. For example, the compartment 220 may extend along substantially an entire side or length of the catheterization tray 200 (e.g., the compartment 220 may extend between the peripheral walls 201 and 203 and/or may be partially defined thereby). Hence, in some instances, one side of the compartment 220 may be defined by a peripheral wall, such as by the 204.

The compartment 220 may contain any number of suitable elements or components of the catheterization kit. For example, the compartment 220 may contain a syringe 170 with liquid that may be used for inflating a balloon of the catheter (described below) and/or a syringe 180 that may contain lubricant. As such, the width of the compartment 220 may be sufficient to accommodate the syringes 170, 180. In some instances, the syringes 170, 180 may be oriented lengthwise along the compartment 220, and may lie in a single row, one in front of the other therein.

The catheterization tray 200 may include one or more cutouts or recesses in a separator wall 221, which may separate the compartment 220 from an adjacent compartment(s) (e.g., from a catheter compartment 230). For example, one or more recesses in the internal separator wall 221 may have top edges thereof located below the upper edge 206 of the catheterization tray 200. More specifically, in some instances, the recesses may provide access to one or more of the syringes 170, 180 from the compartment 230. Hence, a user of the catheterization kit may remove the syringe 170 and/or syringe 180 by reaching into the compartment 230, in lieu of or in addition to reaching into the compartment 220.

In one embodiment, the syringes 170 and 180 may be differently sized. Hence, in one embodiment, at least a portion of the compartment 220 may be narrower than another portion thereof, to accommodate syringes 170, 180 of different sizes. For example, compartment 210 may include a narrowing protrusion 222, which may extend into the space of the compartment 220, thereby narrowing a portion of the compartment 220. For instance, the syringe 170 may have a smaller diameter or peripheral size than the syringe 180. Hence, the narrowing protrusion 222 may narrow the width of the (s) of the compartment 220 may be sufficiently wide to accommodate the syringe 180 (e.g., the narrowing protrusion 222 may prevent or limit lateral movement of the syringe 170 in the compartment 220).

As mentioned above, the catheterization tray 200 may include the main or catheter compartment 230. The compartment 230 may have an approximately rectangular shape. For example, the compartment 230 and the shape thereof may be at least partially defined by the peripheral wall 203, at least a portion of the peripheral wall 202, and by separator/divider walls 212, 221. While in one embodiment the compartment 230 may have a generally rectangular shape, it should be appreciated that the shape of the compartment 230 may vary from one embodiment to the next.

In any event, the compartment 230 may be sized (e.g., perimeter dimensions and depth), shaped, or otherwise configured to contain or house a catheter assembly 190. For instance, the catheter assembly 190 may include a catheter 191 that may be connected to a urine collection bag and/or urine meter 192. In some instances, the compartment 230 also may contain or house a STATLOCK 193, which may secure at least a portion of the catheter assembly 190 during the catheterization procedure.

The compartment 230 may have an approximately flat or planar bottom/floor, as described below in more detail. For example, the bottom/floor of the compartment 230 may support the catheterization tray 200 on the support surface. Hence, in one embodiment, the bottom/floor of the compartment 210 may have a non-parallel orientation relative to the bottom/floor of the compartment 230.

As mentioned above, the compartment 230 may have an approximately rectangular shape. Furthermore, the compartment 230 may have rounded or chamfered interior corners 231 between the walls that define the perimeter of the compartment 230. Additionally or alternatively, the upper portions of the walls (e.g., peripheral walls and/or separator walls) may have one or more chamfers or fillets 232, which may extend at least partially along the respective lengths of such walls.

The catheterization tray 200 also may include an auxiliary compartment 240 that may contain or house an auxiliary container 195 (e.g., a specimen or sample container). For instance, the auxiliary container 195 may be approximately cylindrical and may include a cap. Furthermore, the compartment 240 may be shaped, sized, and configured to secure the auxiliary container 195 therein. In one embodiment, the length of the compartment 240 may be similar to the length of the auxiliary container 195 (e.g., the compartment 240 may include a small clearance or may have an interference fit with the auxiliary container 195). In one embodiment, the bottom/floor of the compartment 240 may be semi-cylindrical or generally arcuate and may approximately follow the general cylindrical shape of the auxiliary container 195. Hence, for instance, the bottom/floor of the compartment 240 may at least partially wrap around the auxiliary container 195.

Figure 31B:
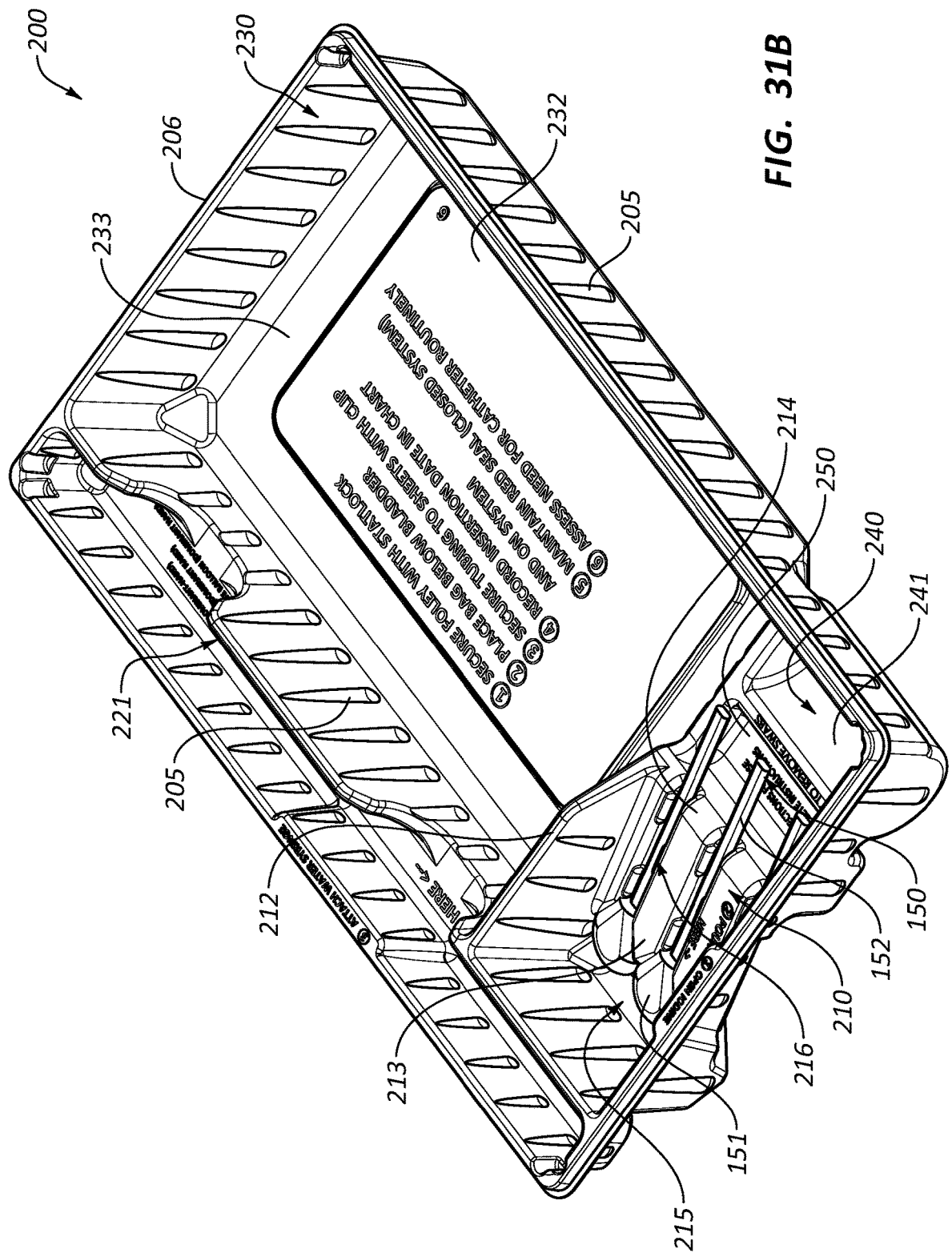
FIG. 31B is an isometric view of the exemplary catheterization tray of FIG. 31A with some of the contents thereof removed therefrom.

For example, as shown in FIG. 31B, the compartment 240 may have a partially rounded bottom/floor 241. The compartment 240 may be separated from the compartment 210 in the catheterization tray 200. For instance, the catheterization tray 200 may include an overflow cavity 250 located between the compartment 240 and the compartment 210. In one embodiment, the overflow cavity 250 may form a recess or depression between the compartment 210 and the compartment 240. For example, the overflow cavity 250 may prevent or limit overflow of the sanitizing liquid dispensed into the compartment 210. Moreover, the user may tap excess sanitizing liquid from the tips of the swabs 150 into the overflow cavity 250, before applying the sanitizing liquid at or near the insertion site.

The slanted bottom/floor 213 of the compartment 210 may be elevated or stepped above the overflow cavity 250. For example, the slanted bottom/floor 213 may terminate at a fillet or radius 214 that may extend from the slanted bottom/floor 213 downward toward the overflow cavity 250 or an edge thereof. The radius 214 may provide a transition between the slanted bottom/floor 213 and at least a portion of the overflow cavity 250 located below the slanted bottom/floor 213. In any event, the slanted bottom/floor 213 may slant downward and away from the overflow cavity 250.

As mentioned above, sanitizing liquid may be dispensed at the lowermost portion 215 of the compartment 210 (e.g., at or near the lowermost portion of the slanted bottom/floor 213). Furthermore, sanitizing liquid dispensed in the compartment 210 may generally flow toward and pool at the lowermost portion 215 of the compartment 210. In addition, the tips 151 of the swabs 150 may be set or positioned in the sanitizing liquid. As such, the user may remove the swabs 150 from the compartment 210 and apply sanitizing liquid at the insertion site without further acts.

The swabs 150 may be secured in the compartment 210 in a manner that positions the tip(s) or absorbent head(s) 151 in the sanitizing liquid dispense in the compartment 210. For example, one, some, or each of the swabs 150 may include an elongated stem/stick 152 and a tip/absorbent head 151 attached to the stem/stick 152. Moreover, the compartment 210 may include channels 216 that may house and secure the elongated stem/stick 152 of the swabs 150. Hence, the stems/sticks 152 of the swabs 150 may be secured in the channels 216 of the compartment 210.

The channels 216 may include one or more retention features (e.g., detents, overhangs), which may secure the stems/sticks 152 therein. For example, the stems 152 may have approximately rectangular or generally rectangular cross-sectional shapes. When the stems/sticks 152 are oriented along the longer side of the rectangular cross-sectional shapes thereof, the retention features may secure the elongated stem 152 in the channels 216. Also, rotating or twisting the swabs 150 in the channels 216 (e.g., such that the shorter side of the rectangular cross-sectional shapes of the stems 152 may be oriented to lie within the channels 216) may disengage the stems 152 from the channels 216.

In other words, spacing between the retention features of the channels 216 may be less than the width of the longer side of the rectangular cross-sectional shape of the elongated stem 152, such that the retention features may restrain the elongated stem/stick 152 in the channels 216. Moreover, the spacing between the retention features may be greater than the length of the shorter side of the rectangular cross-sectional shape of the elongated stem/stick 152. Accordingly, twisting or rotating the swabs 150 within the channels 216 may allow the elongated stem/stick 152 to pass between the retention features of the channels 216 in order to remove the elongated stem/stick 152 therefrom.

The catheterization tray 200 (as well as the catheterization trays shown in FIGS. 1-5) may be fabricated in any number of suitable ways and with any number of suitable manufacturing techniques. As mentioned above, the catheterization tray(s) may be injection molded, thermoformed, or otherwise mass-produced. For instance, the catheterization tray(s) may be fabricated from a sheet of plastic material that may be processed by compressing and heating the sheet into the suitable configuration, as described herein. As such, one or more of the walls of the catheterization tray(s) may comprise a relatively thin plastic material (e.g., 0.005 inch, 0.010 inch, 0.020 inch, 0.050 inch, 0.catheterization system 100 inch, etc.). As described above, the catheterization tray(s) may include stiffening ribs on one or more peripheral walls thereof, which may provide rigidity to such peripheral walls.

The catheterization tray(s) may include stiffening ribs as described herein on one or more separator/divider walls that divide the interior space of the catheterization tray(s) into the compartments described herein. Also, as described below in more detail, the separator/divider walls (e.g., the separator/divider wall 221) may include folded or dual layers of sheet material. The stiffening ribs may protrude away from the compartments (e.g., away from the compartment 210, compartment 220, compartment 230) and into the space between the layers of the sheet material.

As described above, in the compartments, the inside corners and/or edges formed between the bottom/floor and separator walls may include fillets or chamfers. For example, such fillets or chamfers may reduce stress at the inside corners or edges of the compartments. Accordingly, the fillets and/or chamfers formed at the inside corners and/or edges of the compartments may reduce or prevent breakage or failure of the sheet material that forms the catheterization tray 200.

The bottom/floor of the compartment 230 may be substantially flat. Additionally or alternatively, the bottom/floor of the compartment 230 may have a protruding landing 232 and a recessed portion 233. For example, the recessed portion 233 may be lower or farther away from the upper edge 206 of the catheterization tray 200 than the landing 232. Furthermore, the recessed portion 233 may at least partially or completely wrap around the landing 232. As such, for instance, the recessed portion 233 may accommodate at least a portion of the catheter, which may wrap around the landing 232.

Figure 31C:
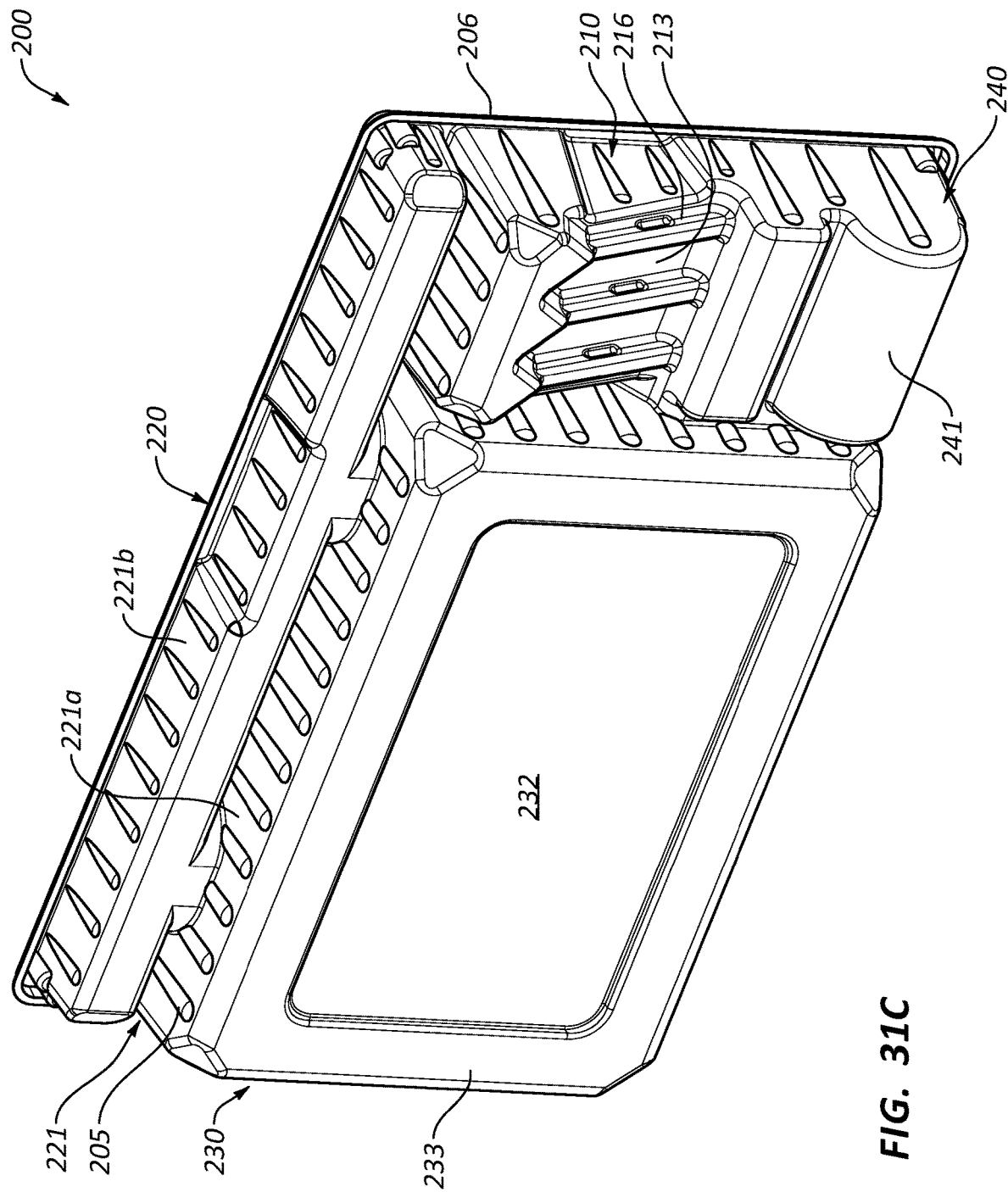

As described above, the catheterization tray 200 may be placed on a support surface, such as a surface of the patient's bed. For example, as shown in FIG. 31C the recessed portion 233 of the compartment 230 may form a protrusion on the exterior of the catheterization tray 200, while the landing 232 may form a recesses on the exterior of the catheterization tray 200. As such, the exterior surface of the recessed portion 233 may provide or form a surface that may orient and/or support the catheterization tray 200 on the support surface. Moreover, in one embodiment, the exterior surface of the recessed portion 233 may be approximately parallel to the imaginary plane of the upper edge 206.

Also, as mentioned above, the channels 216 of the compartment 210 may be generally parallel to the slanted bottom/floor 213 and slanted or non-parallel relative to the support surface. The channels 216 of the compartment 210 may have a non-parallel orientation relative to the exterior surface of the recessed portion 233. For instance, on the exterior of the catheterization tray 200, the channels 216 may protrude outward away from the slanted bottom/floor 213.

A compartment of the catheterization tray (e.g., compartment 210) or a portion thereof may carry the sanitizing or cleansing liquid (e.g., povidone-iodine solution) therein. For example, at least a portion of the compartment may carry the sanitizing liquid and may be sealed by a peelable cover. As such, during the catheterization procedure, the user may avoid pouring a sanitizing liquid out of a packet (e.g., into the catheterization tray), which may prevent or reduce spillage of the sanitizing liquid. The swabs may be at least partially submerged in the sanitizing liquid and/or at least partially sealed together therewith by the peelable cover. Alternatively or additionally, the swabs may be located in another compartment of the catheterization tray.

As described above, separator/divider walls of the catheterization tray 200 may be formed by two layers of a sheet material. At least some of the separator/divider walls may have space between the layers of the sheet material. For example, the separator wall 221 may include a first layer 221a and a second layer 221b spaced apart from each other (e.g., the first layer 221a may define or form the perimeter of the compartment 230, and the second layer 221b may define or form the perimeter of the compartment 220.

The stiffening ribs 205 on the first layer 221a of the separator wall 221 may protrude outward, away from the compartment 230 and into the space between the first and second layers 221a, 221b. The stiffening ribs 205 on the second layer 221b may also protrude outward, away from the compartment 220 and toward the outer perimeter or periphery of the catheterization tray 200. In any event, as described above, the compartments of the catheterization tray 200 may have indents that correspond to the protrusions formed on the exterior portions of the catheterization tray 200 by the stiffening ribs 205.

The catheterization tray 200 may include one or more instructions or procedural indicators that may assist a user during a catheterization procedure. For instance, as illustrated in FIG. 32, the catheterization tray 200 may include indicators 301-307, which may be printed on the catheterization tray 200. For example, a first indicator 301 may indicate to the user to open the package containing sanitizing liquid, and a second indicator 302 may indicate to the user to pour the sanitizing liquid into the compartment 210, during the catheterization procedure.

A third indicator 303 may indicate to the user to attach to the catheter the syringe containing liquid for inflating the catheter balloon. In one embodiment, a fourth indicator 304 may indicate to the user to dispense lubricant and/or may identify or suggest a location in the compartment 220 for dispensing lubricant. Also, indicators 305-307 may identify additional or alternative steps to take during the catheterization procedure (e.g., retract genitalia (with non-dominant hand), prepare patient with swabs (with dominant hand), insert catheter and inflate balloon (with dominant hand)).

The catheterization tray 200 may include an enlarged or bolded print of the indicators 301-307 for improved visibility. Further, other enlarged instructions/indicators may be printed on the bottom/floor of the compartment 230, as shown in FIG. 32. The presence of the indicators 301-307 on the catheterization tray 200 may obviate or reduce the necessity for printed handouts or similar instructions.

In one embodiment, as shown in FIG. 33, a catheterization system 100a may include one or more procedural indicators 260a on a CSR sterile wrap 130a. Except as otherwise described herein, the catheterization system 100a and its elements and components may be similar to or the same as catheterization system 100 (FIGS. 30A-32) and its respective elements and components. For example the catheterization system 100a may include the catheterization tray 200 and catheterization elements and/or components described above in connection with the catheterization tray 200 above.

In one embodiment, the CSR sterile wrap 130a may include one or more procedural indicators 260a that may assist a user during the catheterization procedure. For example, one or more of the procedural indicators 260a may be individually isolated and/or delimited, or otherwise visually enclosed by a perimeter outline. In particular, isolating each of the procedural indicators 260a may draw or focus user's attention thereto and may facilitate identification thereof. The procedural indicators 260a may contain similar or the same information as indicators 301-307 (FIG. 32).

In one embodiment, the catheterization tray may include a fenestrated drape, which may partially cover the patient and may facilitate insertion of the catheter. FIG. 34 illustrates a fenestrated drape 270. The fenestrated drape 270 may have a generally rectangular shape. Moreover, the fenestrated drape 270 may include perforations 271. In particular, the perforations 271 may generally form a shape of a cutout in the fenestrated drape 270, which may be formed therein by tearing a portion of the fenestrated drape 270 delimited by the perforations 271. In one embodiment, the central portion of the fenestrated drape 270 is already opened, i.e., the central material inside the area circumscribed by perforations 271 is removed prior to packaging the fenestrated drape 270.

The shape defined by the perforations 271 or the shape of the central opening may be suitable for accessing the genitalia of the patient for performing the catheterization procedure after covering the patient with the fenestrated drape 270. Also, in some instances, the fenestrated drape 270 may include side cutouts 272. For instance, the side cutouts 272 may be generally V-shaped. In one embodiment, the side cutouts 272 may facilitate placement of the fenestrated drape 270 about the legs of the patient.

As mentioned above, the catheterization system may include various components that may facilitate the catheterization procedure, such as swabs that may facilitate sanitizing area near or at the site of the catheterization. FIG. 35 illustrates an exemplary swab 150. For example, the swabs 150 may include the elongated member or stem/stick 152 and the tip/absorbent head 151 attached thereto.

The tip/absorbent head 151 may have a generally rounded outward or distal portion and a tapered proximal portion (e.g., tapering toward the proximal end of the tip/absorbent head 151 and toward the elongated stem/stick 152). For example, the tip/absorbent head 151 may be narrower at the proximal end of than at the distal portion (i.e., the distal portion may be generally flared and front edge thereof may be generally rounded).

The tip/absorbent head 151 may include any suitable material, which may vary from one embodiment to the next. The tip/absorbent head 151 may include or comprise liquid absorbing material, which may absorb sanitizing liquid and subsequently dispense the sanitizing liquid onto and/or near the site of catheterization. For instance, the tip/absorbent head 151 may comprise a suitable foam, sponge, cotton, etc.

The tip/absorbent head 151 may be attached to the elongated stem/stick 152 with any number of suitable mechanisms, which may vary from one embodiment to the next. For example, the tip/absorbent head 151 may be attached to the elongated stem/stick 152 with an adhesive, may be ultrasonically welded to the stem/stick 152, etc. The elongated stem 152 may enter into the tip/absorbent head 151 to a predetermined depth, which may facilitate suitably securing together the tip/absorbent head 151 and the elongated stem/stick 152, while leaving a sufficient portion of the tip/absorbent head 151 beyond the elongated stem/stick 152 (e.g., in a manner that avoids contacting and/or injuring or hurting the patient with the elongated stem/stick 152 during application of the sanitizing liquid at the insertion site. For instance, after being secured to the elongated stem/stick 152, the tip/absorbent head 151 may have sufficient flexibility and sufficient resilience and/or stiffness, such that the tip may substantially remain unbent after absorption of the sanitizing liquid and may resiliently bend during application of the sanitizing liquid at the insertion site.

As described above, in some examples, the catheter assembly in the catheterization tray may be oriented generally parallel to the support surface that supports the catheterization tray. The catheter assembly in the catheterization tray may be generally oriented vertically or perpendicularly to the support surface. FIGS. 36A-36B illustrate a catheterization system 100a that includes a catheterization tray 200a, which secures a catheter assembly and/or one or more components or elements for catheterization procedures. Except as described herein, the catheterization system 100a and its elements and components may be similar to or the same catheterization system 100 (FIG. 30A) and its elements or components. For instance, except as described herein, the catheterization tray 200a and catheterization elements and components contained in the catheterization tray 200a may be similar to the catheterization tray 200 (FIGS. 31A-32) and catheterization elements or components contained therein.

For example, as shown in FIG. 36A, the catheterization tray 200a may have a generally rectangular shape, which may be defined by peripheral walls 201a-204a. The peripheral walls 201a-204a may be approximately planar, hence, may define a box-like structure or periphery of the catheterization tray 200a. The catheterization tray 200a also may include a top compartment 210a that may contain instructions and/or one or more catheterization components. In one embodiment, the top compartment 210a may be defined by separator walls 211a, 212a and a bottom wall 213a. In one embodiment, the separator walls 211a, 212a and/or the bottom wall 213a may be removable from the catheterization tray 200a.

In one embodiment, removal of the separator walls 211a, 212a and/or of the bottom wall 213a may provide access to additional catheterization components contained in the catheterization tray 200a. For example, as shown in FIG. 36B, after removing the separator walls 211a, 212a and the bottom wall 213a (FIG. 36A), a center compartment 220a of the catheterization tray 200a may be exposed and/or accessible to the user. For instance, the compartment 220a may house or contain catheter assembly 190. In one embodiment, the compartment 210a may be separated from adjacent compartments by one or more separator walls (e.g., by separator walls 221a, 222a). As mentioned above, the catheter assembly 190 in the compartment 210a may be oriented approximately vertically relative to the support surface (e.g., when the catheterization tray 200a is placed on the support surface, such as a surface of the patient's bed).

In one embodiment, the separator walls 221a, 222a may separate the center compartment 220a from adjacent compartments 230a, 240a. Compartments 230a and/or 240a may house or contain various catheterization elements or components for procedure, which may be similar to or the same as catheterization components described above in connection with catheterization tray 200 (FIGS. 31A-32). In some instances, the separator walls 221 and/or 222a may be removable from the catheterization tray 200a, which may facilitate removal of catheterization elements or components from the catheterization tray 200a.

The catheterization tray 200a may be constructed of any suitable material. For example, the catheterization tray 200a may be constructed of thick sheet-like material or panels (e.g., plastic material). For instance, thickness of the panels may be in one or more of the following ranges: about 0.1 inches to about 0.2 inches; about 0.15 inches to about 0.3 inches; about 0.25 inches to about 0.5 inches. It should be appreciated, however, panel thickness may be less than 0.1 inches or greater than 0.5 inches. Moreover, the catheterization tray 200a may be reused after the catheterization procedure (e.g., the catheterization tray 200a may be sanitized and/or repacked for reuse).

In one embodiment, the catheterization tray may be at least partially disassembled (e.g., in addition to or in lieu of removing separator walls). FIG. 37A illustrates a catheterization system 100b that may include a catheterization tray 200b, which may be unfolded to access contents therein. As mentioned above, the catheterization system 100b may include a catheterization tray 200b that may be wrapped in a CSR sterile wrap 130b, which may be unwrapped to access the catheterization tray 200b. For instance, initially a flap or portion 131b of the CSR sterile wrap 130b may be unfolded toward the patient (e.g., thereby covering the support surface with the sterile portion 131b of the CSR sterile wrap 130b.

In one embodiment, the CSR sterile wrap 130b may include a pocket 132b, which may be exposed when the CSR sterile wrap 130b is unwrapped to expose the catheterization tray 200b. In one embodiment, during and/or after the catheterization procedure, used items or trash may be placed in the pocket 132b. Subsequently, the trash may be disposed together with the CSR sterile wrap 130b.

A drape (e.g., the fenestrated drape 270) may be attached to the CSR sterile wrap 130b, such that after the unwrapping the CSR sterile wrap 130b, the drape is exposed and may be removed from the CSR sterile wrap 130b and used in the catheterization procedure. In one embodiment, the fenestrated drape 270 may be attached to the CSR sterile wrap 130b in any suitable manner, which may vary from one embodiment to the next. In one example, the fenestrated drape 270 may be attached to the CSR sterile wrap 130b with light adhesive, tape, tabs, etc.

As mentioned above, the catheterization tray 200b may be exposed after unwrapping the CSR sterile wrap 130b. The catheterization tray 200b may include one or more identifiers 260b, which may identify or suggest an order of step and/or use of catheterization components in the catheterization procedure (e.g., the identifiers may be on one or more outer surfaces of the catheterization tray 200b). For example, the identifiers 260b may be located on the top surface of the catheterization tray 200b and may indicate further steps in the catheterization procedure. According to one embodiment, a top panel 201b of the catheterization tray 200b may be opened to unfold the catheterization tray 200b and access the catheterization components in the catheterization tray 200b.

As shown in FIG. 37B, after opening the catheterization tray 200b, the user may access the compartment 210b, which may contain the catheter assembly 190 for the catheterization procedure. For instance, the top panel 201b together with a side panel 202b (connected thereto) may be unfolded away from panels 203b, 204b, 205b. More specifically, the side panels 203b, 204b, stiffening ribs 205b may partially define the periphery of the compartment 210b. Unfolding the side panel 202b and the top panel 201b from the side panels 203b, 204b, 205b may provide access to the compartment 210b through a side (from which the side panel 202b was unfolded) and through the top (where the top panel 201b was removed). In one embodiment, the side panel 202b and the top panel 201b may be unfolded in a general direction that is opposite to or away from the insertion site (e.g., in a manner that would not interfere with the catheterization procedure).

Moreover, on the interior surface of the panel 201b, the catheterization tray 200b may include additional or alternative catheterization components, such as the syringe 170 and swabs 150. Such catheterization components may be attached or secured to the top panel 201b and/or to the side panel 202b. For example, the syringe 170 may be secured to the top panel 201b with one or more straps 220b. Furthermore, in some instances, the swabs 150 may be secured to the top panel 201b within one or more pockets 230b. It should be appreciated that, the catheterization components (such as the syringe 170, swabs 150, etc.) may be attached or secured to the top panel 201b in any number of suitable ways and with any number of suitable mechanisms (e.g., adhesive, tabs, etc.). In any event, the catheterization components secured on the interior of the top panel 201b and/or side panel 202b may be accessible and removable therefrom after unfolding thereof away from the side panels 203b, 204b, 205b.

Moreover, the side panel 202b and/or the top panel 201b may include one or more procedural indicators 260b near one or more corresponding catheterization components. For example, procedural indicators 260b may identify the catheterization components with a number that may correspond with a suggested number of a step in a suggested sequence of steps for the catheterization procedure. Also, the catheterization components and corresponding procedural indicators 260b may be arranged in a sequential manner, such that the indicators with higher numbers and corresponding catheterization components are generally positioned increasingly farther from the insertion site. In other words, the catheterization components that are used earlier in the catheterization procedure may be closer to the insertion site, while the catheterization components that are used later in the catheterization procedure are located farther away from the insertion site (based on the orientation of the catheterization tray 200b).

In one embodiment, the catheterization tray 200b may include a horizontal panel 207b, which may be connected to and extend from the side panel 204b (e.g., the horizontal panel 207b may be folded into the compartment 210b and/or may be approximately parallel to the support surface supporting the catheterization tray 200b). In some instances, the horizontal panel 207b may support and/or secure one or more catheterization components. For example, the horizontal panel 207b may secure a pouch 180b with lubricant that may be removed therefrom and used in the catheterization procedure.

In one embodiment, the side panel 204b and horizontal panel 207b may be unfolded away from the side panels 203b and 205b, as shown in FIG. 37C. For instance, unfolding the side panel 204b may provide access into the compartment 210b. Furthermore, one or more catheterization components may be attached to the side panel 204b and/or to the interior side of the horizontal panel 207b, on the interior surface thereof. For example the sanitizer packet 160 may be attached to the horizontal panel 207b and/or to the side panel 204b (e.g., with light adhesive). Also, the catheterization tray 200b may include indicator 260b identifying the step or particular order or place in the sequence of the catheterization procedure where the sanitizer packet 160 may be used.

As described above, the catheterization system may include a catheterization tray wrapped into a sterile wrap, which may be used during the catheterization procedure. The catheterization system may include one or more catheterization components packaged by and/or secured in a sterile wrap (e.g., directly in the sterile wrap without the catheterization tray). Such catheterization system may reduce waste or materials that are thrown away after the catheterization procedure. For instance, after completing the catheterization material, the sterile wrap may be disposed and/or composted to reduce long term waste from the catheterization system.

The above packages, trays, systems, assemblies, methods, etc. have generally been described as being applied to catheterization packages, catheterization trays, and catheterization procedures; however, the principles described may be applied to other types of medical procedure packages, trays, systems, assemblies, and methods. Further, the features described in one embodiment may generally be combined with features described in other embodiments.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A catheterization system, comprising:
   a catheterization tray having a length greater than a width, the catheterization tray including a procedural indicator on a surface thereof, the catheterization tray comprising:
      a first compartment containing a drainage system including a Foley catheter, the first compartment defined by a first compartment wall;
      a second compartment separated from the first compartment by the first compartment wall, the second compartment containing a lubricating component and an inflating component; and
      a third compartment separated from the first compartment by the first compartment wall, the third compartment including a plurality of inclined channels, each of the plurality of inclined channels including a plurality of snap-in features.

2. The catheterization system according to claim 1, wherein a plurality of swabs are disposed in the third compartment, each swab of the plurality of swabs including an elongated stem and an absorbent head secured to or integrated with the elongated stem, the elongated stem of each swab of the plurality of swabs secured in one of the plurality of inclined channels by the plurality of snap-in features.

3. The catheterization system according to claim 2, wherein a distal portion of the absorbent head is wider than a proximal portion of the absorbent head, the proximal portion being secured to or integrated with the elongated stem.

4. The catheterization system according to claim 2, wherein each elongated stem of each swab of the plurality of swabs has an approximately rectangular cross-sectional shape.

5. The catheterization system according to claim 1, wherein the plurality of snap-in features for each of the plurality of inclined channels extend from facing sides and are longitudinally offset.

6. The catheterization system according to claim 5, wherein each of the plurality of inclined channels includes precisely three snap-in features, wherein a first of the three snap-in features on a first side is longitudinally positioned between a second snap-in feature and a third snap-in feature on a second side.

7. The catheterization system according to claim 6, wherein the three snap-in features are similarly positioned on each of the plurality of inclined channels.

8. The catheterization system according to claim 1, wherein the third compartment includes a well, and wherein each of the plurality of inclined channels is in fluid communication with the well.

9. The catheterization system according to claim 1, wherein the first compartment has a first length and a first width, wherein the first compartment wall has a first height, and wherein the second compartment has a second length extending along the first length, the second length longer than the first length.

10. The catheterization system according to claim 9, wherein the third compartment extends along the first width perpendicular to the second compartment.

11. The catheterization system according to claim 1, further comprising a sterile wrap removably folded around the catheterization tray, the sterile wrap having a folded configuration and an unfolded configuration, the sterile wrap maintained in the folded configuration by a belly band, wherein the belly band includes orientation instructions.

12. The catheterization system according to claim 11, wherein the belly band further comprises instructions for use of the catheterization tray.

13. The catheterization system according to claim 11, further comprising a packaging label disposed on top of the sterile wrap, the packaging label including at least three sides folded into a different plane from a top portion of the packaging label, wherein each of the at least three sides of the packaging label are visible to a user after packaging of the catheterization system.

14. The catheterization system according to claim 11, wherein a pair of sterile gloves are positioned on top of the catheterization tray and are accessible after removal of the belly band and transitioning the sterile wrap from the folded configuration to the unfolded configuration.

15. The catheterization system according to claim 14, wherein a packaging label is positioned over the sterile wrap in the folded configuration, the packaging label including information squares on a top surface and at least two side surfaces.

16. The catheterization system according to claim 15, wherein a sealed bag is positioned around the catheterization tray and the packaging label such that the at least two side surfaces are disposed orthogonal to the top surface of the packaging label, thereby providing visibility of the packaging label in multiple planes.

17. The catheterization system according to claim 16, further comprising a perineal care packet positioned between the sterile wrap in the folded configuration and the packaging label, wherein the perineal care packet includes one or more items in a sealed baggy.

18. The catheterization system according to claim 1, wherein the second compartment has a bottom surface located closer to a top of the catheterization tray than a bottom surface of the first compartment.

19. The catheterization system according to claim 18, wherein the lubricating component and the inflating component in the second compartment are disposed in separate syringes.

20. The catheterization system according to claim 19, wherein the first compartment wall includes a first reduced height portion between the first compartment and the second compartment to provide access to at least one of the separate syringes.

21. The catheterization system according to claim 1, wherein the catheterization tray is defined by an outer shell including an outer peripheral wall with at least one reduced height portion having an instruction printed on a surface thereof.

22. The catheterization system according to claim 21, wherein the at least one reduced height portion includes a first reduced height portion on the outer peripheral wall along the second compartment, and a second reduced height portion on the outer peripheral wall along the third compartment.

23. The catheterization system according to claim 1, wherein the drainage system includes a drainage bag, a drainage tubing, and a stabilization device.

24. The catheterization system according to claim 1, wherein the procedural indicator is printed onto the surface of the catheterization tray or imprinted into the surface of the catheterization tray.

* * * * *